United States Patent
Bertani et al.

(10) Patent No.: US 8,178,549 B2
(45) Date of Patent: *May 15, 2012

(54) AZABICYCLO [3. 1. O] HEXYL DERIVATIVES AS MODULATORS OF DOPAMINE D3 RECEPTORS

(75) Inventors: Barbara Bertani, Verona (IT); Francesca Cardullo, Verona (IT); Paolo Dambruoso, Verona (IT); Paola Marzorati, Verona (IT); Fabrizio Micheli, Verona (IT); Alessandra Pasquarello, Verona (IT); Catia Seri, Verona (IT); Giovanna Tedesco, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 136 days.

This patent is subject to a terminal disclaimer.

(21) Appl. No.: 12/680,785

(22) PCT Filed: Oct. 1, 2008

(86) PCT No.: PCT/EP2008/063166
§ 371 (c)(1),
(2), (4) Date: Mar. 30, 2010

(87) PCT Pub. No.: WO2009/043883
PCT Pub. Date: Apr. 9, 2009

(65) Prior Publication Data
US 2010/0210672 A1   Aug. 19, 2010

(30) Foreign Application Priority Data
Oct. 2, 2007 (GB) ................................ 0719235.4

(51) Int. Cl.
C07D 403/14 (2006.01)
C07D 413/14 (2006.01)
A61K 31/513 (2006.01)

(52) U.S. Cl. ........................................ 514/274; 544/310
(58) Field of Classification Search .............. 544/310; 514/274
See application file for complete search history.

(56) References Cited

U.S. PATENT DOCUMENTS
5,908,844 A   6/1999  Steiner et al.
7,727,988 B2 * 6/2010 Bertani et al. ............ 514/252.02

FOREIGN PATENT DOCUMENTS
WO  WO 2006/108701  10/2006
WO  WO 2007/022934   3/2007
WO  WO 2007/113232  10/2007
WO  WO 2007/113260  10/2007

OTHER PUBLICATIONS
Le Foll et al., PubMed Abstract (Expert Opinion Investig Drugs, 16(1):45-57), Jan. 2007.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*

* cited by examiner

Primary Examiner — Deepak Rao
(74) Attorney, Agent, or Firm — Bonnie L. Deppenbrock

(57) ABSTRACT

The present invention relates to novel compounds of formula (I) or a salt thereof:

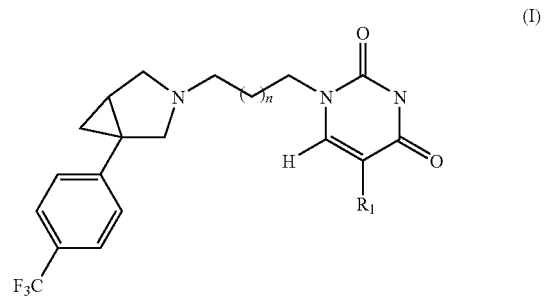

wherein
$R_1$ is a 5-membered heteroaryl group, optionally fused with a 6-membered hetero or carbocycle; such 5 or 11-membered system, may be optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl, halo$C_{1-4}$alkoxy and $SF_5$; and n is 1 or 2; their use in therapy, as modulators of dopamine $D_3$ receptors, e.g. to treat drug dependency, as antipsychotic agents, to treat obsessive compulsive spectrum disorders, or premature ejaculation.

2 Claims, No Drawings

AZABICYCLO [3. 1. O] HEXYL DERIVATIVES AS MODULATORS OF DOPAMINE D3 RECEPTORS

This application is a 371 of International Application No. PCT/EP2008/063166, filed 1 Oct. 2008, which claims the benefit of GB 0719235.4, filed 2 Oct. 2007, which are incorporated herein in their entirety.

The present invention relates to novel compounds, processes for their preparation, intermediates used in these processes, pharmaceutical compositions containing them and their use in therapy, as modulators of dopamine $D_3$ receptors.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

Recently a patent application has been published as WO2007/113232 disclosing the following compounds or some salts thereof:

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;
5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione.

The above reference doesn't disclose compounds of the present invention.

The present invention provides a compound of formula (I) or a salt thereof:

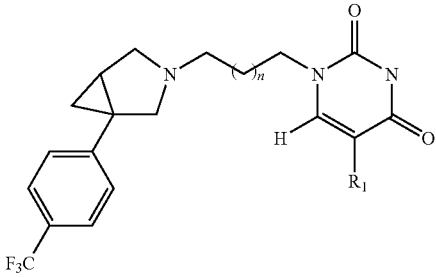

wherein
$R_1$ is a 5-membered heteroaryl group, optionally fused with a 6-membered hetero or carbocycle; such 5 or 11-membered system, may be optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl, halo$C_{1-4}$alkoxy and $SF_5$;
n is 1 or 2;
with the proviso that the compound of formula (I) is not:
5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;
5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride;
5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;
5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride.

In one embodiment, in compounds of formula (I), $R_1$ is selected in the group consisting of:
1-methyl-3-(trifluoromethyl)-1H-pyrazol-4-yl;
1-methyl-3-(trifluoromethyl)-1H-pyrazol-5-yl;
1,3-dimethyl-1H-pyrazol-5-yl;
5-methyl-1,3,4-thiadiazol-2-yl;
4,5-dimethyl-1,3-thiazol-2-yl;
1-methyl-1H-imidazol-5-yl;
1-methyl-1H-pyrrol-2-yl;
1,3,5-trimethyl-1H-pyrazol-4-yl;
1H-pyrazol-4-yl;
2-methyl-1,3-thiazol-4-yl;
4-isothiazolyl;
1,3-thiazol-2-yl;
1-methyl-1H-pyrazol-4-yl;
1H-pyrazol-1-yl;
3-(trifluoromethyl)-1H-pyrazol-1-yl;
3-(trifluoromethyl)-6,7-dihydropyrano[4,3-c]pyrazol-1(4H)-yl;
3-(trifluoromethyl)-4,7-dihydropyrano[3,4-c]pyrazol-1(5H)-yl;
3-(trifluoromethyl)-4,5,6,7-tetrahydro-1H-indazol-1-yl;
3-methyl-1H-pyrazol-1-yl;
4-methyl-1H-pyrazol-1-yl;
3-methyl-1,2,4-oxadiazol-5-yl;
2,4-dimethyl-1,3-thiazol-5-yl;
4-methyl-1,3-thiazol-2-yl;
3-methyl-4-isothiazolyl;
1H-pyrazol-3-carbonitrile;
and 5-methyl-4-isoxazolyl.

Because of the presence of the fused cyclopropane, compounds of formula (I) are believed to have a "cis" disposition of the substituents (both groups linked to the bicyclic ring system are on the same face of this bicyclic ring system).

In one embodiment of the present invention compounds of formula (I)' are provided which correspond to the compounds of formula (I), or salts thereof, having "cis" disposition, represented by the bold highlight of the bonds

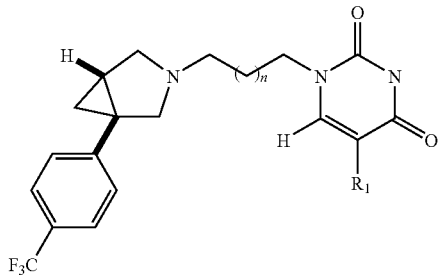

(I)' wherein $R_1$ and n are defined as above for compounds of formula (I);

with the proviso that the compound of formula (I)' is not:

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride;

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride.

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds means the "cis" configuration); through optical resolution of a mixture containing the two stereoisomers which are enantiomers with respect to the chiral centres in the cyclopropane, single stereoisomers of compounds of formula (I)' may be obtained as shown in the scheme below:

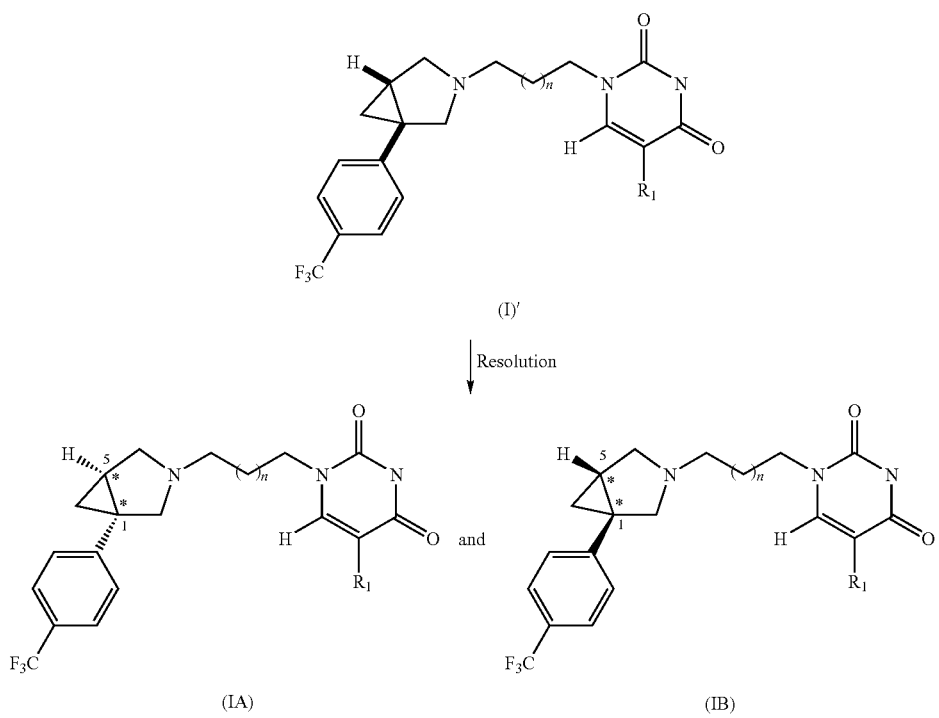

Absolute configuration of chiral center at position named 1 and 5 may be assigned using Cahn-Ingold-Prelog nomenclature based on groups' priorities.

In one embodiment of the present invention compounds of formula (IA), or salts thereof, are provided that correspond to stereochemical isomers of compounds of formula (I)', enriched in configuration (1S,5R) at chiral centers at position named 1 and 5:

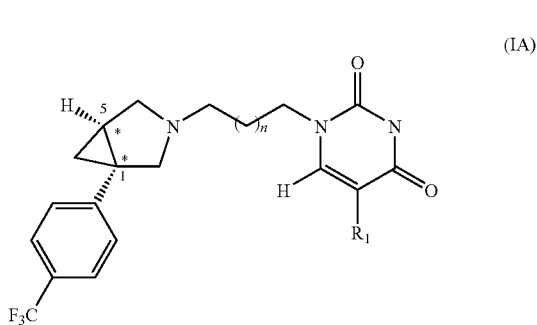

In another embodiment of the present invention compounds of formula (IB), or salts thereof, are provided that correspond to stereochemical isomers of compounds of formula (I)', enriched in configuration (1R,5S) at chiral centers at position named 1 and 5:

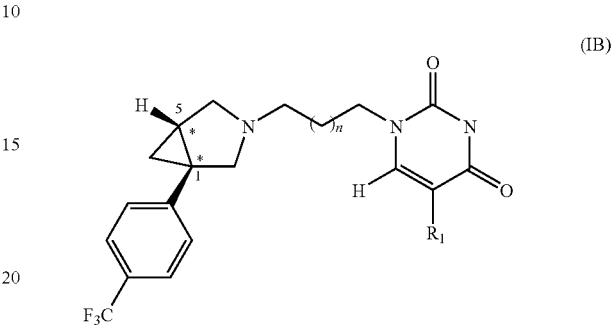

wherein $R_1$ and n are defined as above for compounds of formula (I),
with the proviso that the compound of formula (IA) is not:
5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;
5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride;
5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;
5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride.

It is intended in the context of the present invention that stereochemical isomers of formula (IA) enriched in configuration (1S,5R) at centers named 1 and 5, correspond in one embodiment to at least 90% e.e. (enantiomeric excess). In another embodiment the isomers correspond to at least 95% e.e. In another embodiment the isomers correspond to at least 99% e.e.

In another embodiment of the present invention compounds of formula (IB), or salts thereof, are provided that correspond to stereochemical isomers of compounds of formula (I)', enriched in configuration (1R,5S) at chiral centers at position named 1 and 5:

wherein $R_1$ and n are defined as above for compounds of formula (I),
with the proviso that the compound of formula (IB) is not:
5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;
5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride;
5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride;
5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;
5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride.

All embodiments described for compounds of formula (I) apply mutatis mutandis to compounds of formula (I)', (IA), (IB).

The term '$C_{1-4}$ alkyl' as used herein as a group or a part of the group refers to a linear or branched alkyl group containing from 1 to 4 carbon atoms; examples of such groups include methyl, ethyl, propyl, isopropyl, n-butyl, isobutyl, tert butyl.

The term '$C_{1-4}$ alkoxy group' as used herein may be a linear or a branched chain alkoxy group, for example methoxy, ethoxy, propoxy, prop-2-oxy, butoxy, but-2-oxy or methylprop-2-oxy and the like.

The term '$C_{1-4}$ alkanoyl group' as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term 'halogen' as used herein refers to a fluorine, chlorine, bromine or iodine atom.

The term 'halo $C_{1-4}$ alkyl' as used herein means an alkyl group having one or more carbon atoms and wherein at least one hydrogen atom is replaced with halogen such as for example a trifluoromethyl group and the like.

The term 'halo $C_{1-4}$ alkoxy group' as used herein may be a $C_{1-4}$ alkoxy group as defined before substituted with at least one halogen, preferably fluorine, such as $OCHF_2$, or $OCF_3$.

The term '5 membered heteroaryl' as used herein means an aromatic monocyclic heterocycle ring of 5 members and having at least one heteroatom selected from nitrogen, oxygen and sulfur, and containing at least 1 carbon atom.

Representative 5 membered monocyclic heteroaryl groups include (but are not limited to): furyl, thiophenyl, pyrrolyl, pyridyl, oxazolyl, isooxazolyl, pyrazolyl, imidazolyl, thiazolyl, isothiazolyl, triazolyl and tetrazolyl.

The term '6 membered heterocyclic or carbocyclic group' means a 6 membered monocyclic carbocycle ring which is either saturated, unsaturated or aromatic, and which optionally contains from 1 to 4 heteroatoms independently selected from nitrogen, oxygen and sulfur, and wherein the nitrogen and sulfur heteroatoms may be optionally oxidized, and the nitrogen heteroatom may be optionally quaternized.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a physiologically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

In one embodiment, n is 1. In another embodiment, n is 2.

Certain of the compounds of the invention may form acid addition salts with one or more equivalents of the acid. The present invention includes within its scope all possible stoichiometric and non-stoichiometric forms.

Pharmaceutically acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) or salts thereof, may exist as polymorphs, which are included in the present invention.

Hereinafter, compounds of formula (I) and their pharmaceutically acceptable salts, solvates and prodrugs defined in any aspect of the invention (except intermediate compounds in chemical processes) are referred to as "compounds of the invention".

Those skilled in the art will appreciate that in the preparation of the compounds of the invention, it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenyl-methoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and non-pharmaceutically acceptable salts thereof that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and non-pharmaceutically acceptable salts thereof can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

It will be appreciated by the person skilled in the art that compounds of formula (I) may exist in the tautomeric forms (IC) and (ID) as below described:

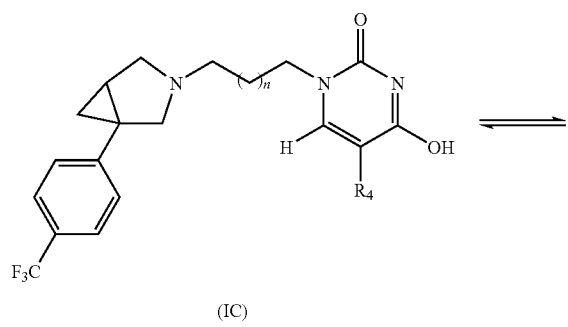

(IC)

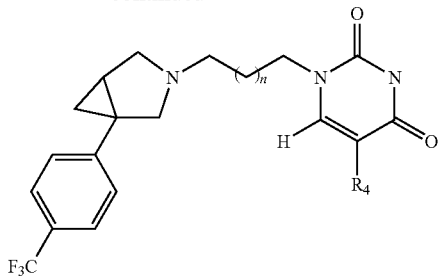

(ID)

Both tautomeric forms are intended to be included within the scope of this invention.

In one embodiment, example compounds of the present invention include:
5-[1-methyl-3-(trifluoromethyl)-1H-pyrazol-4-yl]-1-(3-{(1S,5R)-1-[4-(trifluoromethyl)phenyl]-3-azabicyclo-[3.1.0]hex-3-yl}propyl)-2,4(1H,3H)-pyrimidinedione;
5-[1-methyl-3-(trifluoromethyl)-1H-pyrazol-5-yl]-1-(3-{(1S,5R)-1-[4-(trifluoromethyl)phenyl]-3-azabicyclo[3.1.0]hex-3-yl}propyl)-2,4(1H,3H)-pyrimidinedione;
5-(1,3-dimethyl-1H-pyrazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(5-methyl-1,3,4-thiadiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(4,5-dimethyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1-methyl-1H-imidazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1-methyl-1H-pyrrol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;
1-(3-{(1S,5R)-1-[4-(trifluoromethyl)phenyl]-3-azabicyclo[3.1.0]hex-3-yl}propyl)-5-(1,3,5-trimethyl-1H-pyrazol-4-yl)-2,4(1H,3H)-pyrimidinedione;
5-(1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2-methyl-1,3-thiazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1-methyl-1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;
1-(3-{(1S,5R)-1-[4-(trifluoromethyl)phenyl]-3-azabicyclo[3.1.0]hex-3-yl}propyl)-5-[3-(trifluoromethyl)-1H-pyrazol-1-yl]-2,4(1H,3H)-pyrimidinedione;
1-(3-{(1S,5R)-1-[4-(trifluoromethyl)phenyl]-3-azabicyclo[3.1.0]hex-3-yl}propyl)-5-[3-(trifluoromethyl)-1H-pyrazol-1-yl]-2,4(1H,3H)-pyrimidinedione;

5-[3-(trifluoromethyl)-6,7-dihydropyrano[4,3-c]pyrazol-1 (4H)-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-[3-(trifluoromethyl)-6,7-dihydropyrano[4,3-c]pyrazol-1 (4H)-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-[3-(trifluoromethyl)-4,7-dihydropyrano[3,4-c]pyrazol-1 (5H)-yl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-[3-(trifluoromethyl)-4,5,6,7-tetrahydro-1H-indazol-1-yl]-2,4(1H,3H)-pyrimidinedione;

5-(3-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-1H-pyrazole-3-carbonitrile;

5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)pyrimidinedione;

5-(3-methyl-1,2,4-oxadiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2,4-dimethyl-1,3-thiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

or a salt thereof.

In another embodiment, example compounds of the present invention include:

5-[1-methyl-3-(trifluoromethyl)-1H-pyrazol-4-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-[1-methyl-3-(trifluoromethyl)-1H-pyrazol-5-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-(1,3-dimethyl-1H-pyrazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(5-methyl-1,3,4-thiadiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4,5-dimethyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-imidazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-pyrrol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-(1,3,5-trimethyl-1H-pyrazol-4-yl)-2,4(1H,3H)-pyrimidinedione;

5-(1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-1,3-thiazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-[3-(trifluoromethyl)-1H-pyrazol-1-yl]-2,4(1H,3H)-pyrimidinedione;

5-[3-(trifluoromethyl)-6,7-dihydropyrano[4,3-c]pyrazol-1 (4H)-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-[3-(trifluoromethyl)-4,7-dihydropyrano[3,4-c]pyrazol-1 (5H)-yl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-[3-(trifluoromethyl)-4,5,6,7-tetrahydro-1H-indazol-1-yl]-2,4(1H,3H)-pyrimidinedione;

5-(3-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-1H-pyrazole-3-carbonitrile;

5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-1,2,4-oxadiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2,4-dimethyl-1,3-thiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-methyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(5-methyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

or a salt thereof.

In another embodiment, example compounds of the present invention include:

5-(1,3-dimethyl-1H-pyrazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-imidazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-pyrrol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-(1,3,5-trimethyl-1H-pyrazol-4-yl)-2,4(1H,3H)-pyrimidinedione;

5-(1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(3-methyl-4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(2,4-dimethyl-1,3-thiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;
or a salt thereof.

Some of the compounds of the present invention or intermediates thereof may be prepared following some of the procedures described in PCT International Publication WO2005/080382.

The present invention also provides a process for preparing a compound of formula (I)' or a salt thereof as defined above, which comprises the steps of:

a) reacting a compound of formula (II):

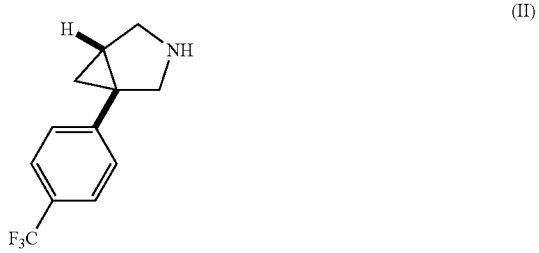

(II)

with a compound of formula (III):

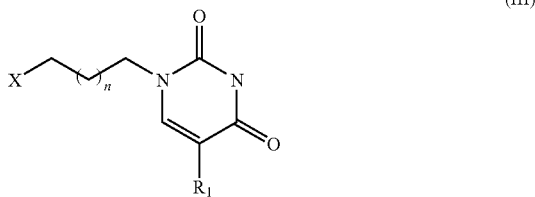

(III)

wherein $R_1$ and n are as defined for formula (I) and X is a leaving group;

Or b) reacting a compound of formula (II) as above defined with a compound of formula (IV)

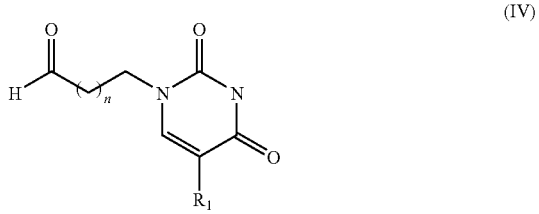

(IV)

wherein $R_1$ and n are as defined for formula (I);

and thereafter optionally for process (a) or process (b):

(i) removing any protecting group(s); and/or (ii) forming a salt; and/or (iii) converting a compound of formula (I)' or a salt thereof to another compound of formula (I)' or a salt thereof.

Process (a) may be performed using conventional methods for the formation of a tertiary amine. The leaving group X can be halogen such as chlorine. Alternatively X can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Process (b) may be performed using conventional methods for the formation of a tertiary amine by means of reductive ammination. For example the reaction may be carried out using sodium triacetoxy borohydride in a suitable solvent such as 1,2 dichloroethane at 0° C.

Compounds of formula (II) may be prepared by methods well known in the art (e.g. *J. Med. Chem.* 1981, 24, 481-490 or PCT International Publication WO2005/080382).

A compound of formula (III) as above defined may itself be prepared by reacting a compound of formula (V):

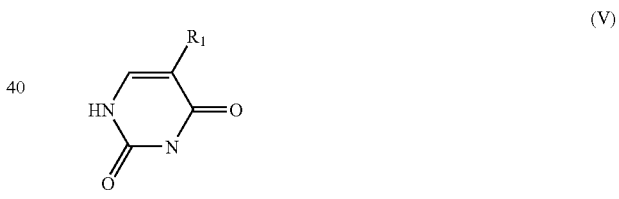

(V)

wherein $R_1$ is as hereinbefore defined, with a compound of formula (VI):

(VI)

wherein n is defined as for formula (I), X is as defined above for compounds of formula (III) and L is a leaving group, e.g., a bromine atom.

Alternatively L can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When L is a halogen the reaction may be carried out using a base such as potassium carbonate in the presence of a source of iodide such as sodium iodide in a solvent such as N,N-dimethylformamide at a suitable temperature, e.g. 60° C.

A compound of formula (IV) as above defined may be prepared by:

f) reacting a compound of formula (V):

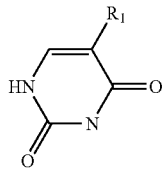

(V)

wherein $R_1$ is defined as for compounds of formula (I), with a compound of formula (VII)

MCH(CH$_2$)$_n$X  (VII)

wherein n is defined as for formula (I), X is as defined above for compounds of formula (III) and M is an appropriate carbonylic protecting group (for example dimethylacetale or dioxolane);
and then g) cleavage of the protecting group.

Cleavage of the protecting group may be carried out under appropriate conditions known to the man skilled in the art. For example, when M is dimethylacetale, the cleavage may carried out by treatment with a diluted solution of hydrochloric acid in dioxane or methanol under gentle heating (e.g. 60° C.).

A compound of formula (IV), as above defined, may also be prepared by:

h) reacting a compound of formula (V), as above defined:

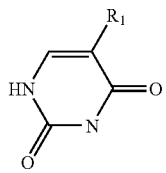

(V)

with a compound of formula (VIII)

NCH$_2$(CH$_2$)$_n$X  (VIII)

wherein n is defined as for formula (I), X is as above defined and N is a protected alcoholic function (for example: terbutyldimethylsilyl) to form a compound of formula (IX)

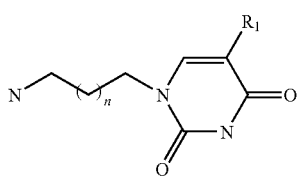

(IX)

and then i) cleavage of the protecting group under appropriate conditions known to the man skilled in the art and subsequent oxidation of the free alcoholic function obtained to carbonyl group.

For example when N is a terbutyl dimethyl silyl protecting group the cleavage can be performed by treatment with a 1N solution of hydrochloric acid in dioxane at 0° C. for 1 hour. Appropriate conditions for the oxidation step comprise Dess-Martin periodinane mediated oxidation in dry THF as solvent at 0° C. for 1 hour.

A compound of formula (IVa), which is a compound of formula (IV) as above defined wherein n=1, may also be prepared by:

h) reacting a compound of formula (V), as above defined:

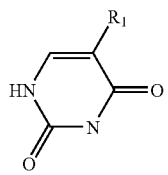

(V)

with a compound of formula (XXII)

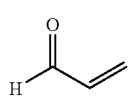

(XXII)

By means of azaMichael reaction. Typical reaction conditions may comprise the use of N,N-DMF as solvent and TEA as base at room temperature.

Compounds of formula (VI), (VII), (VIII) and (XXII) are commercially available or may be prepared through reactions known in the literature.

Compounds of formula (V) are either commercially available or may be prepared through reactions known in the literature or through the procedures herebelow described.

Compounds (V) as above defined may be prepared according to the following synthetic scheme:

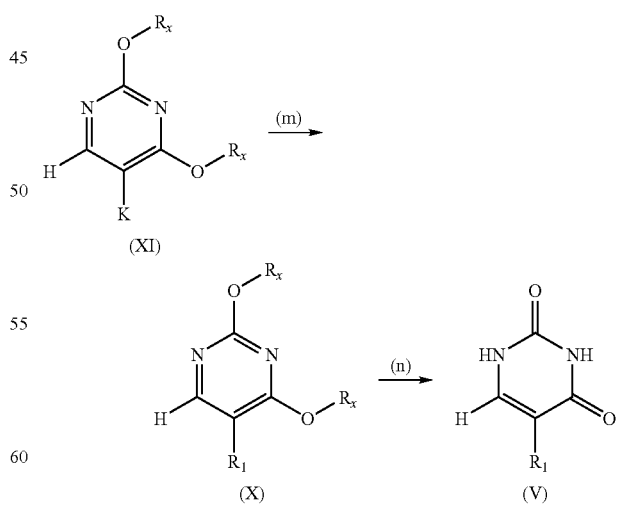

Step (m) means coupling of compounds of formula (XI) (commercially available, wherein $R_x$ may be a methyl, benzyl or t-butyl group) with a heteroaryl boronic acid or ester to give compounds of formula (X) when K is alogen, i.e. bromine or iodine. When K is boronic acid, step (m) means coupling with a phenyl or heteroaryl alogen derivatives, i.e. bromo or iodo derivatives.

Step (n) means cleavage of the di $R_x$ protecting group to give compound (V). Suitable conditions for cleavage of methyl or t-butyl protecting groups are acidic conditions; suitable conditions for removal of benzyl comprise the use of $Me_3SiI$ in dichloromethane.

Step (m) may suitably be performed using convential method for the Suzuky coupling, using for example $Pd(OAc)2$ as the source of catalytic palladium (0), in the presence of $Na_2CO_3$ as base and a suitable aryl boronic acid or aryl boronic ester in an appropriate solvent, such as nPrOH.

Step (n) may be performed typically by using a 4N solution of hydrochloric acid in dioxane as solvent at 0° C. for 1 hour.

Some of the compounds of formula (V) as above defined may also be prepared according to the following synthetic scheme:

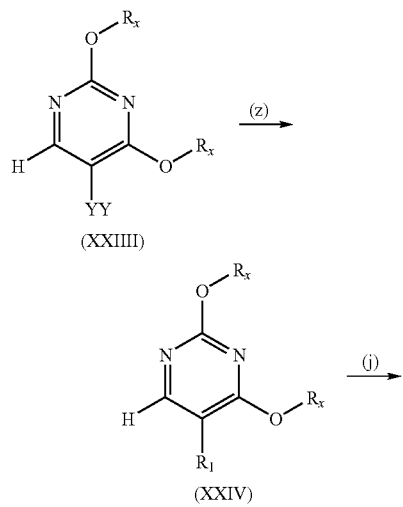

Step (z) means formation of the appropriate heterocycle $R_1$ starting from compounds of formula (XXIII) (commercially available, wherein $R_x$ may be a methyl, benzyl or t-butyl group and YY is an activated carboxylic function, i.e. ester or carboxylic acid) following well known procedures available in the art.

Step (j) means cleavage of the di $R_x$ protecting groups to give compound (V). Suitable conditions for cleavage of methyl or t-butyl protecting groups are acidic conditions; suitable conditions for removal of benzyl comprise the use of $Me_3SiI$ in dichloromethane.

Step (z) may suitably be performed using convential method for the heterocycles formation such as for example reacting the corresponding ester derivative (XXIII) with the appropriate aldoxime derivative in the presence of sodium-hydride as base and activated molecular sieves in THF as solvent Step (j) may be performed typically by using a 4N solution of hydrochloric acid in dioxane as solvent at 0° C. for 1 hour.

An alternative process for the preparation of compounds of formula (I)', as above defined, is provided according to the following scheme:

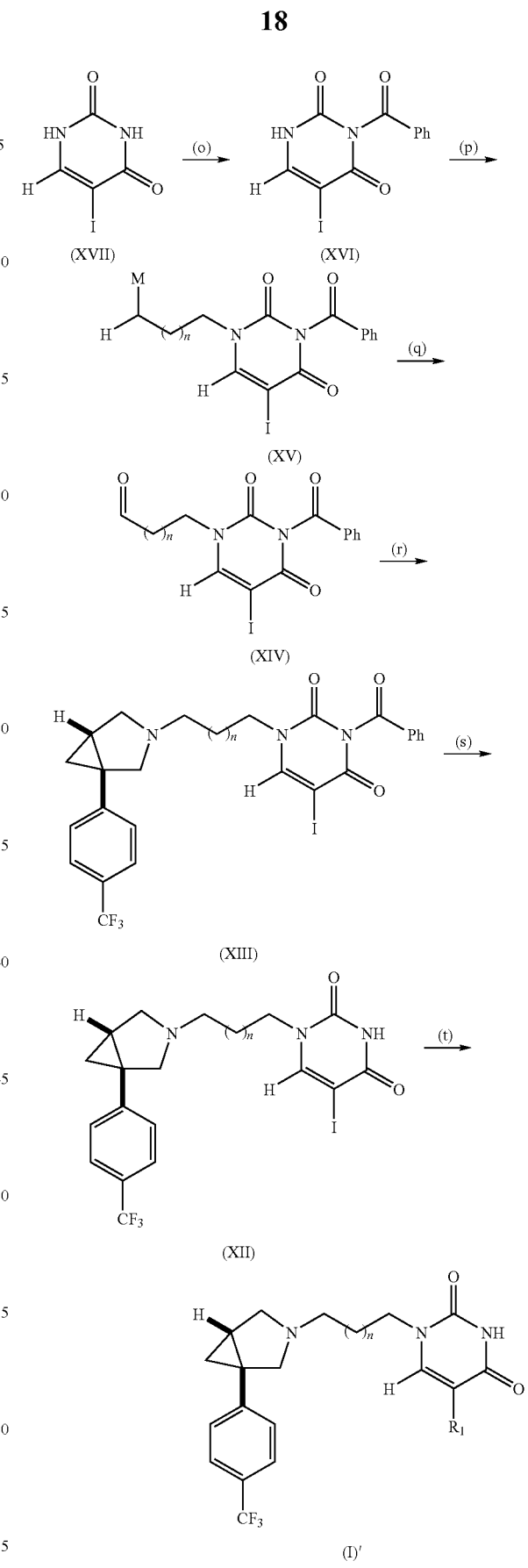

Step (o) means protection of the N-3 uracylic function of compounds of formula (XVII) with a suitable protecting group to give compounds of formula (XVI). For example, when the protecting group is a benzoyl group, the reaction may be carried out using benzoyl chloride in dry pyridine as solvent at room temperature for 3 hours.

Step (p) means alkylation of N-5 uracylic function of compounds of formula (XVI) to give compounds of formula (XV), wherein M is an appropriate carbonyl protecting group (for example dimethylacetale or dioxolane). The reaction can be suitably performed for example using commercially available 3-bromo-1,1-dimethoxy propane or 3-bromo-1,1-dimethoxy butane and potassium carbonate as base in dry DMF.

Step (q) means cleavage of the carbonyl protecting group of compounds of formula (XV) to give compounds of formula (XIV). This step can be typically performed using a 1N solution of hydrochloric acid in dioxane as solvent at 60° C.

Step (r) means reductive amination of compounds of formula (XIV) to give compounds of formula (XIII). This step can be typically performed using sodium triacetoxy borohydride as reductive agent in dry 1,2-dichloroethane as solvent at 0° C. for 1 hour.

Step (s) means cleavage of the protecting group of compounds of formula (XIII) to give compounds of formula (XII). When the protecting group is a benzoyl group, the step can be performed by means of a diluted solution of $NH_3$ (3% in MeOH) at room temperature for 3 hours.

Step (t) means coupling of compound (XII) with a phenyl or heteroaryl boronic acid or ester to give compounds (I)'. This step may be performed using convential method for the Suzuky coupling, using for example $Pd(OAc)_2$ as the source of catalytic palladium (0), in the presence of $Na_2CO_3$ as base and a suitable phenyl or heteroaryl boronic acid or phenyl or heteroaryl boronic ester in an appropriate solvent, such as nPrOH.

Alternatively, compounds of formula (I)', as above defined, may be prepared through the following steps:

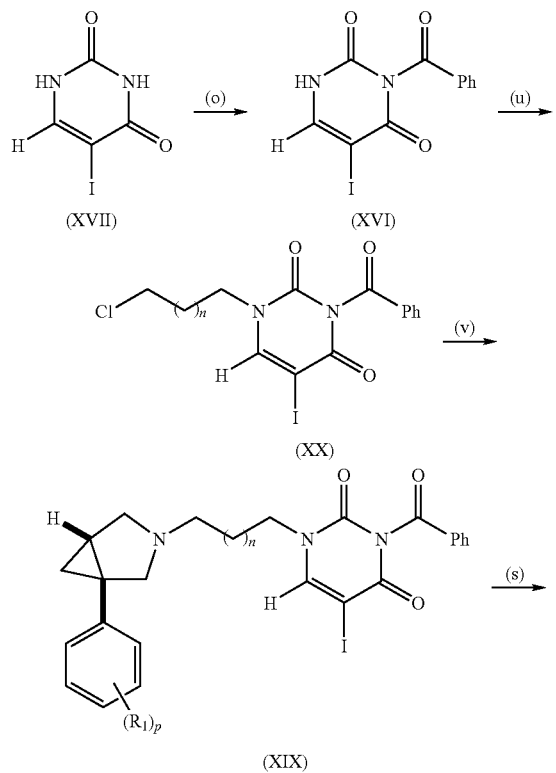

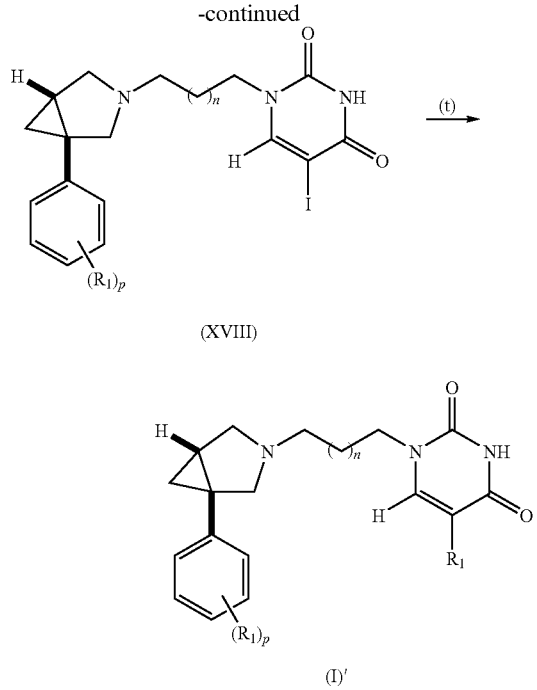

Step (o) means protection of the N-3 uracylic function of compounds of formula (XVII) with a suitable protecting group to give compounds of formula (XVI). For example, when the protecting group is a benzoyl group, the reaction may be carried out using benzoyl chloride in dry pyridine as solvent at room temperature for 3 hours.

Step (u) means alkylation of N-5 uracylic function of compounds of formula (XVI) to give compounds of formula (XX). The reaction can be suitably performed using commercially available 3-bromo-1-chloro-propane or 3-bromo-1-chloro-butane and potassium carbonate as base in dry DMF.

Step (v) means alkylation of compounds of formula (XX) to give compounds of formula (XIX). This step can be typically performed under classical alkylation conditions know to the man skilled in the art. For example the reaction may be performed in EtOH and in the presence of DIPEA, through microwave irradiation.

Step (s) means cleavage of the protecting group of compounds of formula (XIX) to give compounds of formula (XVIII). When the protecting group is a benzoyl group, the step can be performed by means of a diluted solution of $NH_3$ (3% in MeOH) at room temperature for 3 hours.

Step (t) means coupling of compound (XVIII) with a heteroaryl boronic acid or ester to give compounds (I)'. This step may be performed using convential method for the Suzuky coupling, using for example $Pd(OAc)_2$ as the source of catalytic palladium (0), in the presence of $Na_2CO_3$ as base and a suitable phenyl or heteroaryl boronic acid or phenyl or heteroaryl boronic ester in an appropriate solvent, such as nPrOH.

Compounds of formula (Ia)', which is a compound of formula (I)' as above defined wherein n is 1, may be prepared by reacting a compound of formula (XXI):

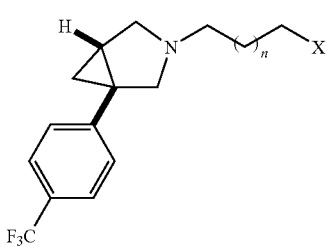

(XXI)

wherein X is a leaving group, with a compound of formula (V):

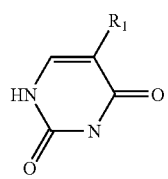

(V)

wherein $R_1$ is as hereinbefore defined.

A compound of formula (XXI) can be prepared by alkylation of a compound of formula (II) in the presence of a suitable base such as a tertiary amine, for example diisopropylethylamine, with a propyl derivative carrying two leaving groups of preferrably differential reactivity in positions 1 and 3, for example 1-bromo-3-chloropropane.

When a specific enantiomer or diastereoisomer of a compound of formula (I) or salts thereof, is required, this may be obtained for example by resolution of a corresponding enantiomeric or diastereoisomeric mixture using conventional methods.

Thus, for example, specific enantiomers or diastereoisomers of the compounds may be obtained from the corresponding enantiomeric or diastereoisomeric mixture using chiral chromatographic methods such as for example chiral HPLC.

Alternatively a specific enantiomer or diastereoisomer of a compound of general formula (I), or salts thereof, may be synthesised from the appropriate optically active intermediates using any of the general processes described herein.

Compounds of formula (I) or pharmaceutically acceptable salts thereof, have been found to exhibit affinity for dopamine receptors, in particular the $D_3$ receptor, and are expected to be useful in the treatment of disease states which require modulation of such receptors, such as psychotic conditions.

Many of the compounds of formula (I) or pharmaceutically acceptable salts thereof have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of formula (I) or salts thereof are provided which have higher (e.g. $\geq 10\times$ or $\geq 100\times$ higher) affinity for dopamine $D_3$ than dopamine $D_2$ receptors (such affinity can be measured using standard methodology—see herein).

Compounds of the invention may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse.

Other conditions which may be treated by the compounds include substance related disorders, dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, amnesia, aggression, vertigo, dementia, circadian rhythm disorders and gastric motility disorders e.g. IBS.

Compounds of formula (I) will be used for treatment of all aspects of drug dependency including prevention of relapse to and relief of withdrawal symptoms from drugs of abuse such as nicotine, alcohol, cocaine, amphetamine, methamphetamine, opiates, benzodiazepines, inhalants and inhibition of tolerance induced by opioids. In addition, compounds of formula (I) and pharmaceutically acceptable salts and solvates thereof will be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the maintenance of drug dependence and the probability of relapse or reinstatement of drug seeking and drug taking behaviors.

A wide range of psychiatric and neuropsychiatric disorders appear to be related to Obsessive-Compulsive Disorder, and form a family of related disorders referred to as obsessive-compulsive (OC) spectrum disorders. The compounds of the invention may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of the invention are also useful for the treatment of premature ejaculation.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

The term "psychotic disorder" includes:

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The term "substance-related disorder" includes:

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Compounds of the invention may be useful for the treatment of cognition impairment.

The term "cognition impairment" includes cognition impairment in other diseases such as schizophrenia, bipolar disorder, depression, other psychiatric disorders and psychotic conditions associated with cognitive impairment, e.g. Alzheimer's disease.

Within the context of the present invention, it is intended that the expression "treatment of a substance-related" disorder also includes prevention of relapse into such substance related-disorder.

In a further aspect therefore the present invention provides a method of treating a condition for which modulation of dopamine receptors (especially dopamine $D_3$ receptors) is beneficial, which comprises administering to a mammal (e.g. human) in need thereof an effective amount of a compound of the invention.

Modulation, as used herein, especially refers to inhibition/antagonism (which may also translate into inverse agonism in constitutively active receptor systems).

In one embodiment, the condition is a substance-related disorder, a psychotic disorder, an obsessive compulsive spectrum disorder or premature ejaculation.

In one embodiment, the substance-related disorder is nicotine dependence.

The invention also provides a compound of the invention for use in therapy.

The invention also provides a compound of the invention for use in the treatment of a condition in a mammal for which modulation of dopamine receptors (especially dopamine $D_3$ receptors) is beneficial.

The invention also provides the use of a compound of the invention in the manufacture of a medicament for the treatment of a condition in a mammal for which modulation of dopamine receptors (especially dopamine $D_3$ receptors) is beneficial.

In one embodiment, compounds of the invention are used in the treatment of psychoses such as schizophrenia, in the treatment of substance related disorders, in the treatment of obsessive compulsive spectrum disorders, in the treatment of premature ejaculation.

Also provided is the use of a compound of the invention in the manufacture of a medicament for the treatment of a psychotic condition, substance-related disorders in a mammal, obsessive compulsive spectrum disorders, and premature ejaculation.

Also provided is a compound of the invention for use in the treatment of a psychotic condition (e.g. schizophrenia), substance-related disorders, obsessive compulsive spectrum disorders, and premature ejaculation in a mammal.

Also provided is a compound of the invention or for use as an active therapeutic substance in a mammal, e.g. for use in the treatment of any of the conditions described herein.

In one embodiment, the mammal is a human.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of the invention and a pharmaceutically acceptable carrier. The pharmaceutical composition can be for use in the treatment of any of the conditions described herein.

Compound of the invention may be administered by any convenient method, for example by oral, parenteral (e.g. intravenous), buccal, sublingual, nasal, rectal or transdermal administration and the pharmaceutical compositions adapted accordingly.

Compound of the invention which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil.

Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the invention calculated as the free base.

The compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency of compounds of this invention can be measured by the following GTPγS scintillation proximity assay (GTPγS-SPA). Cells used in the study are Chinese Hamster Ovary (CHO) Cells for D3 and Chinese Hamster Ovary (CHO) or Human Embryonic Kidney (HEK) cells for D2.

Cell Line
CHO_D2 or HEK_D2
CHO_D3
Dopamine CHO $D_3$ transduced with bacmam G0 G-protein.

All steps are performed at 4° C. Cell membranes are prepared as follows. Cell pellets are resuspended in 10 volumes of 50 mM HEPES, 1 mM EDTA pH 7.4, using KOH.

Cells are homogenised within a glass waring blender for 2 bursts of 15 secs in 200 mls of buffer (50 mM HEPES, 1 mM leupeptin, 25 μg/ml bacitracin, 1 mM EDTA, 1 mM PMSF, 2 μM Pepstatin A). (the latter 2 reagents added as fresh ×100 and ×500 stocks respectively in ethanol). The blender is plunged into ice for 5 mins after the first burst and 10-40 mins after the final burst to allow foam to dissipate. The material is then spun at 500 g for 20 mins and the supernatant spun for 36 mins at 48,000 g. The pellet is resuspended in the same buffer as above but without PMSF and Pepstatin A. The material is then forced through a 0.6 mm needle, made up to the required volume, (usually ×4 the volume of the original cell pellet), aliquoted and stored frozen at −80° c.

The final top concentration of test drug is 3 μM in the assay and 11 points serial dilution curves 1:4 in 100% DMSO are carried out using a Biomek FX. The test drug at 1% (0.5 ul) total assay volume (TAV) is added to a solid, white Greiner polypropylene 384-well assay plate. 50% TAV (25 μl) of precoupled (for 60 mins at RT) membranes, 5 μg/well, and Wheatgerm Agglutinin Polystyrene Scintillation Proximity Assay beads (RPNQ0260, Amersham), 0.25 mg/well, in 20 mM HEPES (pH 7.4, 100 mM NaCl, 10 mM MgCl2), 60 μg/mL saponin and 3 uM for D2 and 30 uM for D3 GDP is added. The third addition is a 20% TAV (10 ul) addition of either buffer, (agonist format) or EC80 final assay concentration of agonist, Quinelorane, prepared in assay buffer (antagonist format). The assay is started by the addition of 29% TAV (15 ul) of GTP[35S] 0.38 nM final (37 MBq/mL, 1160 Ci/mmol, Amersham). After all additions assay plates are spun down for 1 min at 1,000 rpm. The final assay cocktail (50.5 μl) is incubated at room temperature to equilibrate for 3-6 hours before reading on a ViewLux™ (613/55 filter) luminescence imager 5 min/plate.

The effect of the test drug over the basal generates fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as −logfKi.

pKi results are only estimated to be accurate to about 0.3-0.5.

In the context of the present invention functional pKi (fpKi, corresponding to the negative logarithm of fKi) is used instead of functional Ki (fKi) and the compounds of formula (I) and salts thereof typically show fpKi for D3 receptors comprised between approximately 7.0 and 9.0.

In one embodiment, compounds of formula (I) or salts thereof are provided which have higher affinity for dopamine $D_3$ than dopamine $D_2$ receptors.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar" or "analogous" procedure, as will be appreciated by those skilled in the art, such a procedure may involve minor variation, for example reaction temperature, reagent/solvent amount, reaction time, work-up conditions or chromatographic purification conditions.

All temperatures refer to ° C.

Proton Magnetic Resonance (NMR) spectra may be typically recorded either on Varian instruments at 300, 400 or 500 MHz, or on a Bruker instrument at 300 and 400 MHz. Chemical shifts are expressed in parts of million (ppm, δ units). Coupling constants are in units of hertz (Hz) chemical shifts are reported in ppm downfield (d) from $Me_4Si$, used as internal standard, and are typically assigned as singlets (s), broad singlets (bs), doublets (d), doublets of doublets (dd), triplets (t), quartets (q) or multiplets (m).

Mass spectra (MS) may be typically taken on a 4 II triple quadrupole Mass Spectrometer (Micromass UK) or on a Agilent MSD 1100 Mass Spectrometer, operating in ES (+) and ES (−) ionization mode or on an Agilent LC/MSD 1100 Mass Spectrometer, operating in ES (+) and ES (−) ionization mode coupled with HPLC instrument Agilent 1100 Series. In the mass spectra only one peak in the molecular ion cluster is typically reported.

LCMS may be recorded under the following conditions: DAD chromatographic traces, mass chromatograms and mass spectrums may be taken on a UPLC/MS Acquity™ system coupled with a Micromass ZQ™ mass spectrometer operating in ESI positive. The phases used are: A) H2O/ACN 95/5+0.1% TFA; B) H2O/ACN 5/95+0.1% TFA. The gradient is: t=0 min) 95% A 5% B, t=0.25) 95% A 5% B, t=3.30) 100% B, t=4.0) 100% B, followed by 1 min of reconditioning Column: Acquity BEH C18 2.1×50 mm 1.7 um 35° C. Flow: 600 uL/min.

Mass tune: Capillary 3.25 kV, cone 20V, source temperature 115° C. desolvation T 350° C.

Unless otherwise specified, Preparative LC-MS purifications may be performed under the following conditions:

Instrument: HPLC-MS preparative system Waters (2767 and 2525) coupled with photodiode array detector and Micromass ZQ. Column: Waters XTerra MS C18 (19×300 mm, 10 um). Flow rate 20 ml/min. Mobile phase: A phase=water+0.1% TFA, B phase=acetonitrile+0.1% TFA. 0-3.0 min (A: 90%, B: 10%), 3.0 min (A: 90%, B: 10%), 3.0-26.0 min (A: 5%, B: 95%), 26.0 min (A: 5%, B: 95%), 26.0-30.0 min (A: 5%, B: 95%), 30.0 min (A: 5%, B: 95%), 30.0-30.5 min (A: 90%, B: 10%), 30.5 min (A: 90%, B: 10%), 30.5-31.5 min (A: 90%, B: 10%). The fractions containing the pure material are typically collected and the solvents evaporated. The so obtained trifluoroacetate salts are typically neutralized by passing over SCX cartridge.

Unless otherwise specified, Preparative "LC-MS conditions—basic method" may be: Column: Gemini C18 AXIA, 50×21 mm, 5 μm; Mobile phase: A: NH4HCO3 sol. 10 mM, pH10; B: CH3CN; Gradient: 35% (B) for 1 min, 35% to 45% (B) in 9 min, 45% to 100% (B) in 2 min, 100% (B) for 1.5 min; Flow rate: 17 ml/min; UV range: 210-350 nm; Ionization: ES+; Mass range: 100-900 amu. The so obtained fraction are typically evaporated to give the compound as free base.

Preparative HPLC purifications may be performed under the following conditions:

Instrument: Shimadzu (LC/8A and SCL/10A) coupled with UV spectrophotometric dector (SPD/6A). Column: Waters SymmetryPrep C18 19×30 mm×7 um; flow rate: 20 ml/min; mobile phase: A phase=water/acetonitrile 9/1+0.5% TFA, B phase=water/acetonitrile 5/95+0.5% TFA using a 30 min gradient of 5-100% solvent B.

The fractions containing the pure material are typically collected and the solvents evaporated. The so obtained trifluoroacetate salts are typically neutralized by passing over SCX cartridge.

Preparative HPLC purifications (FractionLynx) may be performed under the following conditions:

MDAP FractionLynx Autopurification System™ Waters Column: SUPELCOSIL ABZ+Plus, 100×21.2 mm, 5 μm ps Mobile phase: A: H2O+0.1% HCOOH; B: $CH_3CN$+0.1% HCOOH Gradient: t=0 min 5% (B) in 1 min, 5% to 95% (B) in 9 min, 95% to 100% (B) in 3 min
Flow rate: 20 ml/min
UV range: 210-400 nm
Ionization: ES+/ES−
Mass range: 150-900 da Optical rotations may be typically measured using a (Perkin Elmer Model 341) polarimeter operating at 589 nm (Sodium source) [Measurements are made using a 1 decimeter microcell thermostated at 23° C. Concentrations are typically 10 mg/ml (c=1)] or using a (Perkin Elmer Model 241) polarimeter operating at 589 nm (Sodium source) [Measurements are made using a 1 decimeter microcell thermostated at 23° C. Concentrations are typically 10 mg/mL (c=0.01)]. For ab initio OR assignments, the Dalton Quantum Chemistry Program are used.

Melting point determination may be performed on a Buchi B-540 apparatus.

Compounds may be named using ACD/Name PRO6.02 chemical naming software (Advanced Chemistry Development Inc., Toronto, Ontario, M5H2L3, Canada) or ISIS/Draw 2.5 SR 2 Autonom (MDL Information System, Inc)

For reactions involving microwave irradiation, a Personal Chemistry Emrys™ Optimizer may be used.

Flash silica gel chromatography may be carried out on silica gel 230-400 mesh (supplied by Merck AG Darmstadt, Germany) or over pre-packed Biotage silica cartridges.

Purification may also be performed using either Biotage manual flash chromatography (Flash+). All these instruments work with Biotage Silica cartridges.

Unless otherwise stated, all reaction are typically performed under inert atmosphere (for example under Nitrogen).

The following abbreviations are used in the text: EtOAc, AcOEt=ethyl acetate, $Et_2O$=dietyl ether, MeOH=methanol; $NaBH(AcO)_3$=sodium triacetoxyboron hydride, THF=tetrahydrofuran, CY=cyclohexane, DMSO=dimethyl sulfoxide; DMF=N,N'-dimethylformamide, DCM=dichloromethane, TEA=triethylamine, DIPEA=diisopropylethylamine, i-$Pr_2O$ or DIPE=diisopropylether, AcOH=Acetic acid, BuLi=butyllithium, SPE Cartridge=Solid Phase Extraction Cartridge; SCX Cartridge=Strong Cation Exchange Cartridge, TBAI=tetrabuthylammoniumiodide, PLS=parallel liquid synthetiser, PS-thiol=3-(3-mercaptophenyl)propanamido methyl polystyrene, MP-isocyanate=polystyrene methyl isocyanate.

Preparation 1:
3-[4-(trifluoromethyl)phenyl]-1H-pyrrole-2,5-dione
(Prep1)

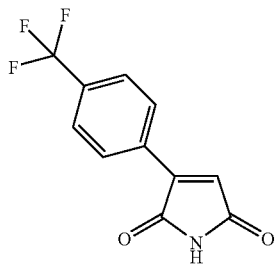

A mixture of hydrochloric acid (37% in water, 285 mL) and water (190 mL) was added to 4-(trifluoromethyl)aniline (150 g, 116 mL) at room temperature with vigorous stirring and the formed precipitate was allowed to stir for further 30 minutes. Temperature was reduced to 0° C. and sodium nitrite (70.6 g) in 180 mL of water was added dropwise to the stirred suspension. At the end of diazotisation, a clear yellow solution was obtained. Maleimide (180 g) in acetone (1.1 L) was added dropwise at 0° C. and then the pH of the solution was adjusted to 3-3.5 by adding sodium acetate. Copper (II) chloride (18.8 g) was added to the vigorously stirred mixture. After a few minutes a gas started to develop (conspicuous foaming). The reaction mixture was allowed to stir at 0° C. for 1 h and overnight at room temperature. Acetone was removed in vacuo, the residue was filtered and dried overnight in vacuo to give the title compound (155 g) as a light brown solid.

MS (ES) (m/z): 242.2 $[MH]^+$.

Preparation 2: (1R,5S/1S,5R)-1-[4-(trifluoromethyl)phenyl]-3-azabicyclo[3.1.0]-hexane-2,4-dione
(Prep2)

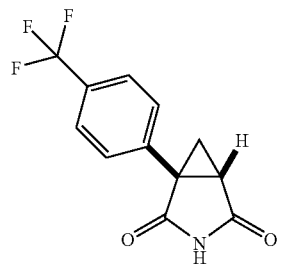

Milled sodium hydroxide (40 g) was added in small portions to a stirred solution of trimethylsulfoxonium iodide (219 g) in DMSO (anhydrous, 2 L). The resulting mixture was allowed to stir at room temperature for 1.5 h. 3-[4-(Trifluoromethyl)phenyl]-1H-pyrrole-2,5-dione (Prep1, 120 g) dissolved in DMSO (anhydrous, 0.5 L) was then added dropwise and the resulting mixture was allowed to stir at room temperature for 20 minutes. Temperature was then reduced to 0° C. and aqueous saturated $NH_4Cl$ (2 L) was slowly added, followed by $Et_2O$ (1 L). After separation of the two phases, the aqueous layer was repeatedly extracted with $Et_2O$ (3×1 L). Combined organic layers were washed with brine (2×1 L) and then dried over $Na_2SO_4$. Evaporation of the solvent gave a light brown solid which was suspended in 1 L of dichloromethane and 1 L of cyclohexane. The mixture was allowed to stir at room temperature for 45 minutes and then filtered to give the title compound (116 g) as white solid.

MS (ES) (m/z): 256.1 $[MH]^+$.

Preparation 3: (1R,5S/1S,5R)-1-[4-(trifluoromethyl)phenyl]-3-azabicyclo[3.1.0]-hexane (Prep3)

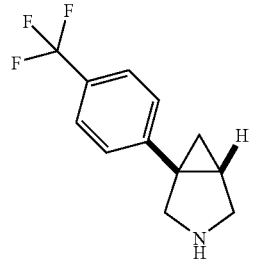

Borane (1M in tetrahydrofuran, 1.4 l) was charged into a 5 l reactor under $N_2$ and cooled at 0° C. (1R,5S/1S,5R)-1-[4-(trifluoromethyl)phenyl]-3-azabicyclo[3.1.0]hexane-2,4-dione (Prep2, 101 g) dissolved in anhydrous THF (1 L) was then added dropwise with vigorous stirring whereby the temperature was constantly kept below 5° C. and gas evolution was monitored. At the end of the addition the resulting mixture was allowed to stir at 0° C. for 1 h and then at room temperature overnight. The mixture was then cooled to 0° C. and methanol (200 mL) followed aqueous 6M hydrochloric acid solution (0.8 L) were cautiously added monitoring gas evolution. THF was then removed in vacuo, the residue was cooled to 0° C. and an aqueous 5M sodium hydroxide solution was added until pH 9-10 had been reached. The aqueous layer was extracted with Et$_2$O (3×1 L). Removal of solvent in vacuo gave the title compound (140 g) as colorless oil.

MS (ES) (m/z): 228.1 [MH]$^+$.

Preparation 4: (1S,5R)-1-[4-(trifluoromethyl)phenyl]-3-azabicyclo[3.1.0]hexane (Prep4)

(S)-(+)-Mandelic acid (94 g) was added in portions to a stirred solution of (1R,5S/1S,5R)-1-[4-(trifluoromethyl)phenyl]-3-azabicyclo[3.1.0]hexane (Prep3, 140 g) in 1.4 L of THF. The resulting mixture was stirred at room temperature for 2 h until a white precipitate was formed. The mixture was then warmed up to reflux temperature, stirred for 45 minutes and then slowly cooled down to room temperature. The white solid was collected by filtration and dried in vacuo. This material was recrystallised 4 times from THF (10 volumes) to give 32.5 g of a white solid. This material was then suspended in sodium hydroxide (1M solution, 400 mL) and Et$_2$O (400 mL) and allowed to stir at room temperature until complete dissolution. After separation of the two phases, the aqueous layer was extracted again with Et$_2$O (3×250 mL). Combined organic layers were washed with aqueous 1M sodium hydroxide solution (3×200 mL) and then dried over Na$_2$SO$_4$. Evaporation of solvent in vacuo gave the title compound (19 g) as white solid. The absolute configuration of the optical isomers was assigned as described in PCT International Publication WO2005/080382.

$^1$H-NMR (CDCl$_3$): δ 7.51 (d, 2H), 7.25 (d, 2H), 3.20 (d, 1H), 3.0-3.1 (m, 3H), 1.69 (m, 1H), 0.8-1.0 (m, 2H), NH not observed. MS (ES) (m/z): 228.1 [MH]$^+$.

Analytical Chromatography
Column: chiralcel OD 10 um, 250×4.6 mm
Mobile phase: A: n-Hexane; B: Isopropanol+0.1% Isopropyl amine
Gradient: isocratic 2% B
Flow rate: 1 mL/min
UV wavelength range: 200-400 nm
Analysis time 25 min
ret. time (min) % a/a
16.5  0.4  (1R,5S)-1-[4-(trifluoromethyl)phenyl]-3-azabicyclo[3.1.0]hexane
21.7  99.6  title compound Specific Optical Rotation: [α]$_D$=−10° (CDCl$_3$, T=20° C., c≅0.004 g/0.8 mL).

MS (ES) (m/z): 228 [MH]$^+$.

Preparation 5: (1S,5R)-3-(3-Chloropropyl)-1-[4-(trifluoromethyl)phenyl]-3-azabicyclo[3.1.0]hexane (Prep5)

To a solution of (1S,5R)-1-[4-(trifluoromethyl)phenyl]-3-azabicyclo[3.1.0]hexane (Prep4, 1.00 g) in dry THF (5 mL), DIPEA (2.4 mL) and 1-bromo-3-chloropropane (3.7 mL) were added and the resulting mixture was heated at reflux for 3 hours. After cooling at room temperature it was diluted with EtOAc (30 mL) washed twice with a saturated solution of NH$_4$Cl in water (20 mL) and once with a saturated aqueous NaHCO$_3$ solution (20 mL), dried over anhydrous Na$_2$SO$_4$ and concentrated under reduced pressure. The crude product was purified by silica gel chromatography eluting with cyclohexane/EtOAc 7:3 to give the title compound as a colourless oil (1.26 g).

NMR ($^1$H, CDCl$_3$): δ 7.50 (d, 2H) 7.19 (d, 2H), 3.59 (t, 2H), 3.33 (d, 1H), 3.09 (d, 1H), 2.58 (m, 2H), 2.66 (dd, 1H), 2.46 (dd, 1H), 1.92 (m, 2H), 1.74 (m, 1H), 1.67 (t, 1H), 0.81 (dd, 1H). MS (ES) (m/z): 304 [MH]$^+$.

Preparation 6:
3-Benzoyl-5-iodo-1H-pyrimidine-2,4-dione (Prep6)

A solution of 5-iodouracil (commercially available from Aldrich, 2 g, 8.4 mmol) in dry pyridine (20 mL) was added dropwise to a solution of benzoyl chloride (3.5 g, 25.3 mmol) in pyridine (10 mL). The mixture was stirred at room temperature for 3 hours. Water (70 mL) was added and the product extracted with ethyl acetate. The organic phase was washed with a saturated solution of NH$_4$Cl and then with 2% HCl$_{aq}$(40 mL×4 times) The solvent was removed under vacuum and the residue was triturated with i-Pr$_2$O to give the title compound as white solid (2.6 g).

MS (ES) (m/z): 343.2 [M+H]$^+$.

$^1$H-NMR (DMSO-d$_6$) δ: 11.90 (br. s., 1H), 8.13 (s, 1H), 7.95-8.01 (m, 2H), 7.75-7.82 (m, 1H), 7.57-7.63 (m, 2H)

Preparation 7: 3-Benzoyl-1-(3,3-dimethoxy-propyl)-5-iodo-1H-pyrimidine-2,4-dione (Prep7)

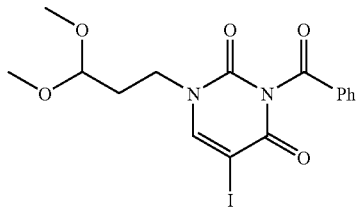

3-Benzoyl-5-iodo-1H-pyrimidine-2,4-dione (Prep 6, 2.1 g, 6.13 mmol), $K_2CO_3$ (846 mg, 6.13 mmol) and 3-bromo-1,1dimethoxy-propane (1 mL, 7.4 mmol) were dissolved in dry DMF under Nitrogen (8 mL). After stirring the reaction at room temperature for 48 h, water was added and the product extracted with diethylether. The organic phase was dried ($Na_2SO_4$) and evaporated. The crude was purified by flash chromatography with ethyl acetate-petroleum ether (35-65) to give 2.5 g of the title compound.

MS (ES) (m/z): 445.2 [M+H]$^+$.

Preparation 8: 3-(3-Benzoyl-5-iodo-2,4-dioxo-3,4-dihydro-2H-pyrimidin-1-yl)-propionaldehyde (Prep8)

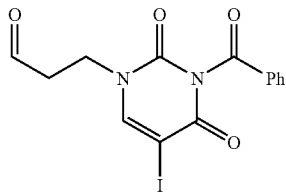

Method a

3-Benzoyl-1-(3,3-dimethoxy-propyl)-5-iodo-1H-pyrimidine-2,4-dione (Prep 7, 2.6 g, 5.63 mmol) was dissolved in dioxane (10 mL) and 1N $HCl_{aq}$ (22.5 mL) was added. The mixture was stirred at room temperature for 4.5 h. Water was added and the product extracted with ethyl acetate, the organic phase was washed with a 5% solution of $NaHCO_3$. The organic phase was dried ($Na_2SO_4$), evaporated and the crude was redissolved in dioxane (10 mL) and treated with a 2M solution of HCl. After work-up as above described, the crude was purified by flash chromatography with ethyl acetate-petroleum ether (3-7) to give the title compound as a white solid (1.48 g).

MS (ES) (m/z): 399.2 [M+H]$^+$.

$^1$H-NMR (DMSO-$d_6$) δ: 9.65 (d, 1H), 8.40 (s, 1H), 7.97-8.02 (m, 2H), 7.75-7.82 (m, 1H), 7.57-7.63 (m, 2H), 4.01 (t, 2H), 2.91 (td, 2H)

Method b

1-[3,3-bis(methyloxy)propyl]-5-iodo-3-(phenylcarbonyl)-2,4(1H,3H)-pyrimidinedione (5.77 g, 12.99 mmol) was dissolved in 1,4-dioxane (33 ml), then 1N $HCl_{aq}$ (26.0 ml, 26.0 mmol) was added and the mixture was stirred at 60° C. for 1 hour 30 minutes. 5 mL of 6N $HCl_{aq}$ (30 mmol) were added and the mixture was stirred at 60° C. After 2 hours further 5 mL of 6N $HCl_{aq}$ (30 mmol) were added and the solution stirred for further 1.5 hour (a white precipitate was formed). The reaction mixture was then concentrated under reduced pressure and partitioned between water and AcOEt. Organic phase was washed with a saturated solution of $NaHCO_3$, dried over $Na_2SO_4$ and solvent was eliminated under reduced pressure giving the title compound (4.85 g, 12.20 mmol) as a white solid.

MS (ES) (m/z): 398.95 [M+H]$^+$.

$^1$H-NMR (DMSO-$d_6$) δ: 9.65 (s, 1H), 8.42 (s, 1H), 8.05 (d, 2H), 7.78-7.82 (m, 1H), 7.59-7.63 (m, 2H), 4.02 (t, 2H), 2.92 (t, 2H)

Preparation 9: 3-Benzoyl-5-iodo-1-{3-[(1S,5R)-1-(4-trifluoromethyl-phenyl)-3-aza-bicyclo[3.1.0]hex-3-yl]-propyl}-1H-pyrimidine-2,4-dione (Prep9)

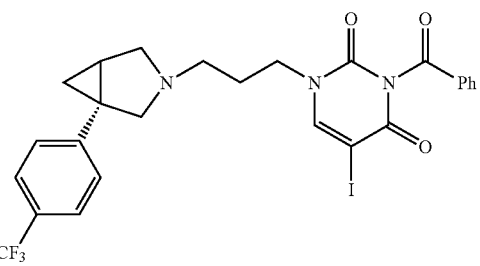

To a solution of 3-(3-benzoyl-5-iodo-2,4-dioxo-3,4-dihydro-2H-pyrimidin-1-yl)-propionaldehyde (Prep 8, 700 mg, 1.7 mmol) in dichloromethane (20 mL), (1S,5R)-1-(4-trifluoromethyl-phenyl)-3-aza-bicyclo[3.1.0]hexane (Prep 4, 399 mg, 1.7 mmol), AcOH (158 mg, 2.5 mmol) and $NaBH(AcO)_3$ (410 mg, 1.9 mmol) were added at 0° C. The mixture was stirred at 0° C. for further 1 hour. Water was added and the solvent was evaporated under vacuum, the residue re-dissolved in ethyl acetate and the mixture washed with a 5% solution of aqueous $NaHCO_3$. The organic phase was dried ($Na_2SO_4$) and evaporated. The crude was purified by flash chromatography with DCM-MeOH—$NH_4OH$ (97-3-1) to give the title compound as a white solid (880 mg).

MS (ES) (m/z): 610.2 [M+H]$^+$.

$^1$H-NMR (DMSO-$d_6$) δ: 8.42 (s, 1H), 7.92-8.01 (m, 2H), 7.73-7.83 (m, 1H), 7.56-7.67 (m, 4H), 7.30-7.39 (m, 2H), 3.83 (t, 2H), 3.33-3.49 (m, 2H), 3.06 (d, 1H), 2.54 (t, 2H), 2.41 (dd, 1H), 1.93 (dt, 1H), 1.76-1.87 (m, 2H), 1.43 (dd, 1H), 0.87 (dd, 1H)

Preparation 10: 5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep10)

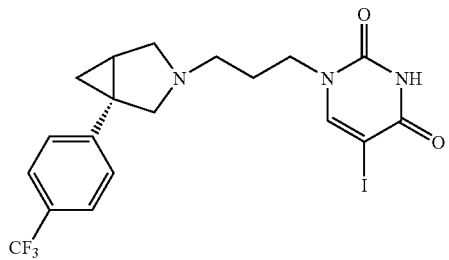

3-Benzoyl-5-iodo-1-{3-[(1S,5R)-1-(4-trifluoromethyl-phenyl)-3-aza-bicyclo[3.1.0]hex-3-yl]-propyl}-1H-pyrimidine-2,4-dione (Prep 9, 840 mg, 1.38 mmol) was dissolved in 10% NH$_3$ in MeOH solution (5 mL). The mixture was stirred at room temperature for 1 hour, the solvent was then evaporated under vacuum and the crude purified by flash chromatography with DCM-MeOH—NH$_4$OH (98-2-1) to give the title compound as a white solid (515 mg).

MS (ES) (m/z): 506.3 [M+H]$^+$.

$^1$H-NMR (DMSO-d$_6$) δ: 11.56 (s, 1H), 8.16 (s, 1H), 7.58-7.65 (m, 2H), 7.30-7.37 (m, 2H), 3.73 (t, 2H), 3.34 (d, 1H), 3.02 (d, 1H), 2.51-2.54 (m, 1H), 2.46 (t, 2H), 2.38 (dd, 1H), 1.91 (ddd, 1H), 1.70-1.82 (m, 2H), 1.42 (dd, 1H), 0.85 (dd, 1H)

Preparation 11: [1-methyl-3-(trifluoromethyl)-1H-pyrazol-4-yl]boronic acid and [1-methyl-3-(trifluoromethyl)-1H-pyrazol-5-yl]boronic acid (Prep11)

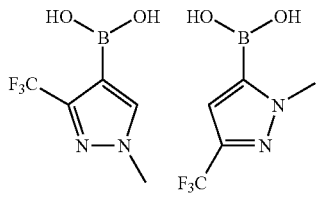

To a stirred solution of 4-bromo-1-methyl-3-(trifluoromethyl)-1H-pyrazole (100 mg, 0.437 mmol) in Tetrahydrofuran (THF) at −78° C., a solution of BuLi 1.6M in hexane (328 µl, 0.524 mmol) was added drop wise. Mixture was stirred at −78° C. for 1 h, then 4,4,5,5-tetramethyl-2-[(1-methylethyl)oxy]-1,3,2-dioxaborolane (134 µl, 0.655 mmol) was added maintaining the temperature below −75° C. Mixture was allowed to warm slowly to r.t. within overnight. Half of the mixture was concentrated under reduced pressure.

THF was removed form the remaining half of the mixture under reduced pressure, the residue was diluted by DCM/water (5+5 mL), the organic layer separated by separation tube and solvent removed under reduced pressure.

The two batches obtained were combined to give title compound as a mixture of stereoisomers. Crude was used without any further purification in the following step.

MS (ES) (m/z): 195.2 [MH]$^+$.

Preparation 12: 2,4-bis(methyloxy)-5-(5-methyl-1,3,4-thiadiazol-2-yl)pyrimidine (Prep 12)

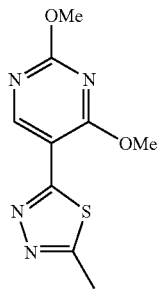

In a microwave vial, 2-bromo-5-methyl-1,3,4-thiadiazole (0.6 g, 3.26 mmol), [2,4-bis(methyloxy)-5-pyrimidinyl]boronic acid (0.780 g, 4.36 mmol) and tetrakis(triphenylphosphine)palladium(0) (0.754 g, 0.652 mmol) in 1,2-Dimethoxyethane (DME) (12 ml) were stirred until dissolution of reactants, then sodium carbonate 1M (9.78 ml, 9.78 mmol) was added and the mixture microwaved for 10 min at 150° C.

In another microwave vial, 2-bromo-5-methyl-1,3,4-thiadiazole (commercially available from Akos, 0.522 g, 2.84 mmol), [2,4-bis(methyloxy)-5-pyrimidinyl]boronic acid (0.780 g, 4.36 mmol) and tetrakis(triphenylphosphine)palladium(0) (0.656 g, 0.568 mmol) in 1,2-Dimethoxyethane (DME) (12 ml) were stirred until dissolution of reactants, then sodium carbonate 1M (8.51 ml, 8.51 mmol) was added and the mixture microwaved for 10 min at 150° C.

The two reaction mixtures were combined, water and AcOEt (50+50 mL) were added and organic layer separated. Combined organic layers were washed by water (3×50 mL), dried upon sodium sulphate and concentrated under reduced pressure. Residue was purified by flash chromatography (Cy: EtOAc 1:1) to give the title compound (637 mg, 2.272 mmol).

$^1$H NMR (CHLOROFORM-d) δ ppm 9.30 (s, 1H) 4.18 (s, 3H) 4.11 (s, 3H) 2.84 (s, 3H)

Preparation 13: 5-(5-methyl-1,3,4-thiadiazol-2-yl)-2,4(1H,3H)-pyrimidinedione (Prep 13)

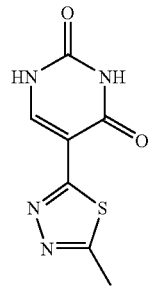

2,4-bis(methyloxy)-5-(5-methyl-1,3,4-thiadiazol-2-yl)pyrimidine (Prep. 12, 311 mg, 1.305 mmol) was suspended in hydrochloric acid 4M in dioxane (4 ml, 16.00 mmol) and the mixture stirred at 90° C. for 4 h. Solvent was removed under reduced pressure, to give title compound (334 mg, 1.303 mmol). Crude was used in the following step without any further purification.

MS (ES) (m/z): 211.05 [M+H]$^+$.

Preparation 14: 5-(4,5-dimethyl-1,3-thiazol-2-yl)-2,4-bis(methyloxy)pyrimidine (Prep 14)

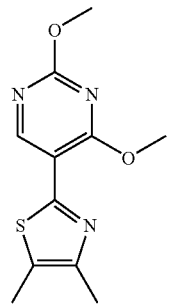

2-iodo-4,5-dimethyl-1,3-thiazole (prepared in a similar manner to that described in JACS 123 (6), 1017-1022, (2001), 250 mg, 1.046 mmol) was dissolved in 1,2-Dimethoxyethane (DME) (4.357 ml). Tetrakis(triphenylphosphine)palladium (0) (60.4 mg, 0.052 mmol) was added and the mixture was stirred at room temperature for 10 minutes. Sodium bicarbonate (4.183 ml, 4.18 mmol) and [2,4-bis(methyloxy)-5-pyrimidinyl]boronic acid (385 mg, 2.091 mmol) were added and the resulting mixture was stirred at 85° C. for 2 hours. The mixture was allowed to cool to rt and left standing at rt over the week end. The mixture was diluted with DCM (5 mL), the aqueous phases was separated and extracted with DCM (2×5 mL). The organics were combined and dried over sodium sulphate to give a yellow solid that was purified by silica chromatography, eluting with DCM:MeOH from 100:0 to 95:5 to afford the title compound as a pale yellow solid (143 mg).

MS (ES) (m/z): 252 [M+H]$^+$.

Preparation 15: 5-(4,5-dimethyl-1,3-thiazol-2-yl)-2,4 (1H,3H)-pyrimidinedione (Prep 15)

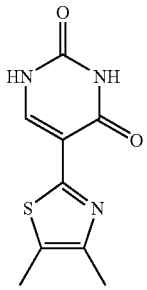

(5-(4,5-dimethyl-1,3-thiazol-2-yl)-2,4-bis(methyloxy)pyrimidine) (Prep14, 118 mg, 0.470 mmol) in HCl (5.87 ml, 23.48 mmol) 4M in dioxane was stirred in a closed tube at 90° C. for 1.5 hour. Then the mixture was cooled to rt and the solvent evaporated under vacuum to afford the title compound as a pale grey solid (153 mg)

MS (ES) (m/z): 224 [M+H]$^+$.

Preparation 16: 5-(4,5-dimethyl-1,3-thiazol-2-yl)-3-(phenylcarbonyl)-2,4(1H,3H)-pyrimidinedione (Prep 16)

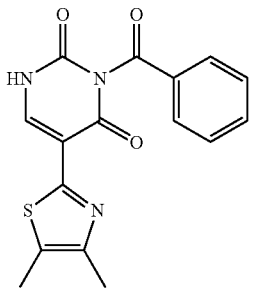

(5-(4,5-dimethyl-1,3-thiazol-2-yl)-2,4(1H,3H)-pyrimidinedione) (Prep 15, 100 mg) suspended in Pyridine (2 mL) was slowly added to a stirring solution of benzoyl chloride (0.156 ml, 1.344 mmol) in Pyridine (1 mL) under nitrogen atmosphere. The resulting yellow solution was stirred at rt for 5.5 hours. Water was added (3 mL) and the mixture was extracted with EtOAc (10 mL). The organic was washed with NH$_4$Cl saturated aqueous solution (2×2 mL) dried (Na$_2$SO$_4$, vacuo) to afford 340 mg of a yellowish solid that was dissolved in EtOAc (30 mL) and washed with NaHCO$_3$ aqueous saturated solution. The organic was dried (Na$_2$SO$_4$, vacuo) to afford the title compound as a yellowish solid (180 mg)

MS (ES) (m/z): 328 [M+H]$^+$.

Preparation 17: 1-[3,3-bis(methyloxy)propyl]-5-(4,5-dimethyl-1,3-thiazol-2-yl)-3-(phenylcarbonyl)-2,4 (1H,3H)-pyrimidinedione (Prep 17)

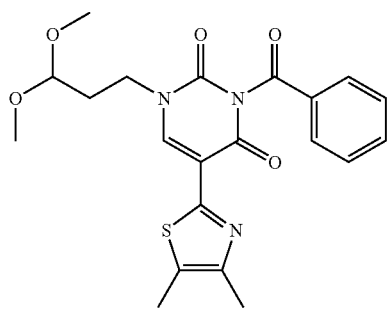

5-(4,5-dimethyl-1,3-thiazol-2-yl)-3-(phenylcarbonyl)-2,4 (1H,3H)-pyrimidinedione (Prep 16, 80 mg, 0.244 mmol), K$_2$CO$_3$ (33.8 mg, 0.244 mmol), TBAI (9.03 mg, 0.024 mmol) and 3-bromo-1,1-bis(methyloxy)propane (0.033 mL, 0.244 mmol) in dry N,N-Dimethylformamide (DMF) (1.5 mL) were stirred in a closed vial at rt for 2 days then it was left standing at rt over the weekend. The mixture was diluted with EtOAc (20 mL) and washed with small portion of ice-water (3×1 mL). The organic was dried (Na$_2$SO$_4$, rotaevaporator) to afford a crude (95 mg) that was purified by silica chromatography, eluting with Cyclohexane:EtOAc 100:0 to 50:50 to afford the title compound as a white solid (42 mg).

MS (ES) (m/z): 430 [M+H]$^+$.

$^1$H NMR (400 MHz, CHLOROFORM-d) δ ppm 2.09-2.17 (m, 2H) 2.37 (s, 6H) 3.37 (s, 6H) 4.02 (t, 2H) 4.50 (t, 1H) 7.48-7.57 (m, 2H) 7.64-7.72 (m, 1H) 7.94-8.01 (m, 2H) 8.46 (s, 1H)

Preparation 18:
2,4-bis(methyloxy)-5-pyrimidinecarboxylic acid (Prep 18)

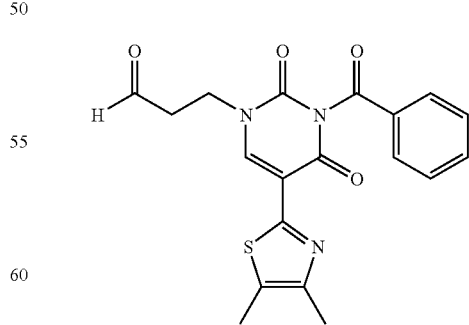

1-[3,3-bis(methyloxy)propyl]-5-(4,5-dimethyl-1,3-thiazol-2-yl)-3-(phenylcarbonyl)-2,4(1H,3H)-pyrimidinedione (Prep17, 42 mg, 0.098 mmol) was dissolved in dry Tetrahydrofuran (THF) (2 mL). Aqueous 2M Hydrochloric acid (0.112 mL, 0.225 mmol) was added and the mixture was stirred at rt overnight. Aqueous 2M Hydrochloric acid (0.02 mL) was added and the mixture was stirred at rt for other 7 hrs.

The mixture was dried (rotaevaporator, cold bath) to afford a pale yellow solid that was used without further processing in the next reaction step considering a quantitative conversion (0.098 mmol) to target material and corresponding emiacetal by LCMS.

MS (ES) (m/z): 384, 416 [M+H]+.

Preparation 19: 2,4-bis(methyloxy)-5-(2-methyl-1,3-thiazol-4-yl)pyrimidine (Prep19)

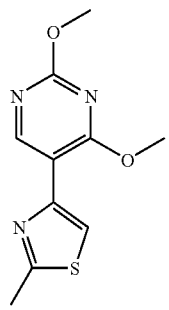

4-bromo-2-methyl-1,3-thiazole (commercially available from Frontier, 300 mg, 1.685 mmol) was dissolved in 1,2-Dimethoxyethane (DME) (5 ml). Pd(Ph$_3$)$_4$ (97 mg, 0.084 mmol) was added and the reaction mixture was stirred at room temperature for 15 min. [2,4-bis(methyloxy)-5-pyrimidinyl]boronic acid (commercially available from Aldrich, 651 mg, 3.54 mmol) and 1M/H$_2$O sol. of NaHCO$_3$ (4.60 ml, 4.60 mmol) were added thereto. The reaction mixture was heated at 90° C. for 2.5 h and left at room temperature overnight. The mixture was then diluted with dichloromethane (20 ml) and washed with water (20 ml). The organic layer was separated through an hydrophobic frit and concentrated. The obtained crude was purified by flash chromatography eluting with Cyclohexane/AcOEt 8/2. 290 mg of the title compound were isolated as a white solid.

MS (ES) (m/z): 238.1 [M+H]+, 260.1 [M+Na]+

Preparation 20: 5-(2-methyl-1,3-thiazol-4-yl)-2,4 (1H,3H)-pyrimidinedione hydrochloride (Prep20)

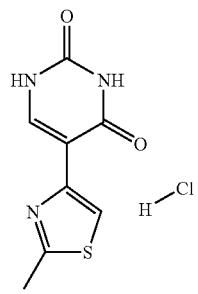

2,4-bis(methyloxy)-5-(2-methyl-1,3-thiazol-4-yl)pyrimidine (Prep19, 290 mg, 1.222 mmol) was suspended in HCl 4M in 1,4-dioxane (10 ml). The reaction mixture was heated at 90° for 1 h and left at room temperature overnight. The solvent was then removed in vacuo to give the title compound as a solid (287 mg).

MS (ES) (m/z): 210.0.

Prep 21: 1-[3,3-bis(methyloxy)propyl]-5-(2-methyl-1,3-thiazol-4-yl)-2,4(1H,3H)-pyrimidinedione (Prep21)

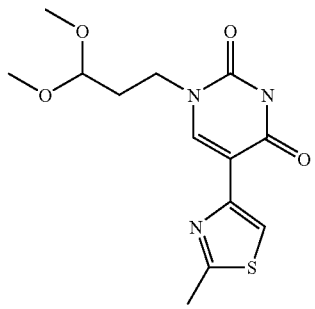

5-(2-methyl-1,3-thiazol-4-yl)-2,4(1H,3H)-pyrimidinedione hydrochloride (Prep20, 287 mg, 1.110 mmol) was dissolved in N,N-Dimethylformamide (DMF) (4 ml). K$_2$CO$_3$ (460 mg, 3.33 mmol) were added and the reaction mixture stirred at room temperature for 1 h. 3-bromo-1,1-bis(methyloxy)propane (0.185 ml, 1.221 mmol) was added. The obtained mixture was then stirred at room temperature. After 4 days it was diluted with water, neutralized with HCl, and extracted by EtOAc. The organic phase was washed with water (3 times), brine, dried over Na$_2$SO$_4$, filtered and the solvent evaporated. The obtained crude was purified by preparative LC-MS. 58.5 mg of the title compound were isolated as a white solid.

[Preparative LC-MS conditions: Column: WATERS XTerra prep MS C18 OBD, 30×150 mm, 10 μm; Mobile phase: A: NH$_4$HCO$_3$ sol. 10 mM, pH 10; B: CH$_3$CN; Gradient: 1% (B) for 1 min, 1% to 50% (B) in 9 min, 50% to 99% (B) in 6 min, 99% (B) for 2 min. Flow rate: 40 ml/min; UV range: 210-400 nm; Ionization: ES+/ES−; Mass range: 130-900 amu].

MS (ES) (m/z): 312.06 [M+H]+.

Preparation 22:
5-(4-isothiazolyl)-2,4-bis(methyloxy)pyrimidine (Prep22)

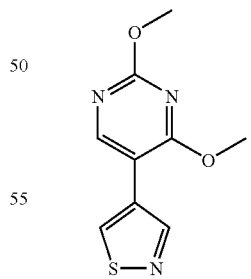

4-bromoisothiazole (commercially available from Aurora, 500 mg, 3.05 mmol) was dissolved in degassed 1,2-Dimethoxyethane (DME) (5 ml). Pd(Ph$_3$)$_4$ (176 mg, 0.152 mmol) was added thereto. The reaction mixture was stirred at room temperature for 15 min. [2,4-bis(methyloxy)-5-pyrimidinyl]boronic acid (commercially available from Aldrich, 1178 mg, 6.40 mmol) and 5 mL of degassed 1M/H$_2$O solution of NaHCO3 were added to the reaction mixture under N2 atm. After 2 h 30 min stirring at 90° C. the mixture was diluted with water and extracted with DCM. The collected organic phases were evaporated. The residue was purified by flash chromatography eluting with cyclohexane/EtOAc 5:1. 686 mg of the title compound were isolated as a yellow solid.

MS (ES) (m/z): 224.06 [M+H]⁺.

Preparation 23: 5-(4-isothiazolyl)-2,4(1H,3H)-pyrimidinedione hydrochloride (Prep 23)

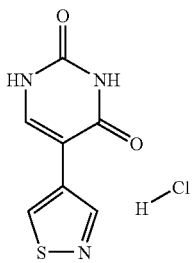

5-(4-isothiazolyl)-2,4-bis(methyloxy)pyrimidine (Prep22, 686 mg, 2.427 mmol) was suspended in 4M HCl solution in 1,4-dioxane (25 ml). After 1 h at 90° C., the solvent was evaporated. 696.8 mg of the title compound were isolated as a yellow solid.

MS (ES) (m/z): 196.06.

Preparation 24: 1-[3,3-bis(methyloxy)propyl]-5-(4-isothiazolyl)-2,4(1H,3H)-pyrimidinedione (Prep 24)

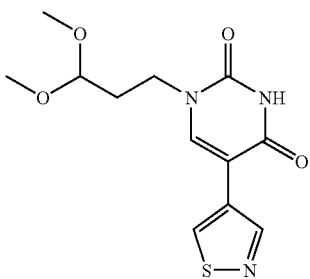

5-(4-isothiazolyl)-2,4(1H,3H)-pyrimidinedione hydrochloride (Prep23, 300 mg, 1.036 mmol) was dissolved in N,N-Dimethylformamide (DMF) (4 ml) to give a pale yellow suspension. $K_2CO_3$ (215 mg, 1.554 mmol) was added ant the reaction mixture was stirred at room temperature for 1 h. 3-bromo-1,1-bis(methyloxy)propane (0.173 ml, 1.140 mmol) was added. Mixture was stirred at room temperature for 3 days, then diluted with water, acidified with diluted HCl until pH ~5, and extracted with EtOAc. The organic phase was washed with water (3 times), brine, dried over $Na_2SO_4$, filtered and the solvent evaporated. The obtained residue was purified by flash chromatography eluting with cyclohexane/EtOAc 1:1. Obtained 60 mg (13.44% yield) of a 9:1 mixture of the title compound and the corresponding bis alkylated derivative.

MS (ES) (m/z): 298.03 [M+H]⁺.

Preparation 25: 2,4-bis(methyloxy)-5-(1,3-thiazol-2-yl)pyrimidine (Prep 25)

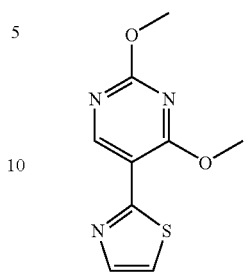

2-bromo-1,3-thiazole (commercially available from Aldrich, 0.165 ml, 1.829 mmol) was dissolved in degassed 1,2-Dimethoxyethane (DME) (5 ml). Pd(Ph₃)₄ (106 mg, 0.091 mmol) was added. The reaction mixture was stirred at room temperature for 15 min. [2,4-bis(methyloxy)-5-pyrimidinyl] boronic acid (commercially available from Aldrich, 707 mg, 3.84 mmol) and 5 mL of degassed 1M aqueous solution of $NaHCO_3$ were added to the reaction mixture under $N_2$ atmosphere. After 2 h 30 min stirring at 90° C., the reaction mixture was diluted with water and extracted with DCM. The collected organic phases were evaporated. The residue was purified by flash chromatography eluting with cyclohexane/EtOAc 5:1. 294 mg of the title compound were isolated as a yellow solid.

MS (ES) (m/z): 224.06 [M+H]⁺.

Preparation 26: 5-(1,3-thiazol-2-yl)-2,4(1H,3H)-pyrimidinedione hydrochloride (Prep26)

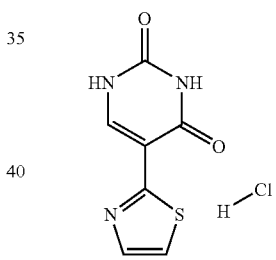

2,4-bis(methyloxy)-5-(1,3-thiazol-2-yl)pyrimidine (Prep25, 294 mg, 1.225 mmol) was suspended in 4M HCl solution in 1,4-dioxane (25 ml) to give a white suspension. After 1 h at 90° C., the solvent was evaporated. 306.8 mg of the title compound were isolated as a white solid.

MS (ES) (m/z): 196.06.

Preparation 27: 1-[3,3-bis(methyloxy)propyl]-5-(1,3-thiazol-2-yl)-2,4(1H,3H)-pyrimidinedione (Prep27)

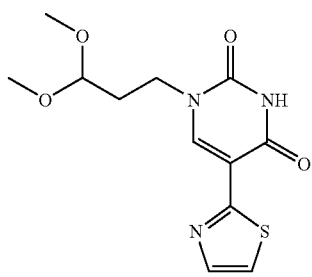

5-(1,3-thiazol-2-yl)-2,4(1H,3H)-pyrimidinedione hydrochloride (Prep26, 287 mg, 1.202 mmol) was dissolved in N,N-Dimethylformamide (DMF) (3 ml) to give a pale yellow solution. K₂CO₃ (249 mg, 1.803 mmol) was added followed by 3-bromo-1,1-bis(methyloxy)propane (0.200 ml, 1.322 mmol). After 4 days stirring at room temperature the reaction mixture was diluted with water and extracted with EtOAc. The organic phase was washed with water (3 times), brine, dried over Na₂SO₄, filtered and the solvent evaporated. The obtained residue was purified by flash chromatography eluting with cyclohexane/EtOAc 1:1. 33.9 mg of a white solid were obtained consisting of a 7:3 mixture of the title compound and the corresponding bis alkylated derivative.

MS (ES) (m/z): 298.03 [M+H]⁺.

Preparation 28: 2,4-bis-(methyloxy)-5-(1-methyl-1H-pyrazol-4-yl)pyrimidine (Prep28)

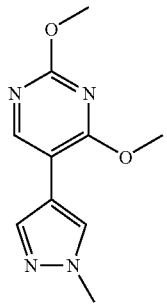

5-bromo-2,4-bis(methyloxy)pyrimidine (commercially available from Aldrich, 500 mg, 2.283 mmol) was dissolved in 1,2-Dimethoxyethane (DME) (5 ml). Pd(Ph₃)₄ (132 mg, 0.114 mmol) was added and the reaction mixture was stirred at room temperature for 15 min. 1-methyl-4-(4,4,5,5-tetramethyl-1,3,2-dioxaborolan-2-yl)-1H-pyrazole (commercially available from Maybridge, 997 mg, 4.79 mmol) and 1M/H₂O sol. of NaHCO₃ (5 ml, 5.00 mmol) were added. After 2 h stirring at 90° C., the reaction mixture was cooled at room temperature, diluted with water (5 ml) and extracted with DCM (3×10 ml). The obtained residue was purified by flash chromatography first eluting with cyclohexane/EtOAc 4:1 then with 1:2 cyclohexane/EtOAc. 483.7 mg of the title compound were obtained.

MS (ES) (m/z): 221.10 [M+H]⁺.

Preparation 29: 5-(1-methyl-1H-pyrazol-4-yl)-2,4(1H,3H)-pyrimidinedione hydrochloride (Prep29)

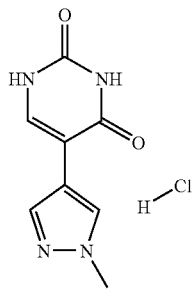

2,4-bis(methyloxy)-5-(1-methyl-1H-pyrazol-4-yl)pyrimidine (Prep28, 483.7 mg, 1.977 mmol) was suspended in 4M solution of HCl in 1,4-dioxane (10 mL, 40.0 mmol) to give a white suspension. After 1 h at 90° C., 5 ml of 4M solution of HCl in 1,4-dioxane (5 mL, 20.0 mmol) were then added and the reaction mixture was vigorously stirred at 90° C. Again, 5 ml of 4M solution of HCl in 1,4-dioxane (5 mL, 20.0 mmol) were added and the reaction mixture was vigorously stirred at 90° C. overnight. The solvent was evaporated to obtain 508.4 mg of the title compound as a white solid.

MS (ES) (m/z): 193.11.

Preparation 30: 1-[3,3-bis(methyloxy)propyl]-5-(1-methyl-1H-pyrazol-4-yl)-2,4(1H,3H)-pyrimidinedione (Prep30)

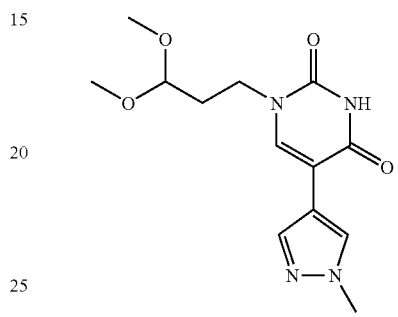

5-(1-methyl-1H-pyrazol-4-yl)-2,4(1H,3H)-pyrimidinedione hydrochloride (Prep29, 250 mg, 0.962 mmol) was dissolved in N,N-Dimethylformamide (DMF) (4 ml) to give a pale yellow solution. K₂CO₃ (270 mg, 1.954 mmol) and 3-bromo-1,1-bis(methyloxy)propane (0.220 ml, 1.451 mmol) were added. After 4 days stirring at room temperature, the reaction mixture was diluted with water and extracted with EtOAc. The organic phase was washed with water (3 times), brine, dried over Na₂SO₄, filtered and the solvent evaporated. 110.6 mg of a pale yellow solid were obtained.

The aqueous phase was acidified with HCl until pH ~5 and extracted again with EtOAc (3 times). The combined organic phases were washed brine, dried over Na₂SO₄, filtered and the solvent evaporated. 108.2 mg of a pale yellow syrupy oil were obtained.

This oil and the previously obtained yellow solid were mixed together and purified by preparative LC-MS. 33.9 mg of the title compound were obtained as white solid.

[Preparative LC-MS conditions: Column: WATERS XTerra prep MS C18 OBD, 30×150 mm, 10 μm; Mobile phase: A: NH₄HCO₃ sol. 10 mM, pH 10; B: CH₃CN; Gradient: 10% (B) for 1 min, 10% to 95% (B) in 12.5 min, 95% to 100% (B) in 3 min. Flow rate: 40 ml/min; UV range: 210-400 nm; Ionization: ES+/ES−; Mass range: 130-900 amu].

MS (ES⁻) (m/z): 293.04 [M−H]⁻.

Preparation 31: 2,4-bis(methyloxy)-5-pyrimidinecarboxylic acid (Prep31)

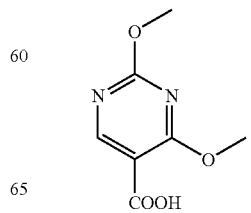

To a solution of 2,4-Bis(methyloxy)-5-pyrimidinecarbaldehyde (commercially available from Toronto, 1.400 g, 8.33 mmol) at 0° C. in t-Butanol (14.00 mL) an aqueous solution (7 mL) of Sodium chlorite (1.807 g, 19.98 mmol) was added over 25 min and sodium dihydrogen phosphate hydrate (3.64 g, 23.33 mmol). The yellow mixture obtained was warmed to 25° C. and after 6 h 14 mL of t-Butanol, 7 mL of water, and Sodium chlorite (2.26 g, 25 mmol) were added. The reaction mixture was stirred at room temperature overnight. After 24 h, the mixture was evaporated in vacuo, and the crude material purified by SPE 25 g cartridge eluting with DCM/MeOH 8:2 to recover 1 g of title compound.

MS (ES) (m/z): 185.2 [M+H]$^+$.

Preparation 32: methyl 2,4-bis(methyloxy)-5-pyrimidinecarboxylate (Prep32)

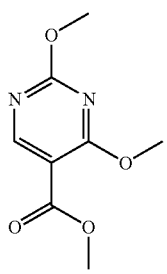

To a suspension of 2,4-Bis(methyloxy)-5-pyrimidinecarboxylic acid (Prep31, 1.000 g, 5.43 mmol) in N,N-Dimethylformamide (DMF) (35 mL) at 0° C. N,N'-Carbonyldiimidazole (1.321 g, 8.15 mmol) was added and the mixture was stirred for 1 hour at 0° C., then left stirring at rt. After 4 h Triethylamine (2.271 mL, 16.29 mmol) and N,N'-Carbonyldiimidazole (1.321 g, 8.15 mmol), were added to the white suspension. After other 4 h, N,N'-Carbonyldiimidazole (1.321 g, 8.15 mmol) of another batch was added to the suspension. The reaction was left overnight at rt. The solution was then concentrated in vacuo and methanol was added. The solution was stirred at reflux for 2 h. Then the mixture was evaporated in vacuo, the residue was dissolved in DCM and washed with NaHCO$_3$ sat. sol. and then with H$_2$O. Organic phase was dried with Na$_2$SO$_4$ anhydrous, filtered and evaporated in vacuo to obtain 550 mg of the title compound, which was used in the following step without further purification.

MS (ES) (m/z): 199.2 [M+H]$^+$.

Preparation 33: 5-(3-methyl-1,2,4-oxadiazol-5-yl)-2,4(1H,3H)-pyrimidinedione (Prep33)

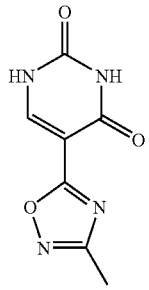

To a suspension of Sodium hydride (120 mg, 3.00 mmol) in THF (15 mL) activated molecular sieves (0.3 nm, beads about 2 mm) were added. Then, N-hydroxyethanimidamide (commercially available from ABCR, 222 mg, 3.00 mmol) dissolved in THF (8 mL) was added.

After 15 min. Methyl 2,4-bis(methyloxy)-5-pyrimidinecarboxylate (Prep32, 540 mg, 2.72 mmol) dissolved in THF (12 mL) was added. After 10 min. N,N-Dimethylformamide (DMF) (7.00 mL) was added and the reaction mixture was stirred at 60° C. for 4 h. The reaction mixture was filtered and concentrated under reduced pressure to obtain a red oil (195 mg). The residue was dissolved in HCl 4M in dioxane (15 mL, 60 mmol) and heated at 90 C for 2 h. Solvents were evaporated under vacuum to obtain 170 mg of the title compound as brown solid.

MS (ES) (m/z): 196.12 [M+H]$^+$.

Preparation 34: 5-(2,4-dimethyl-1,3-thiazol-5-yl)-2,4(1H,3H)-pyrimidinedione (Prep34)

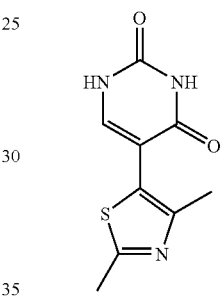

Step a:

To a solution of 4-bromo-2,5-dimethyl-1,3-thiazole (commercially available from Apollo Scientific Ltd, 410 mg, 2.135 mmol) in 1,2-Dimethoxyethane (DME) (6.5 mL), Tetrakis(triphenylphosphine)palladium (123 mg, 0.107 mmol) was added and the mixture was stirred at rt for 30 minutes. Then [2,4-bis(methyloxy)-5-pyrimidinyl]boronic acid (commercially available from Aldrich, 916 mg, 4.48 mmol) and 1M Sodium bicarbonate aqueous solution (5.83 mL, 5.83 mmol) were added. The reaction mixture was then stirred at 90° C. for 2.5 h and left stirring at rt overnight. The day after the mixture was diluted with DCM and washed with water. Organic layer was dried and concentrated under vacuum. Crude product was first purified by flash chromatography (eluent: Cy/AcOEt 65:35) and further purified by SCX cartridge affording 5-(2,5-dimethyl-1,3-thiazol-4-yl)-2,4-bis(methyloxy)pyrimidine with minor unknown impurities that was used in the next step without further purification.

Step b:

5-(2,4-dimethyl-1,3-thiazol-5-yl)-2,4-bis(methyloxy)pyrimidine (521 mg, 2.073 mmol) was dissolved in Methanol (30 ml), then 1N Hydrochloric acid aqueous solution (16.59 ml, 16.59 mmol) was added and the mixture was refluxed for 3 hours. Solvents were then evaporated under reduced pressure, the residue was triturated with acetone and filtered providing the title compound (507 mg, 2.27 mmol) as a white solid.

MS (ES) (m/z): 224.09 [M+H]$^+$.

Preparation 35: 1-[3,3-bis(methyloxy)propyl]-5-(2,4-dimethyl-1,3-thiazol-5-yl)-2,4(1H,3H)-pyrimidinedione (Prep35)

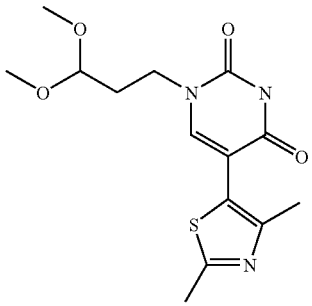

To a suspension of 5-(2,4-dimethyl-1,3-thiazol-5-yl)-2,4 (1H,3H)-pyrimidinedione (Prep34, 250 mg, 1.120 mmol) in N,N-Dimethylformamide (DMF) (4 mL), Potassium carbonate (124 mg, 0.896 mmol) was added and the mixture was stirred at rt for 1 hour. Afterwards 3-bromo-1,1-bis(methyloxy)propane (0.170 mL, 1.120 mmol) was added dropwise and the reaction mixture was stirred at rt overnight. The day after the reaction was quenched with water and extracted with AcOEt. Organic phase was dried over $Na_2SO_4$ and concentrated under vacuum providing a crude as a clear oil. The latter was purified by flash chromatography (eluent:DCM/MeOH/NH3 97:3:0.1) affording the title compound (155 mg, 0.429 mmol) as a white solid.

MS (ES) (m/z): 326.09 $[M+H]^+$.

Preparation 36: 3-[5-(2,4-dimethyl-1,3-thiazol-5-yl)-2,4-dioxo-3,4-dihydro-1(2H)-pyrimidinyl]propanal (Prep36)

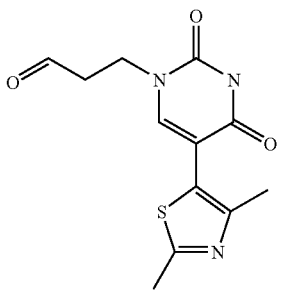

1-[3,3-bis(methyloxy)propyl]-5-(2,4-dimethyl-1,3-thiazol-5-yl)-2,4(1H,3H)-pyrimidinedione (Prep35, 321 mg, 0.987 mmol) was dissolved in Tetrahydrofuran (THF) (20 mL), 1N Hydrochloric acid aqueous solution (5.92 mL, 5.92 mmol) was added and the mixture was stirred at 45° C. for 1.5 hours. Volatiles were evaporated under vacuum (cold bath) then triethylamine (0.825 mL, 5.92 mmol) and THF (6 mL) were added. Solvents were eliminated until dryness and the white foam thus obtained was used in the next step without further purification.

MS (ES) (m/z): 280.1 $[M+H]^+$.

Preparation 37: 1-(4-chlorobutyl)-5-(2,4-dimethyl-1,3-thiazol-5-yl)-2,4(1H,3H)-pyrimidinedione (Prep37)

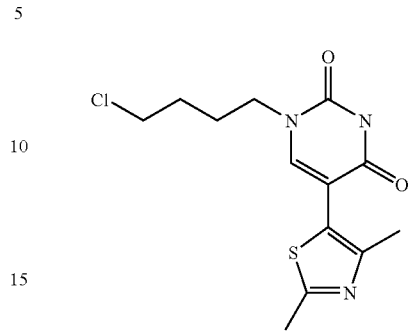

To a suspension of 5-(2,4-dimethyl-1,3-thiazol-5-yl)-2,4 (1H,3H)-pyrimidinedione (Prep34, 227 mg, 1.017 mmol) in N,N-Dimethylformamide (DMF) (4 mL), Potassium carbonate (112 mg, 0.813 mmol) was added and the mixture was stirred at rt for 20 minutes.

Afterwards 1-bromo-4-chlorobutane (0.141 mL, 1.220 mmol) was added and the reaction mixture was stirred at rt overnight. The day after reaction mixture was quenched with water and extracted with AcOEt. Organic phase was washed with water and brine, dried over $Na_2SO_4$ and concentrated under reduced pressure. Crude product was purified by flash chromatography (eluent: DCM to DCM/MeOH/NH3 95:5: 0.1) affording the title compound (108 mg, 0.310 mmol) as a clear oil.

MS (ES) (m/z): 314.02 $[M+H]^+$.

Preparation 38: (5,6-dihydro-2H-pyran-3-yloxy)(trimethyl)silane (Prep38)

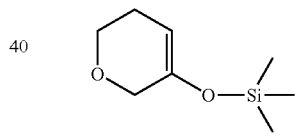

To a stirred solution of the dihydro-2H-pyran-3(4H)-one (commercially available from Pharm lab Product list, 21.6 g, 0.216 mol) in 160 ml of dry THF, trimethyl silyl chloride (58.7 g, 68.5 ml, 0.54 mol) was added under argon at room temperature, then the mixture was allowed to stir 10 minutes.

At this mixture triethylamine (59.7 g, 82.2 ml, 0.59 mol) was added dropwise and under vigorous stirring (strong precipitation). The resulting suspension was heated to reflux for 48 hours, then the mix was cooled to r.t and concentrated to ⅓ of the volume at the rotavapor (T=40° C., p=200 mbar). At this crude 300 ml of pentane were added to allow the complete precipitation of TEA.HCl and the suspension was filtered.

The solid was washed with 100 ml of pentane and the resulting filtrate was separated.

The desired product was isolated by fract. Distillation; pentane and THF residue were removed at athmospheric pressure and the sililenolether was isolated at Tdist=58-60° C. p=5 mbar. Obtained 28.7 g of the title compound as colourless oil MS (ES) (m/z): 172 $[M+H]^+$ $^1$H NMR (CDCl$_3$): δ 0.20 (s, 9H), 1.92-2.32 (m, 2H), 3.67 (t, J=5.5 Hz, 2H), 3.78-3.95 (m, 2H), 4.78-5.05 (m, 1H)

Preparation 39: 3-(trifluoromethyl)-2,4,5,7-tetrahydropyrano (3,4-c) pyrazole (Prep39)

To a solution of 5,6-(dihydro-2H-3-piran-yloxy)(trimethyl) silane (P38, 28.7 g, 167 mmol) in dry THF (570 ml), a solution of Methyllithium 1.6 M in diethyl ether (104 ml, 167 mmol) was added dropwise under argon at room temperature. After 2.5 hours the mixture was cooled to −78° C., and then dropwise treated at this temperature with a solution of ethyl trifluoroacetate (23.7 g, 19.9 ml, 167 mmol) in dry THF (20 ml. The mixture was allowed to slowly warm up to room temperature, stirred for 2 hours then quenched with sat. NH$_4$Cl solution (250 ml), keeping the internal temperature below +10° C. The two layers were separated and the aqueous one was extracted two times with ethyl acetate (each with 250 ml). The resulting combined organic phase was finally dried over sodium sulphate and the solvent removed by rotary evaporation to give the intermediate 4-(trifluoroacetyl)dihydro-2H-pyran-3(4H) one as a foamy yellow solid (32.7 g, quantitative). This intermediate (32.7 g, 167 mmol) was dissolved in ethanol (570 ml) and to the solution hydrazine hydrate (16.7 g, 16.6 ml, 334 mmol) was added at room temperature. The resilting mixture was stirred at reflux temperature for 6 hours, then it was allowed to cool down to room temperature and the solvent was removed by rotary evaporation. The residue was partitioned between DCM (400 ml) and water (200 ml). The aqueous layer was extracted with DCM in two times (each with 150 ml). The combined organic layers were washed with water (200 ml), brine (150 ml) and dried over sodium sulphate. The solvent was removed by rotary evaporation to obtain 20.47 g of a yellow solid.

by SiO$_2$ flash chromatography eluting with Cyclohexane/ethyl acetate from 7/3 to 1/1.

The desired product was isolated as a white solid (17.2 g) after purification by SiO$_2$ flash chromatography eluting with Cyclohexane/ethyl acetate from 7/3 to 1/1.

MS (ES) (m/z): 191 [M+H]$^+$ $^1$H-NMR (400 MHz, CDCl$_3$) δ ppm 13.28 (1H, br s), 4.68 (2H, s), 3.80 (2H, t), 2.61 (2H, m)

Preparation 40: 2,4-bis(methyloxy)-5-(4-methyl-1,3-thiazol-2-yl)pyrimidine (Prep40)

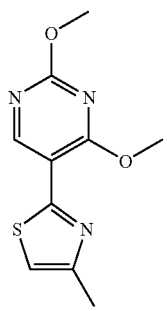

2-iodo-4-methyl-1,3-thiazole (prepared according to procedure described in JACS 123 (6), 1017-1022, (2001), 250 mg, 1.111 mmol) was dissolved in 1,2-Dimethoxyethane (DME) (4.629 ml). Pd(Ph3P)4 (64.2 mg, 0.056 mmol) was added and the mixture was stirred at room temperature for 10 minutes. 1M aqueous sol. Sodium bicarbonate (4.443 ml, 4.44 mmol) and [2,4-bis(methyloxy)-5-pyrimidinyl]boronic acid (409 mg, 2.222 mmol) were added and the resulting mixture was stirred at 85° C. for 2 hours. The mixture was allowed to cool to rt and it was diluted with DCM (5 mL). The aqueous was separated and extracted with DCM (2×5 mL). The organics were combined and dried (Na2SO4 then rotaevaporator) to give a yellow solid that was purified by silica chromatography (Biotage SP1, 25+M), eluting with DCM:MeOH from 100:0 to 9:1 to afford the title compound as a pale yellow solid (280 mg, 78% yield).

MS (ES) (m/z): 238 [M+H]$^+$

Preparation 41: 5-(4-methyl-1,3-thiazol-2-yl)-2,4 (1H,3H)-pyrimidinedione (Prep 41)

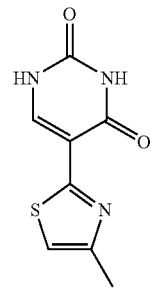

2,4-bis(methyloxy)-5-(4-methyl-1,3-thiazol-2-yl)pyrimidine (Prep40, 280 mg, 0.861 mmol) was dissolved in 18 mL of hydrochloric acid 4M in dioxane and the resulting mixture was stirred in a round bottomed flask at 90° C. for 2 hours. Then it was cooled to rt and dried under vacuum to afford the title compound as a yellow solid (300 mg, 0.760 mmol)

MS (ES) (m/z): 210 [M+H]$^+$

Preparation 42: 5-(4-methyl-1,3-thiazol-2-yl)-3-(phenylcarbonyl)-2,4(1H,3H)-pyrimidinedione (Prep 42)

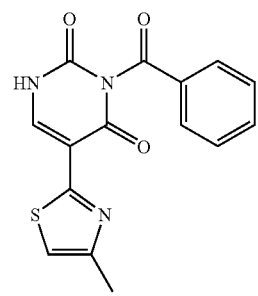

5-(4-methyl-1,3-thiazol-2-yl)-2,4(1H,3H)-pyrimidinedione (Prep41, 300 mg, 0.760 mmol) suspended in dry Pyridine (3 ml) was slowly added to a stirring solution of BENZOYL CHLORIDE (0.265 ml, 2.280 mmol) in Pyridine (1 mL) under nitrogen atmosphere. The resulting yellow solution was stirred at rt for 7 hours. Water was added (3 mL) and the mixture was extracted with EtOAc (10 mL). The organic was washed with NH4Cl saturated aqueous solution (2×2 mL) then with NaHCO3 aqueous saturated solution (1×3 mL), dried (Na2SO4, vacuo) to afford a yellow solid that was diluted in EtOAc (20 mL) and washed again with NaHCO3 aqueous saturated solution (2×5 mL), dried (Na2SO4, vacuo)

to afford the title compound as a yellow solid (274 mg, 0.411 mmol) used in the next reaction step without further purification.

MS (ES) (m/z): 314 [M+H]$^+$

Preparation 43: 1-[3,3-bis(methyloxy)propyl]-5-(4-methyl-1,3-thiazol-2-yl)-3-(phenylcarbonyl)-2,4(1H,3H)-pyrimidinedione (Prep43)

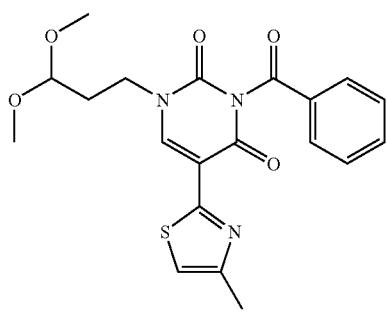

5-(4-methyl-1,3-thiazol-2-yl)-3-(phenylcarbonyl)-2,4(1H,3H)-pyrimidinedione (Pre42 100 mg, 0.150 mmol), K2CO3 (20.73 mg, 0.150 mmol), TBAI (5.54 mg, 0.015 mmol) and 3-bromo-1,1-bis(methyloxy)propane (0.020 mL, 0.150 mmol) in N,N-Dimethylformamide (DMF) (2 mL) dry were stirred in a closed vial at rt for 2 days. K2CO3 (10 mg) and 3-bromo-1,1-bis(methyloxy)propane (0.010 mL) were added and the mixture was stirred at rt for 6 hrs then left standing at rt over the week-end. The mixture was stirred again at rt for 2 days and left at rt for a week.

The mixture was diluted with EtOAc (ca 15 mL) and washed with small portion of ice/water (3×1 mL). The organic was dried (Na2SO4, rotary) to afford a crude that was purified by silica chromatography (12+M, Biotage SP1) eluting with Cyclohexane:EtOAc 100:0 to 50:50 to afford the title compound as a yellow oil (54 mg, 87% yield).

MS (ES) (m/z): 416 [M+H]$^+$

1H NMR (400 MHz, CHLOROFORM-d) ppm 2.10-2.17 (m, 2H) 2.48-2.51 (m, 3H) 3.38 (s, 6H) 4.04 (t, 2H) 4.51 (t, 1H) 6.92-6.95 (m, 1H) 7.45-7.58 (m, 2H) 7.64-7.73 (m, 1H) 7.95-8.01 (m, 2H) 8.56 (s, 1H)

Preparation 44: 1-[3,3-bis(methyloxy)propyl]-5-(4-methyl-1,3-thiazol-2-yl)-2,4(1H,3H)-pyrimidinedione (Prep 44)

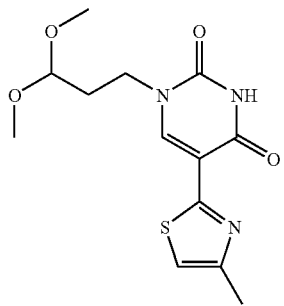

1-[3,3-bis(methyloxy)propyl]-5-(4-methyl-1,3-thiazol-2-yl)-3-(phenylcarbonyl)-2,4(1H,3H)-pyrimidinedione (Prep 43, 54 mg, 0.130 mmol) in 2M solution of ammonia in MeOH a (2 mL, 4.00 mmol) was stirred at rt for 6 hours and then the resulting mixture evaporated under vacuum.

The crude was loaded on SCX cartridge (2 g) eluting with DCM, MeOH, Ammonia 2M in MeOH (8 mL each). Ammonia fraction was collected and dried to afford the title compound as a white solid (34 mg, 84% yield).

MS (ES) (m/z): 312 [M+H]$^+$

Preparation 45: 3-[5-(4-methyl-1,3-thiazol-2-yl)-2,4-dioxo-3,4-dihydro-1(2H)-pyrimidinyl]propanal (Prep 45)

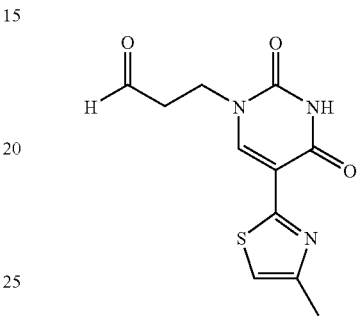

To a solution of 1-[3,3-bis(methyloxy)propyl]-5-(4-methyl-1,3-thiazol-2-yl)-2,4(1H,3H)-pyrimidinedione (Pre 44, 34 mg, 0.109 mmol) in Tetrahydrofuran (THF) (1.5 ml) 1M aqueous HCl (0.546 ml, 0.546 mmol) was added and the mixture was stirred at rt for 5 hrs. Other 1M aqueous HCl (0.273 ml, 0.273 mmol) was added and the mixture was stirred at rt overnight. Volatiles were evaporated (rotary, cold bath) and the residue was taken up with TEA (0.122 ml, 0.874 mmol) and THF (3 mL). The slurry was evaporated to dryness (rotary) to afford a crude that was used in the next reaction step assuming quantitative conversion to target compound (0.109 mmol) without any further purification MS (ES) (m/z): 266 [M+H]$^+$ Preparation 46: 5-(3-methyl-4-isothiazolyl)-2,4-bis(methyloxy)pyrimidine (Prep46)

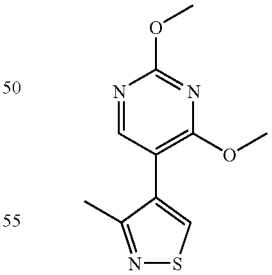

4-bromo-3-methylisothiazole (prepared according to literature: Isothiazoles. II. Isothiazolealdehydes and isothiazolyl ketones. Buttimore, D.; Jones, D. H.; Slack, R.; Wooldridge, K. R. H. Journal of the Chemical Society, 1963, 2032-9), (160 mg, 0.899 mmol) was dissolved in 1,2-Dimethoxyethane (DME) (3744 µl). Pd(Ph3P)$_4$ (51.9 mg, 0.045 mmol) was added and the mixture was stirred at room temperature for 10 minutes. 1M aqueous sol. A saturated solution of Sodium bicarbonate (3.6 mL 3.59 mmol) and

[2,4-bis(methyloxy)-5-pyrimidinyl]boronic acid (331 mg, 1.797 mmol) were added and the resulting mixture was stirred at 85° C. for 2 hours and at rt overnight.

The mixture was diluted with NaHCO3 sat sol and DCM (2 mL each), the aqueous was separated and extracted with DCM (2×5 mL). The organics were combined and dried (rotaevaporator) to give a brown solid that was purified by silica chromatography (Biotage SP1, 12+M), eluting with Cyclohexane:EtOAc from 100:0 to 7:3 to afford the title compound as a brown solid (10 mg, 4.7% yield).

A second batch of compound was prepared following the above described procedure starting from 46 mg of 4-bromo-3-methylisothiazole and obtaining 21.6 mg of the title compound.

MS (ES) (m/z): 238 [M+H]+.

1H NMR (400 MHz, CHLOROFORM-d) d ppm 2.43 (s, 3H) 4.03 (s, 3H) 4.07 (s, 3H) 8.19 (s, 1H) 8.52 (s, 1H)

Preparation 47: 5-(3-methyl-4-isothiazolyl)-2,4(1H,3H)-pyrimidinedione (Prep 47)

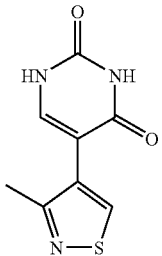

5-(3-methyl-4-isothiazolyl)-2,4-bis(methyloxy)pyrimidine (Prep 46, two batches combined, 30 mg, 0.148 mmol) was suspended in a 4M solution of HYDROCHLORIC ACID (1580 μl, 6.32 mmol) in dioxane the mixture was stirred at 90° for 2.5 hours. The mixture was allowed to cool to rt and dried (rotary) to afford a yellowish solid (0.126 mmol, yield considered quantitative assuming complete conversion to target compound).

MS (ES) (m/z): 210 [M+H]+.

1H NMR (400 MHz, DMSO-d6) d ppm 2.34 (s, 3H) 7.54-7.62 (m, 1H) 8.85 (s, 1H) 11.13-11.22 (m, 1H) 11.30-11.37 (br, 1H)

Preparation 48: 3-[5-(3-methyl-4-isothiazolyl)-2,4-dioxo-3,4-dihydro-1(2H)-pyrimidinyl]propanal (Prep 48)

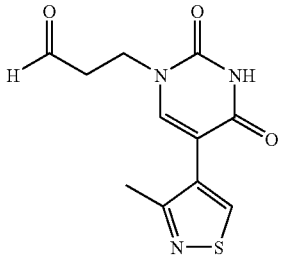

5-(3-methyl-4-isothiazolyl)-2,4(1H,3H)-pyrimidinedione (Pre 47, 0.126 mmol) was dissolved in N,N-Dimethylformamide (DMF) (1 ml). TRIETHYLAMINE (0.021 ml, 0.151 mmol) was added and the mixture was stirred at room temperature for 5 minutes. Acrolein (8.42 μl, 0.126 mmol) was added and the mixture was stirred at room temperature monitoring the reaction progression by LCMS. After 7 hrs Acrolein (3 μl) was added and the mixture was stirred at rt overnight.

Work up: NH4Cl saturated sol and EtOAc (5 mL each), extraction with EtOAc (2×5 mL). Organics filtered through a separation cartridge, combined and dried (rotary adding Cyclohexane to help DMF evaporation) to afford a crude as dark yellow oil that was used in the next reaction step assuming quantitative conversion to target compound (0.126 mmol).

MS (ES) (m/z): 266 [M+H]+.

Preparation 49: 5-(5-methyl-4-isoxazolyl)-2,4-bis(methyloxy)pyrimidine (Prep 49)

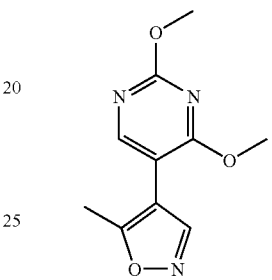

2,4-dimethoxypyrimidine-5-boronic acid (commercially available from Aldrich, 0.264 g, 1.435 mmol), 4-iodo-5-methylisoxazole (0.200 g, 0.957 mmol) and TETRAKIS(TRIPHENYLPHOSPHINE)PALLADIUM (0) (0.221 g, 0.191 mmol) in 1,2-Dimethoxyethane (DME) (5 ml) were stirred until dissolution of reactants, then sodium carbonate 1M (2.87 ml, 2.87 mmol) was added and the mixture heated at 90° C. for 4 h. Solids were filtered off by filtration tube and washed by DCM, organic phase was washed by a saturated solution of ammonium chloride (20 mL), brine (20 mL), dried upon sodium sulphate and evaporated.

Residue was purified on silica (biotage 25M, Cy/AcOEt 8:2) obtaining N4735-2-1: 5-(5-methyl-4-isoxazolyl)-2,4-bis(methyloxy)pyrimidine (0.088 g, 0.398 mmol, 41.6% yield).

MS (ES) (m/z): 223 [M+H]+.

Preparation 50: 5-(5-methyl-4-isoxazolyl)-2,4(1H,3H)-pyrimidinedione (Prep 50)

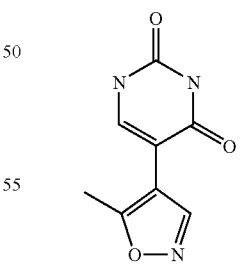

5-(5-methyl-4-isoxazolyl)-2,4-bis(methyloxy)pyrimidine (Prep 49, 0.088 g, 0.398 mmol) was heated in hydrochloric acid 4M in dioxane (1 ml, 4.00 mmol) at 80° C. for overnight. Reaction complete at HPLC analysis.

Solvents were removed under reduced pressure to give the title compound 5-(5-methyl-4-isoxazolyl)-2,4(1H,3H)-pyrimidinedione (0.066 g, 0.294 mmol, 73.9% yield).

MS (ES) (m/z): 194 [M+H]+.

Preparation 51: 5-[5-(5-methyl-4-isoxazolyl)-2,4-dioxo-3,4-dihydro-1(2H)-pyrimidinyl]acetaldehyde (Prep 51)

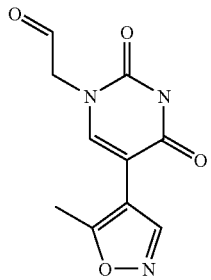

To a solution of 5-(5-methyl-4-isoxazolyl)-2,4(1H,3H)-pyrimidinedione (Prep 50, 0.033 g, 0.171 mmol) in N,N-Dimethylformamide (DMF) (2 ml) under an argon atmosphere, TRIETHYLAMINE (0.030 ml, 0.215 mmol) was added and the mixture stirred at r.t. for 5 min., then acroleyn (0.011 ml, 0.171 mmol) was added and the mixture stirred overnight. Reaction checked at HPLC.

Work-up: sat NH4Cl (5 mL) was added and organic phase was separated. Aq. layer was extracted by DCM (2×5 mL). Combined organic layers were washed by brine (10 mL), dried upon sodium sulphate and concentrated to give 3-[5-(5-methyl-4-isoxazolyl)-2,4-dioxo-3,4-dihydro-1(2H)-pyrimidinyl]propanal (15 mg, 0.060 mmol, 35.2% yield).

Crude was used in the following reaction without any further purification.

MS (ES) (m/z): 250 [M+H]+.

Examples 1 and Example 2

5-[1-methyl-3-(trifluoromethyl)-1H-pyrazol-4-yl]-1-(3-{(1S,5R)-1-[4-(trifluoromethyl)phenyl]-3-azabicyclo[3.1.0]hex-3-yl}propyl)-2,4(1H,3H)-pyrimidinedione (E1) and 5-[1-methyl-3-(trifluoromethyl)-1H-pyrazol-5-yl]-1-(3-{(1S,5R)-1-[4-(trifluoromethyl)phenyl]-3-azabicyclo[3.1.0]hex-3-yl}propyl)-2,4(1H,3H)-pyrimidinedione (E2)

E1

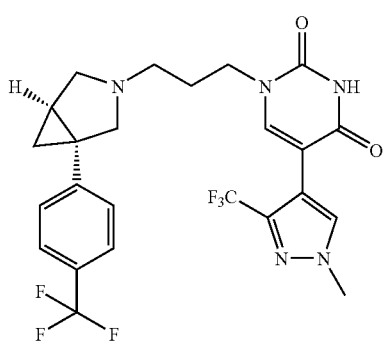

E2

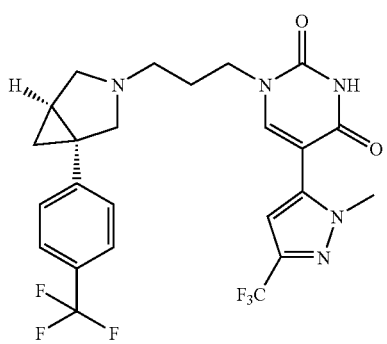

5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 148 mg, 0.293 mmol), [1-methyl-3-(trifluoromethyl)-1H-pyrazol-4-yl]boronic acid and [1-methyl-3-(trifluoromethyl)-1H-pyrazol-5-yl]boronic acid (Prep11, 71 mg, 0.366 mmol), and tetrakis(triphenylphosphine)palladium (0) (42.3 mg, 0.037 mmol) were stirred in 1,2-Dimethoxyethane (DME) (4 ml) until dissolution of reagents. Sodium carbonate 1M solution (1.098 ml, 1.098 mmol) was added and the mixture heated in a microwave apparatus at 150° C. for 15 min. DCM/water (5+5 mL) were added and organic phase separated by phase separation tube. Organic layer was loaded on SCX cartridge (1 g), washed by MeOH (2 mL) and products eluted by 2M methanolic ammonia. Ammonia phase was concentrated to give a crude that was purified twice by fraction lynx obtaining:

Regioisomer 1 (E1): 5-[1-methyl-3-(trifluoromethyl)-1H-pyrazol-4-yl]-1-(3-{(1S,5R)-1-[4-(trifluoromethyl)phenyl]-3-azabicyclo[3.1.0]hex-3-yl}propyl)-2,4(1H,3H)-pyrimidinedione (1.4 mg).

Regioisomer 2 (E2): 5-[1-methyl-3-(trifluoromethyl)-1H-pyrazol-5-yl]-1-(3-{(1S,5R)-1-[4-(trifluoromethyl)phenyl]-3-azabicyclo[3.1.0]hex-3-yl}propyl)-2,4(1H,3H)-pyrimidinedione (2.3 mg).

Example 1

1H NMR (CHLOROFORM-d) δ ppm 8.24 (br. s., 1H) 7.92 (s, 1H) 7.53 (d, 2H) 7.45 (s, 1H) 7.20 (d, 2H) 3.97 (s, 3H) 3.87 (t, 2H) 3.28-3.38 (m, 1H) 3.03-3.14 (m, 1H) 2.42-2.62 (m, 4H) 1.81-2.00 (m, 2H) 1.72-1.80 (m, 1H) 1.39-1.47 (m, 1H) 0.79-0.91 (m, 1H)

Example 2

1H NMR (CHLOROFORM-d) δ ppm 7.53 (d, 2H) 7.46 (s, 1H) 7.20 (d, 2H) 6.48 (s, 1H) 3.74-3.98 (m, 5H) 3.31 (d, 1H) 3.06 (d, 1H) 2.43-2.66 (m, 4H) 1.85-1.97 (m, 2H) 1.73-1.85 (m, 1H) 1.27-1.42 (m, 1H) 0.79-0.92 (m, 1H)

Example 3

5-(1,3-dimethyl-1H-pyrazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E3)

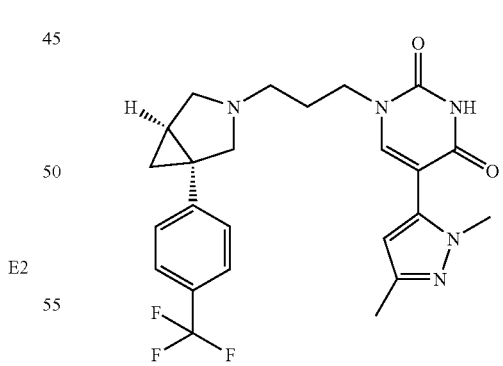

In a 5 mL microwave vial, 5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 127 mg, 0.251 mmol), 1,3-dimethyl-5-(4,4,5,5-tetramethyl-1,3,2-dioxaborolan-2-yl)-1H-pyrazole (commercially available from Aurora, 112 mg, 0.503 mmol) and tetrakis(triphenylphosphine)palladium (0) (58.1 mg, 0.050 mmol) in 1,2-Dimethoxyethane (DME) (4 ml) were stirred until dissolution of reactants, then sodium carbonate 1M (0.754 ml, 0.754 mmol) was added and the resulting mixture microwaved at 150° C. for 15 minutes.

EtOAc and water were added (50+50 mL), organic phase was washed with water (2×50 mL), dried upon sodium sulphate and concentrated under reduced pressure. The residue was loaded on SCX (5 mg), washed by MeOH (10 mL) and eluted by methanolic NH$_3$ 2M. Ammonia phase was concentrated to give an oil that was purified by fraction lynx. Solvent was concentrated and the residue loaded on SCX, washed by MeOH (10 mL) and eluted by methanolic NH3 2M. Ammonia phase was concentrated to the title compound as free base (90 mg, 0.177 mmol).

MS (ES) (m/z): 473.00 [M+H]+

$^1$H NMR (CHLOROFORM-d) δ ppm 7.55 (d, J=8.21 Hz, 2H) 7.37 (s, 1H) 7.22 (d, 2H) 6.01 (s, 1H) 3.83-3.96 (m, 2H) 3.77 (s, 3H) 3.34 (d, J=8.34 Hz, 1H) 3.09 (d, J=8.59 Hz, 1H) 2.43-2.70 (m, 5H) 2.28 (s, 3H) 1.87-2.03 (m, 2H) 1.80 (dd, J=7.71, 3.92 Hz, 1H) 1.39 (t, J=4.36 Hz, 1H) 0.88 (dd, J=8.08, 4.42 Hz, 1H)

Example 4

5-(1,3-dimethyl-1H-pyrazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E4)

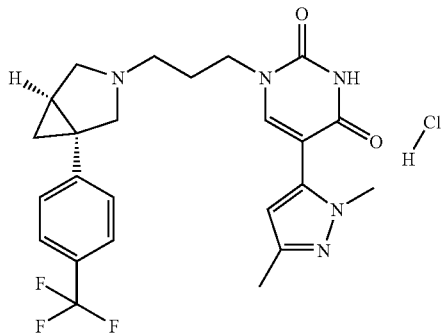

5-(1,3-dimethyl-1H-pyrazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E3, 90 mg, 0.177 mmol) was dissolved in diethyl ether (2 ml) and HCl 1M in diethylether (0.177 mmol, 0.177 ml) was added dropwise. The white solid obtained was triturated in Et2O (2×4 ml) to give, after filtration, the title compound (50 mg, 0.078 mmol).

MS (ES) (m/z): 473.00 [M+H]+.

$^1$H NMR (MeOD) δ ppm 7.90 (s, 1H) 7.68 (d, J=8.21 Hz, 2H) 7.51 (d, J=8.21 Hz, 2H) 6.23 (s, 1H) 4.19 (d, J=11.24 Hz, 1H) 3.83-4.09 (m, 3H) 3.59-3.85 (m, 5H) 3.36-3.46 (m, 2H) 2.08-2.48 (m, 5H) 1.06-1.56 (m, 3H).

Example 5

5-(5-methyl-1,3,4-thiadiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (E5)

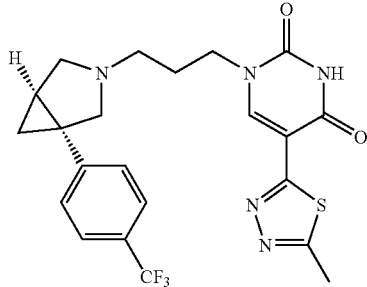

To a stirred solution of 5-(5-methyl-1,3,4-thiadiazol-2-yl)-2,4(1H,3H)-pyrimidinedione (Prep. 13, 76 mg, 0.289 mmol) in N,N-Dimethylformamide (DMF) (2 ml), triethylamine (0.048 ml, 0.347 mmol) was added and the mixture was stirred for 5 min, after which acroleyn (0.019 ml, 0.289 mmol) was added and the mixture furtherly stirred at r.t. for overnight.

A saturated solution of NH$_4$Cl (10 mL) and EtOAc (10 ml) were added and aq. phase was extracted by AcOEt (2×10 ml). Combined organic layers were dried on sodium sulphate and concentrated under reduced pressure, to give 3-[5-(5-methyl-1,3,4-thiadiazol-2-yl)-2,4-dioxo-3,4-dihydro-1(2H)-pyrimidinyl]propanal (54 mg, 0.203 mmol). Crude was used without any further purification.

Residue was diluted in 1,2-Dichloroethane (DCE) (2.000 ml), (1S,5R)-1-[4-(trifluoromethyl)phenyl]-3-azabicyclo [3.1.0]hexane (Prep4, 65.7 mg, 0.289 mmol) and acetic acid (0.050 ml, 0.868 mmol) followed after 10 minutes by sodium triacethoxyborohydride (67.4 mg, 0.318 mmol) were added and mixture stirred at 0° C. for 3 h.

A saturated solution of NaHCO$_3$ (5 mL) and DCM (5 mL) were added, organic layer was separated and concentrated under reduced pressure.

Residue was purified by the fraction lynx, obtaining the title compound (7 mg, 0.015 mmol).

$^1$H NMR (CHLOROFORM-d) δ ppm 8.68 (s, 1H) 7.52 (d, 2H) 7.22 (d, 2H) 4.01 (m, 2H) 3.40 (d, 1H) 3.15 (d, 1H) 2.80 (s, 3H) 2.61 (m, 3H) 2.50 (dd, 1H) 1.97 (m, 2H) 1.80 (m, 1H) 1.51 (t, 1H) 0.90 (q, 1H).

Example 6

5-(5-methyl-1,3,4-thiadiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E6)

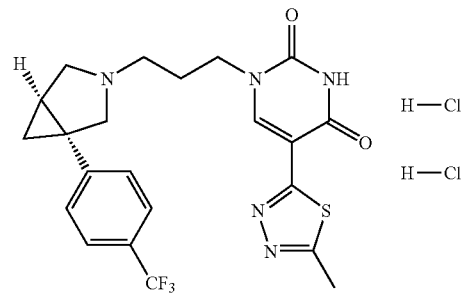

5-(5-methyl-1,3,4-thiadiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (E5, 7 mg, 0.015 mmol) was dissolved in diethyl ether (1 ml) and hydrochloric acid 1M in diethylether (0.030 ml, 0.030 mmol) was added. The solid obtained was triturated in diethylether (2×1 mL) giving the title compound as a white solid (8.8 mg, 0.014 mmol).

$^1$H NMR (DMSO-d6) δ ppm 12.06 (s, 1H) 10.51 (s, 1H) 8.90 (s, 1H) 7.69 (d, J=8.30 Hz, 2H) 7.48 (d, J=8.30 Hz, 2H) 4.05 (m, 2H) 3.91-4.02 (m, 2H) 3.71 (dd, J=11.47 Hz, 1H) 3.58-3.67 (m, 1H) 3.45-3.55 (m, 1H) 3.20-3.34 (m, 2H) 2.71 (s, 3H) 2.23-2.33 (m, 1H) 2.09-2.21 (m, 2H) 1.69 (t, J=5.37 Hz, 1H) 1.14-1.22 (m, 1H)

Example 7

5-(4,5-dimethyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (E7)

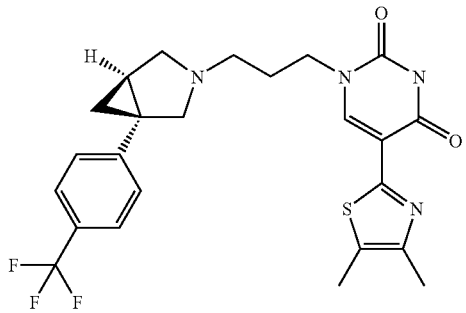

[5-(4,5-dimethyl-1,3-thiazol-2-yl)-2,4-dioxo-3-(phenylcarbonyl)-3,4-dihydro-1(2H)-pyrimidinyl]propanal (Prep18, 0.098 mmol from previous reaction considered quantitative) was dissolved in Acetonitrile (1.500 ml). (1S,5R)-1-[4-(trifluoromethyl)phenyl]-3-azabicyclo[3.1.0]hexane (Prep4, 0.022 g, 0.098 mmol) was added and to the resulting slurry 1,2-Dichloroethane (DCE) (1.5 ml) and Acetic acid (0.011 ml, 0.196 mmol) were added. The resulting clear and dark yellow solution was stirred at rt for 10 minutes then it was cooled to 0° C. and sodium triacetoxyborohydryde (0.023 g, 0.108 mmol) was added in one portion. The mixture was stirred while the temperature slowly rose to rt (ca 5 hrs). The mixture was diluted with EtOAc (20 mL) washed with aqueous saturated NaHCO$_3$ and extracted with EtOAc (2×5 mL). The organics were combined and dried (Na$_2$O$_4$, rotary evaporator) to afford a crude that was purified by silica chromatography, eluting with DCM:MeOH 100:0 to 9:1 to afford a yellow foam that was purified by SCX (5 g) eluting with DCM, MeOH, Ammonia 1M in MeOH (10 mL each) to afford 36 mg of compound that was further purified by FractionLynx. Product fraction was dried to afford 5 mg of impure title compound that was filtered through an SCX cartridge (500 mg) eluting with DCM, MeOH, Ammonia 2M in MeOH. Fraction from ammonia was dried to afford the title compound as a white solid (3 mg)

MS (ES) (m/z): 491 [M+H]$^+$.

$^1$H-NMR (400 MHz, CHLOROFORM-d) δ ppm 0.85-0.97 (m, 1H) 1.49-1.72 (m, 1H) 1.76-1.87 (m, 1H) 1.90-2.03 (m, 2H) 2.33 (s, 3H) 2.39 (s, 3H) 2.43-2.69 (m, 4H) 3.10-3.25 (m, 1H) 3.37-3.50 (m, 1H) 3.89-4.05 (m, 2H) 7.19-7.26 (m, 2H) 7.49-7.62 (m, 2H) 8.45-8.57 (m, 1H)

Example 8

5-(4,5-dimethyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E8)

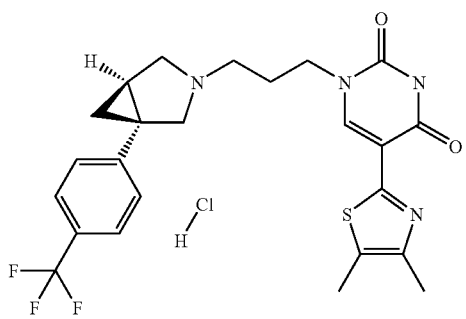

5-(4,5-dimethyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (E 7, 3 mg, 6.12 μmol) was suspended in Diethyl ether (0.5 ml). 1M Hydrochloric acid (7.34 μl, 7.34 μmol) in Et$_2$O was added and the resulting solid was triturated with Et$_2$O (3×0.3 mL) to afford the title compound as a yellowish solid (2.9, mg, 77% yield)
MS (ES) (m/z): 491 [M+H]$^+$.

Example 9

5-(1-methyl-1H-imidazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E9)

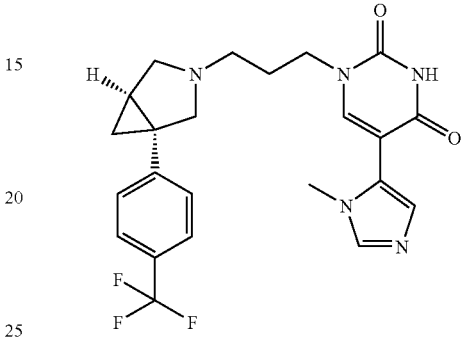

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep10, 100 mg, 0.198 mmol), 1-methyl-5-(tributylstannanyl)-1H-imidazole (commercially available from MayBridge 73.5 mg, 0.198 mmol) and Bis(Thriphenylphosphine)Palladium(II)chloride (6.95 mg, 9.90 μmol) in N,N-Dimethylformamide (DMF) (4 ml) mixed in a closed vials were shaked in a PLS at 90° C. for 1 hour then at 110° C. overnight (ca 14 hrs). The mixture was cooled to rt and left standing at rt for 1 day. Then it was filtered on a celite pad washing with DCM and MeOH letting the solution going through an SCX (20 g) and collecting fractions. The SCX was finally eluted with Ammonia 2M in MeOH.

Fractions from ammonia were combined and dried (rotary evaporator) to afford 75 mg of a yellow oil that was submitted to LC/MS preparative purification. Fraction collected from LC purification was dried (rotary evaporator) to afford the title compound (10.4 mg) as a white solid:

$^1$H-NMR: (400 MHz, CHLOROFORM-d) δ ppm 0.87 (q, 1H) 1.39 (t, 1H) 1.76-1.83 (m, 1H) 1.89-2.00 (m, 2H) 2.49-2.64 (m, 4H) 3.10 (d, 1H) 3.33 (d, 1H) 3.62 (s, 3H) 3.82-3.98 (m, 2H) 7.02 (s, 1H) 7.21 (d, 2H) 7.36-7.39 (m, 1H) 7.52-7.56 (m, 3H) 8.28 (br. s., 1H)

Example 10

5-(1-methyl-1H-imidazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E10)

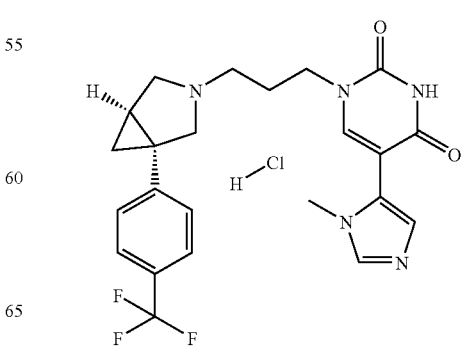

5-(1-methyl-1H-imidazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E9, 9.4 mg, 0.020 mmol) was suspended in Diethyl ether (1 ml) and Hydrochloric acid (0.025 ml, 0.025 mmol) 1M in Et$_2$O was added. A gum was formed and it was dissolved in MeOH and DCM (0.3 mL each) and dried. The white solid formed was triturated with Et$_2$O (3×0.3 mL) to afford the title compound as a white solid (8.2 mg).

MS (ES) (m/z): 460 [M+H]$^+$.

$^1$H-NMR (DMSO-d$_6$) δ: ppm 1.15-1.25 (m, 1H) 1.80-1.95 (m, 1H) 2.09-2.22 (m, 2H) 2.23-2.38 (m, 1H) 3.12-3.28 (m, 2H) 3.44-3.54 (m, 1H) 3.55-3.65 (m, 1H) 3.65-3.74 (m, 1H) 3.76 (s, 3H) 3.82-3.93 (m, 2H) 3.96-4.13 (m, 1H) 7.43-7.54 (m, 2H) 7.65-7.77 (m, 3H) 8.13 (s, 1H) 9.10 (brs, 1H) 10.87-11.21 (brs, 1H) 11.87 (s, 1H)

Example 11

5-(1-methyl-1H-pyrrol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E11)

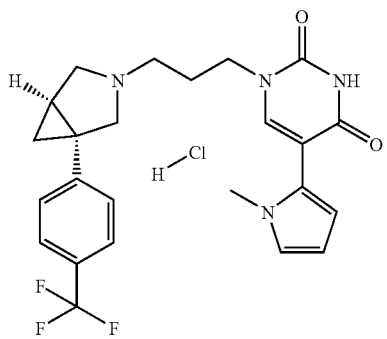

1-methyl-2-(tributylstannanyl)-1H-pyrrole (commercially available from Aldrich 73.3 mg, 0.198 mmol), 5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep10, 100 mg, 0.198 mmol) and Bis (Thriphenylphosphine)Palladium (II)chloride (6.95 mg, 9.90 μmol) in N,N-Dimethylformamide (DMF) (4 ml) in a closed vial were shaked in a PLS at 90° C. for 1 hour then at 110° C. overnight (15 h). The mixture was cooled to rt and filtered on a celite pad washing with DCM and MeOH letting the solution going through an SCX (20 g) and collecting fractions. The SCX was finally eluted with Ammonia 2M in MeOH. Ammonia fractions were combined and dried to afford 103 mg of a brown oil that was submitted to preparative HPLC. Fraction collected from LC purification (with basic method) was dried (rotary evaporator) to afford the free base of the title compound as a white solid (18.1 mg).

5-(1-methyl-1H-pyrrol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (18.1 mg, 0.039 mmol) was suspended in Diethyl ether (1 ml) and Hydrochloric acid (0.047 ml, 0.047 mmol) 1M in Et$_2$O was added. A suspension was formed that was dried (vacuo). The white solid formed was triturated with Et$_2$O (3×0.3 mL) to afford the title compound as a white solid (17.6 mg)

MS (ES) (m/z): 459 [M+H]$^+$.

$^1$H NMR (500 MHz, DMSO-d6) ppm 1.17-1.23 (m, 1H) 1.58-1.63 (m, 1H) 2.05-2.12 (m, 2H) 2.27-2.33 (m, 1H) 3.19-3.29 (m, 2H) 3.47 (s, 3H) 3.48-3.54 (m, 1H) 3.60-3.66 (m, 1H) 3.70-3.76 (m, 1H) 3.77-3.84 (m, 2H) 4.06 (q, 1H) 5.96-6.01 (m, 2H) 6.77-6.81 (m, 1H) 7.49 (d, 2H) 7.70 (d, 2H) 7.74 (s, 1H) 10.21 (br. s., 1H) 11.53 (s, 1H)

Example 12

1-(3-{(1S,5R)-1-[4-(trifluoromethyl)phenyl]-3-azabicyclo[3.1.0]hex-3-yl}propyl)-5-(1,3,5-trimethyl-1H-pyrazol-4-yl)-2,4(1H,3H)-pyrimidinedione (E12)

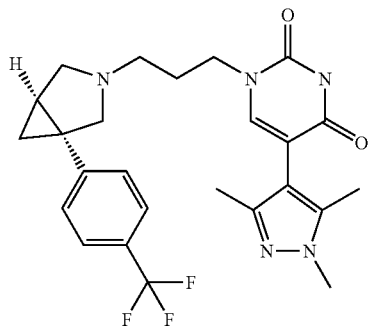

In the first batch, 5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep.10, 150 mg, 0.297 mmol) was dissolved in 1,2-Dimethoxyethane (DME) (2 ml) and then Pd(Ph$_3$)$_4$ (103 mg, 0.089 mmol) was added. The obtained solution was stirred at room temperature. After 10 min, 1,3,5-trimethyl-4-(4,4,5,5-tetramethyl-1,3,2-dioxaborolan-2-yl)-1H-pyrazole (commercially available from Maybridge, 140 mg, 0.594 mmol) and 1M/H$_2$O sol. of NaHCO$_3$ (2 ml, 2.000 mmol) were added. The obtained reaction mixture was stirred for 10 min at 150° C. in the MW oven. 5 ml of water were added to the reaction mixture and the organic phase was extracted with DCM (10 ml×3 times). The collected organic phases were evaporated. This mixture was iteratively purified (two purification steps) by preparative LC-MS (basic method). Two fractions were obtained: one pure (8.6 mg), the other not pure enough by 1H NMR (3.5 mg).

In a second batch, the same quantities of the same reagents were treated following the same procedure reported for the first batch. The obtained crude was iteratively purified (two purification steps) by preparative LC-MS.

All not pure fractions coming from preparative LC-MS of both batches were mixed together and purified again by preparative LC-MS.

All the pure fractions obtained from both batches at the end of this iterative purification procedure were mixed together and evaporated under vacuum to afford 32.7 mg (11% yield) of the title compound.

[Preparative LC-MS conditions—basic method: Column: Gemini C18 AXIA, 50×21 mm, 5 μm; Mobile phase: A: NH4HCO3 sol. 10 mM, pH10; B: CH3CN; Gradient: 35% (B) for 1 min, 35% to 45% (B) in 9 min, 45% to 100% (B) in 2 min, 100% (B) for 1.5 min; Flow rate: 17 ml/min; UV range: 210-350 nm; Ionization: ES+; Mass range: 100-900 amu].

MS (ES) (m/z): 488.21 [M+H]$^+$.

$^1$H NMR (400 MHz, CHLOROFORM-d): ppm 8.72 (1H, s) 7.55 (2H, d) 7.22 (2H, d) 7.10 (1H, s) 3.81-3.94 (2H, m)

3.76 (3H, s) 3.34 (1H, d) 3.09 (1H, d) 2.54-2.66 (3H, m) 2.50 (1H, dd) 2.20 (3H, s) 2.18 (3H, s) 1.88-1.99 (2H, m) 1.76-1.82 (1H, m) 1.42 (1H, t) 0.86 (1H, dd).

Example 13

1-(3-{(1S,5R)-1-[4-(trifluoromethyl)phenyl]-3-azabicyclo[3.1.0]hex-3-yl}propyl)-5-(1,3,5-trimethyl-1H-pyrazol-4-yl)-2,4(1H,3H)-pyrimidinedione dihydrochloride (E13)

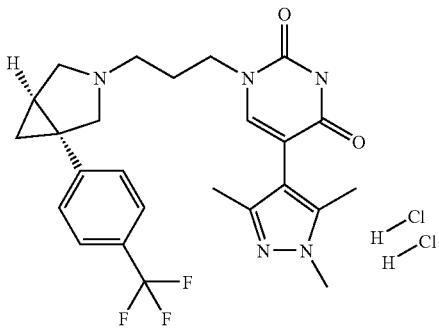

1-(3-{(1S,5R)-1-[4-(trifluoromethyl)phenyl]-3-azabicyclo[3.1.0]hex-3-yl}propyl)-5-(1,3,5-trimethyl-1H-pyrazol-4-yl)-2,4(1H,3H)-pyrimidinedione (E12, 32.7 mg, 0.065 mmol) was dissolved and sonicated in Diethyl ether (3 ml) to give a white suspension. A 1.25M solution of HCl in MeOH (0.130 ml, 0.163 mmol) was added at room temperature. The obtained mixture was sonicated for 3 min and the solvent evaporated in vacuo. Obtained 27.2 mg (72.4% yield) of the title compound as a white solid.

MS (ES) (m/z): 488.21.

$^1$H NMR (400 MHz, DMSO-$d_6$) δ ppm 11.38-11.43 (1H, m) 10.36-10.46 (1H, m) 7.68-7.73 (2H, m) 7.57-7.61 (1H, m) 7.45-7.53 (2H, m) 4.02-4.12 (1H, m) 3.68-3.86 (4H, m) 3.63-3.68 (3H, m) 3.44-3.54 (1H, m) 3.19-3.29 (2H, m) 2.24-2.36 (1H, m) 2.05-2.11 (3H, m) 1.98-2.03 (3H, m) 1.73-1.95 (1H, m) 1.61-1.72 (1H, m) 1.16-1.26 (1H, m) 1.09 (1H, t)

Example 14

5-(1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione (E14)

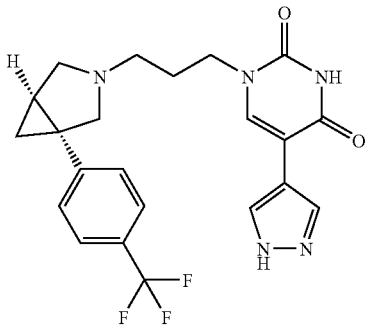

5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 60 mg, 0.119 mmol) was dissolved in 1,2-Dimethoxyethane (DME) (1 ml) to give a colorless solution. Pd(Ph$_3$)$_4$ (6.86 mg, 5.94 μmol) was added and the obtained yellow solution was stirred at room temperature for 10 min under N$_2$ atm. 1,1-dimethylethyl 4-(4,4,5,5-tetramethyl-1,3,2-dioxaborolan-2-yl)-1H-pyrazole-1-carboxylate (commercially available from Focus, 69.9 mg, 0.237 mmol) and 1M/H$_2$O sol. of NaHCO$_3$ (1 ml, 1.000 mmol) were added thereto. The reaction mixture was stirred at 90° C. After 5 h, 1,1-dimethylethyl 4-(4,4,5,5-tetramethyl-1,3,2-dioxaborolan-2-yl)-1H-pyrazole-1-carboxylate (69.9 mg, 0.237 mmol) in 0.5 ml of DME was added to the reaction mixture. The same addition was repeated again after 18 h.

After 24 h the reaction was quenched with 5 ml of water. The organic phase was extracted with DCM (10 ml×3 times). The collected organic phases were evaporated. The crude was purified by preparative LC-MS (basic method) to obtain 9.2 mg (16.87% yield) of the title compound.

[Preparative LC-MS conditions: Column: Gemini C18 AXIA, 50×21 mm, 5 μm; Mobile phase: A: NH4HCO3 sol. 10 mM, pH10; B: CH3CN; Gradient: 40% (B) for 3 min, 40% to 50% (B) in 8 min, 50% to 95% (B) in 0.1 min, 95% (B) for 1.9 min; Flow rate: 17 ml/min; UV range: 210-350 nm; Ionization: ES+; Mass range: 100-900 amu]

MS (ES$^-$) (m/z): 491.06, 444.06 [M–H$^+$]$^-$.

$^1$H NMR (400 MHz, ACETONITRILE-$d_3$) δ ppm 7.94 (2H, br. s.), 7.74 (1H, s), 7.61 (2H, d), 7.32 (2H, d), 3.83 (2H, t), 3.37 (1H, d), 3.08 (1H, d), 2.52-2.59 (3H, m), 2.45 (1H, dd), 1.83-1.92 (3H, m), 1.52 (1H, t), 0.89 (1H, dd).

Example 15

5-(2-methyl-1,3-thiazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione (E15)

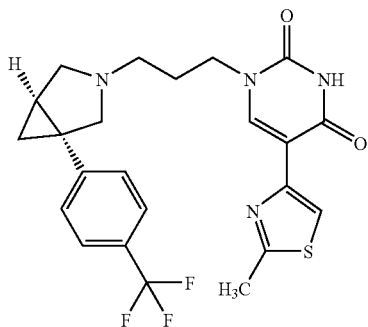

1-[3,3-bis(methyloxy)propyl]-5-(2-methyl-1,3-thiazol-4-yl)-2,4(1H,3H)-pyrimidinedione (Prep21, 58.5 mg, 0.188 mmol) was dissolved in 1,4-Dioxane (2 ml) to give a colorless solution. 1M/H$_2$O sol. of HCl (0.752 ml, 0.752 mmol) was added. The mixture was warmed at 50° C. After 3 h the solvent was evaporated. Obtained 62.5 mg of a white syrupy oil was used in the following reaction without any further purification.

The crude obtained in the previous step (62.5 mg) was dissolved in 1,2-Dichloroethane (DCE) (3 ml) and Acetonitrile (3.00 ml) to give a colorless solution. (1S,5R)-1-[4-(trifluoromethyl)phenyl]-3-azabicyclo[3.1.0]hexane (Prep4) 47.8 mg, 0.210 mmol) and acetic acid (0.024 ml, 0.420 mmol)

were added and the reaction mixture was then cooled to 0° C. NaBH(AcO)₃ (49.0 mg, 0.231 mmol) was added. After 3 h the reaction mixture was diluted with 10 ml of sat. acq. solution of NaHCO₃ and extracted with EtOAc (3×30 ml). The combined organic phases were washed with brine, dried over Na₂SO₄, filtered and the solvent evaporated. The obtained crude was purified by preparative LC-MS. 9.1 mg (9.08% yield) of the title compound were obtained as a white solid.

[Preparative LC-MS conditions: Column: Gemini C18 AXIA, 50×21 mm, 5 μm; Mobile phase: A: NH4HCO3 sol. 10 mM, pH10; B: CH3CN; Gradient: 40% to 45% (B) in 1 min, 45% to 80% (B) in 7 min, 80% to 100% (B) in 1 min, 100% (B) for 1.5 min; Flow rate: 17 ml/min; UV range: 210-350 nm; Ionization: ES+; Mass range: 100-900 amu]

MS (ES) (m/z): 477.09 [M+H]⁺.

¹H NMR (400 MHz, ACETONITRILE-d₃) δ ppm 9.12 (1H, s) 8.54 (1H, s) 7.94 (1H, s) 7.61 (2H, d) 7.33 (2H, d) 3.85-3.98 (2H, m) 3.44 (1H, d) 3.15 (1H, d) 2.64 (3H, s) 2.47-2.61 (3H, m) 2.45 (1H, dd) 1.82-1.94 (3H, m) 1.70 (1H, t) 0.93 (1H, dd).

Example 16

5-(4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione (E16)

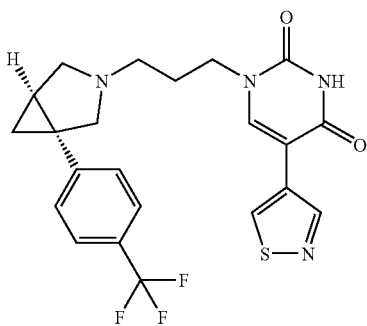

Step a)
1-[3,3-bis(methyloxy)propyl]-5-(4-isothiazolyl)-2,4(1H, 3H)-pyrimidinedione (Prep24, 60 mg, 0.139 mmol) was dissolved in 1,4-Dioxane (1 ml) to give a colorless solution. 1M/H₂O sol. of HCl (0.696 ml, 0.696 mmol) was added. After 4 h stirring at 50° C., the was solvent evaporated. The obtained crude (61.7 mg) was used without any further purification in the following step b).

Step b)
The crude coming from the previous step a) (61.7 mg) was dissolved in 1,2-Dichloroethane (DCE) (3 ml) to give a white suspension. Acetonitrile (3.00 ml) was added and the reaction mixture was cooled at 0° C. (1S,5R)-1-[4-(trifluoromethyl) phenyl]-3-azabicyclo[3.1.0]hexane (P4, 49.5 mg, 0.218 mmol) was added followed by AcOH (0.025 ml, 0.436 mmol) and NaBH(AcO)₃ (50.8 mg, 0.240 mmol). The white suspension obtained was stirred at 0° C. for 4 h, then the reaction mixture was diluted with 10 ml of saturated aqueous solution of NaHCO₃ and extracted with EtOAc (3×30 ml). The combined organic phases were washed with brine, dried over Na₂SO₄, filtered and the solvent evaporated. The crude was purified by preparative LC-MS. 16.1 mg of the title compound were isolated as a white solid.

[Preparative LC-MS conditions: Column: Gemini C18 AXIA, 50×21 mm, 5 μm; Mobile phase: A: NH4HCO3 sol. 10 mM, pH10; B: CH3CN; Gradient: 35% (B) for 1 min, 35% to 55% (B) in 9 min, 55% to 100% (B) in 0.1 min, 100% (B) for 1.9 min; Flow rate: 17 ml/min; UV range: 210-350 nm; Ionization: ES+; Mass range: 100-900 amu].

MS (ES) (m/z): 463.06 [M+H]⁺.

¹H NMR (400 MHz, ACETONITRILE-d₃) δ ppm 9.15 (1H, s) 8.83 (1H, s) 7.95 (1H, s) 7.61 (2H, d) 7.32 (2H, d) 3.88 (2H, t) 3.37 (1H, d) 3.08 (1H, d) 2.54-2.61 (3H, m) 2.46 (1H, dd) 1.97-2.00 (1H, m) 1.84-1.95 (3H, m) 1.50 (1H, t) 0.88 (1H, dd).

Example 17

5-(1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (E17)

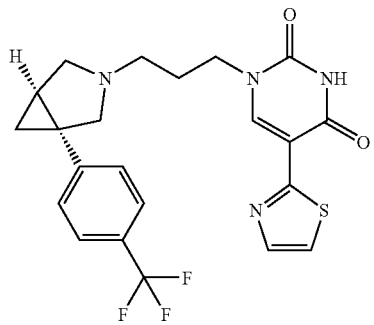

Step a)
1-[3,3-bis(methyloxy)propyl]-5-(1,3-thiazol-2-yl)-2,4 (1H,3H)-pyrimidinedione (Prep27, 33.9 mg, 0.114 mmol) was dissolved in 1,4-Dioxane (1 ml) to give a colorless solution. 1M/H₂O sol. of HCl (0.570 ml, 0.570 mmol) was added. After 4 h stirring at 50° C., the solvent was evaporated. The obtained crude (38.8 mg) was used without any further purification in the following step b).

Step b)
The crude coming from the previous step a) (38.8 mg) was dissolved in 1,2-Dichloroethane (DCE) (3 ml) to give a white suspension. Acetonitrile (3.00 ml) was added. (1S,5R)-1-[4-(trifluoromethyl)phenyl]-3-azabicyclo[3.1.0]hexane (Prep4, 31.1 mg, 0.137 mmol) was added and the reaction mixture was cooled at 0° C. AcOH (0.016 ml, 0.274 mmol) and NaBH(AcO)₃ (31.9 mg, 0.151 mmol) were added. Obtained a white suspension that was stirred at 0° C. After 4 h, the reaction mixture was diluted with 10 ml of saturated aqueous solution of NaHCO3 and extracted with EtOAc (3×30 ml). The combined organic phases were washed with brine, dried over Na₂SO₄, filtered and the solvent evaporated. The crude was purified by preparative LC-MS. 7.6 mg of the title compound were isolated as a white solid.

[Preparative LC-MS conditions: Column: Gemini C18 AXIA, 50×21 mm, 5 μm; Mobile phase: A: NH4HCO3 sol. 10 mM, pH10; B: CH3CN; Gradient: 35% (B) for 1 min, 35% to 50% (B) in 9 min, 50% to 100% (B) in 0.1 min, 100% (B) for 1.9 min; Flow rate: 17 ml/min; UV range: 210-350 nm; Ionization: ES+; Mass range: 100-900 amu].

MS (ES) (m/z): 463.06 [M+H]⁺.

1H NMR (400 MHz, ACETONITRILE-d₃) δ ppm 8.61 (1H, s) 7.81 (1H, d) 7.61 (2H, d) 7.47 (1H, d) 7.33 (2H, d) 3.96 (2H, t) 3.40 (1H, d) 3.11 (1H, d) 2.50-2.60 (3H, m) 2.45 (1H, dd) 1.84-1.95 (4H, m) 1.56 (1H, t) 0.87 (1H, dd)

Example 18

5-(1-methyl-1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione (E18)

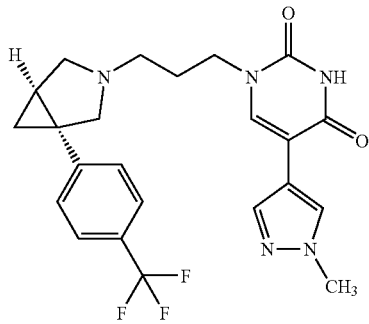

Step a)

1-[3,3-bis(methyloxy)propyl]-5-(1-methyl-1H-pyrazol-4-yl)-2,4(1H,3H)-pyrimidinedione (Prep30, 33.9 mg, 0.115 mmol) was dissolved in 1,4-Dioxane (1 ml) to give a colorless solution. 1M/H$_2$O solution of HCl (0.461 ml, 0.461 mmol) was added. After 4 h stirring at 50° C., the was solvent evaporated. The obtained crude (33.4 mg) was used without any further purification in the following step b).

Step b)

The crude coming from the previous step a) (33.4 mg) was dissolved in 1,2-Dichloroethane (DCE) (3 ml) to give a white suspension. Acetonitrile (3.00 ml), AcOH (0.015 ml, 0.269 mmol) and NaBH(AcO)$_3$ (31.4 mg, 0.148 mmol) were added. A white suspension was obtained. After 4 h stirring at room temperature, the reaction mixture was diluted with 10 ml of saturated aqueous solution of NaHCO$_3$ and extracted with EtOAc (3×30 ml). The combined organic phases were washed with brine, dried over Na$_2$SO$_4$, filtered and the solvent evaporated. The crude was purified by preparative LC-MS. Two fraction of the title compound were isolated (19.5 mg).

[Preparative LC-MS conditions: Column: Gemini C18 AXIA, 50×21 mm, 5 μm; Mobile phase: A: NH4HCO3 sol. 10 mM, pH10; B: CH3CN; Gradient: 35% (B) for 1 min, 35% to 55% (B) in 9 min, 55% to 100% (B) in 0.1 min, 100% (B) for 1.9 min; Flow rate: 17 ml/min; UV range: 210-350 nm; Ionization: ES+; Mass range: 100-900 amu].

MS (ES) (m/z): 460.16 [M+H]$^+$.

$^1$H NMR (500 MHz, DMSO-d$_6$) δ ppm 10.93-11.70 (1H, m) 8.04-8.09 (1H, m) 7.99-8.04 (1H, m) 7.70-7.78 (1H, m) 7.59 (2H, d) 7.31 (2H, d) 3.78-3.89 (3H, m) 3.71-3.79 (2H, m) 3.30 (1H, d) 3.02 (1H, d) 2.42-2.55 (3H, m) 2.29-2.41 (1H, m) 1.85-1.95 (1H, m) 1.71-1.85 (2H, m) 1.39-1.50 (1H, m) 0.58-0.91 (1H, m)

Example 19

5-(1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione (E19)

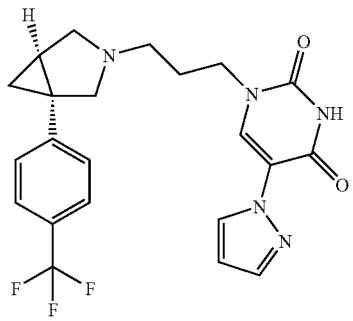

5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 60 mg, 0.119 mmol), 1H-pyrazole (26.7 mg, 0.392 mmol), copper iodide (24.88 mg, 0.131 mmol), N,N-dimethylglycine (13.47 mg, 0.131 mmol) and K$_2$CO$_3$ (36.1 mg, 0.261 mmol) were dissolved in Dimethyl Sulfoxide (DMSO) (1 ml) to give a colorless suspension with a white solid. After shaking at 150° C. for 18 h, the reaction mixture was diluted with EtOAc (5 ml) and the organic phase was washed with water (4×10 ml), then brine (5 ml), dried over Na$_2$SO$_4$, filtered ant the solvent evaporated. The obtained residue was purified by preparative LC-MS to give 9.8 mg (18.48% yield) of the title compound as a yellow oil.

[Preparative LC-MS conditions: Column: WATERS XTerra prep MS C18 OBD, 30×150 mm, 10 μm; Mobile phase: A: NH$_4$HCO$_3$ sol. 10 mM, pH 10; B: CH$_3$CN; Gradient: 10% (B) for 0.5 min, 10% to 95% (B) in 12.5 min, 95% to 100% (B) in 3 min. Flow rate: 40 ml/min; UV range: 210-400 nm; Ionization: ES+/ES−; Mass range: 130-900 amu].

MS (ES) (m/z): 446.13 [M+H]$^+$.

1H NMR (500 MHz, DMSO-d$_6$) δ ppm 11.79 (1H, br. s.), 8.21 (1H, s), 8.13 (1H, d), 7.57-7.64 (3H, m), 7.30 (2H, d), 6.42 (1H, d), 3.74-3.85 (2H, m), 3.31-3.39 (1H, m), 3.02 (1H, d), 2.46-2.52 (3H, m), 2.32-2.40 (1H, m), 1.74-1.95 (3H, m), 1.37-1.44 (1H, m), 0.73-0.86 (1H, m)

Example 20

1-(3-{(1S,5R)-1-[4-(trifluoromethyl)phenyl]-3-azabicyclo[3.1.0]hex-3-yl}propyl)-5-[3-(trifluoromethyl)-1H-pyrazol-1-yl]-2,4(1H,3H)-pyrimidinedione (E20)

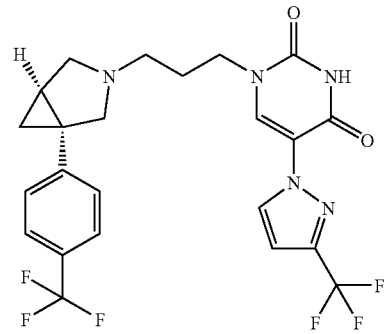

5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 60 mg, 0.119 mmol), copper(1+) iodide (24.88 mg, 0.131 mmol), N,N-dimethylglycine (13.47 mg, 0.131 mmol) and K$_2$CO$_3$ (36.1 mg, 0.261 mmol) were dissolved in Dimethyl Sulfoxide (DMSO) (1 ml) to give a light blue suspension with a white solid. 3-(trifluoromethyl)-1H-pyrazole (commercially available from Apollo, 53.3 mg, 0.392 mmol) was added. After shaking at 150° C. for 18 h, the reaction mixture was diluted with EtOAc (5 ml) and the organic phase was washed with water (4×10 ml), then brine (5 ml), dried over Na$_2$SO$_4$, filtered ant the solvent evaporated. The obtained crude was purified by preparative LC-MS. Obtained 12.5 mg of the title compound.

[Preparative LC-MS conditions: Column: Gemini C18 AXIA, 50×21 mm, 5 μm; Mobile phase: A: NH4HCO3 sol. 10 mM, pH10; B: CH3CN; Gradient: 30% to 35% (B) in 1 min, 35% to 65% (B) in 7 min, 65% to 100% (B) in 1 min, 100% (B) for 1.5 min; Flow rate: 17 ml/min; UV range: 210-350 nm; Ionization: ES+; Mass range: 100-900 amu].

1H NMR (600 MHz, CHLOROFORM-d) δ ppm 8.86 (1H, br. s.) 8.46 (1H, s) 8.33 (1H, s) 7.52 (2H, d) 7.21 (2H, d) 6.65 (1H, s) 3.91-3.99 (2H, m) 3.40 (1H, d) 3.16 (1H, d) 2.54 (4H, d) 1.91-1.97 (2H, m) 1.76-1.84 (1H, m) 1.45-1.55 (1H, m) 0.87-0.92 (1H, m).

Example 21

1-(3-{(1S,5R)-1-[4-(trifluoromethyl)phenyl]-3-azabicyclo[3.1.0]hex-3-yl}propyl)-5-[3-(trifluoromethyl)-1H-pyrazol-1-yl]-2,4(1H,3H)-pyrimidinedione dihydrochloride (E21)

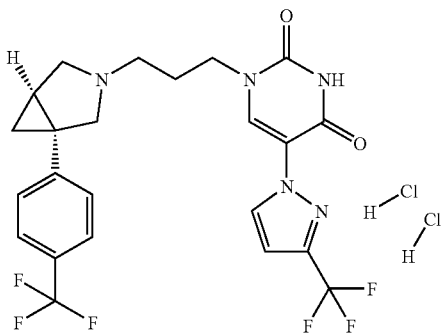

1-(3-{(1S,5R)-1-[4-(trifluoromethyl)phenyl]-3-azabicyclo[3.1.0]hex-3-yl}propyl)-5-[3-(trifluoromethyl)-1H-pyrazol-1-yl]-2,4(1H,3H)-pyrimidinedione (E20, 10.3 mg, 0.020 mmol) was dissolved in Diethyl ether (2 ml). 1M solution of HCl in Diethyl ether (0.044 ml, 0.044 mmol) was added. The solvent was evaporated to obtain 11.6 mg of the title compound as a yellow powder.

MS (ES) (m/z): 514.13.

1H NMR (400 MHz, DMSO-$d_6$) δ ppm 12.02 (1H, s) 10.41 (1H, br. s.) 8.42 (1H, s) 8.26-8.28 (1H, m) 7.70 (2H, d) 7.49 (2H, d) 6.94 (1H, d) 4.01-4.09 (1H, m) 3.87 (2H, t) 3.72 (1H, dd) 3.57-3.67 (1H, m) 3.46-3.54 (1H, m) 3.21-3.29 (2H, m) 2.23-2.35 (1H, m) 2.05-2.17 (2H, m) 1.67 (1H, t) 1.14-1.23 (1H, m).

Example 22

5-[3-(trifluoromethyl)-6,7-dihydropyrano[4,3-c]pyrazol-1(4H)-yl]-1-(3-{(1S,5R)-1-[4-(trifluoromethyl)phenyl]-3-azabicyclo[3.1.0]hex-3-yl}propyl)-2,4(1H,3H)-pyrimidinedione (E22)

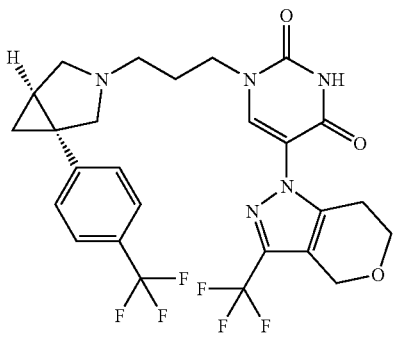

5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 150 mg, 0.282 mmol), copper (1+) iodide (59.1 mg, 0.310 mmol), N,N-dimethylglycine (32.0 mg, 0.310 mmol) and $K_2CO_3$ (86 mg, 0.620 mmol) were dissolved in Dimethyl Sulfoxide (DMSO) (2 ml) to give a light blue solution with a white precipitate. To this mixture, 3-(trifluoromethyl)-1,4,6,7-tetrahydropyrano[4,3-c]pyrazole (starting material prepared according to a similar procedure to that described in Prep38 followed by Prep39, 179 mg, 0.931 mmol) was added. After 18 h shaking at 150° C., the reaction mixture was diluted with EtOAc (5 ml) and the organic phase was washed with water (4×10 ml), then brine (5 ml), dried over $Na_2SO_4$, then filtered and the solvent evaporated. The obtained crude was passed through an SCX cartridge and eluted with 2M solution of ammonia in MeOH. The resulting mixture was further purified by preparative LC-MS to obtain 9.6 mg of the title compound as a free base.

[Preparative LC-MS conditions: Column: Gemini C18 AXIA, 50×21 mm, 5 μm; Mobile phase: A: NH4HCO3 sol. 10 mM, pH 10; B: CH3CN; Gradient: 20% (B) for 1 min, 20% to 60% (B) in 9 min, 60% (B) for 1 min, 60% to 100% (B) in 0.1 min, 100% (B) for 1.9 min; Flow rate: 17 ml/min; UV range: 210-350 nm; Ionization: ES+; Mass range: 100-900 amu].

MS (ES) (m/z): 570.16 [M+H]$^+$.

$^1$H NMR (400 MHz, CHLOROFORM-d) δ ppm 8.65 (1H, br. s.) 7.84 (1H, s) 7.53-7.57 (2H, m) 7.20-7.25 (2H, m) 4.77 (2H, s) 3.91-3.98 (4H, m) 3.42 (1H, d) 3.19 (1H, d) 2.79 (2H, t) 2.56-2.67 (3H, m) 2.51 (1H, dd) 1.90-1.99 (2H, m) 1.79-1.85 (1H, m) 1.35 (1H, t) 0.86 (1H, dd).

Example 23

5-[3-(trifluoromethyl)-6,7-dihydropyrano[4,3-c]pyrazol-1(4H)-yl]-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E23)

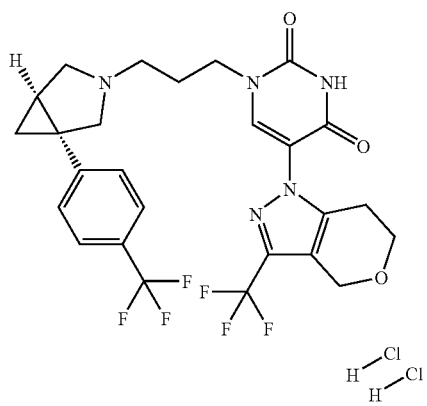

5-[3-(trifluoromethyl)-6,7-dihydropyrano[4,3-c]pyrazol-1(4H)-yl]-1-(3-{(1S,5R)-1-[4-(trifluoromethyl)phenyl]-3-azabicyclo[3.1.0]hex-3-yl}propyl)-2,4(1H,3H)-pyrimidinedione (E22, 9.6 mg, 0.014 mmol) was dissolved and sonicated in Diethyl ether (2 ml) to give a pale yellow solution. 1.25 M solution of HCl in MeOH (0.029 ml, 0.036 mmol) was added at room temperature. The obtained mixture was sonicated for 3 min and the solvent evaporated in vacuo. Obtained 10.1 mg (99% yield) of the title compound as a white solid.

MS (ES) (m/z): 570.14.

$^1$H NMR (400 MHz, DMSO-d$_6$) δ ppm 11.96 (1H, br. s.) 10.22 (1H, br. s.) 8.34 (1H, br. s.) 7.68 (2H, br. s.) 7.25-7.54 (2H, m) 4.68 (2H, s) 4.06 (1H, br. s.) 3.69-3.90 (4H, m) 3.44-3.68 (1H, m) 3.04 (1H, br. s.) 2.61-2.72 (2H, m) 2.38 (1H, br. s.) 2.09 (1H, br. s.) 1.73-1.99 (2H, m) 1.62 (1H, br. s.) 1.39 (1H, br. s.) 1.14-1.30 (1H, m) 0.82 (1H, br. s.).

Example 24

5-[3-(trifluoromethyl)-4,7-dihydropyrano[3,4-c]pyrazol-1(5H)-yl]-1-(3-{(1S,5R)-1-[4-(trifluoromethyl)phenyl]-3-azabicyclo[3.1.0]hex-3-yl}propyl)-2,4(1H,3H)-pyrimidinedione (E24)

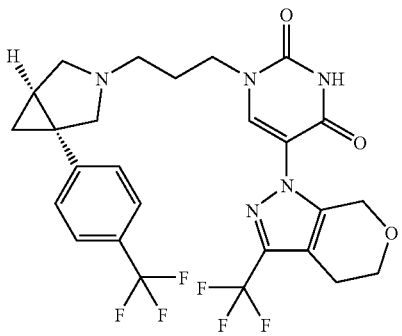

5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 150 mg, 0.282 mmol) copper (1+) iodide (59.1 mg, 0.310 mmol), N,N-dimethylglycine (32.0 mg, 0.310 mmol) and K$_2$CO$_3$ (86 mg, 0.620 mmol) were dissolved in Dimethyl Sulfoxide (DMSO) (2 ml) to give a light blue solution with a white precipitate. To this mixture, 3-(trifluoromethyl)-1,4,5,7-tetrahydropyrano[3,4-c]pyrazole (P38, 179 mg, 0.931 mmol) was added. After 18 h shaking at 150° C., the reaction mixture was diluted with EtOAc (5 ml) and the organic phase was washed with water (4×10 ml), then brine (5 ml), dried over Na$_2$SO$_4$, then filtered and the solvent evaporated. The obtained crude was passed through an SCX cartridge and eluted with 2M solution of ammonia in MeOH. The obtained mixture was iteratively purified (two times) by preparative LC-MS. The obtained fraction was passed through an SCX cartridge and eluted with 2M solution of ammonia. Obtained 8.8 mg of the title compound.

[Preparative LC-MS conditions (first purification): Column: Gemini C18 AXIA, 50×21 mm, 5 µm; Mobile phase: A: NH4HCO3 sol. 10 mM, pH 10; B: CH3CN; Gradient: 35% (B) for 1 min, 35% to 50% (B) in 9 min, 50% (B) for 2 min, 50% to 100% (B) in 0.1 min, 100% (B) for 1.9 min; Flow rate: 17 ml/min; UV range: 210-350 nm; Ionization: ES+; Mass range: 100-900 amu.

Preparative LC-MS conditions (second purification): Column: Supelco ABZ+plus, 10 cm×21.2 mm, 5 µm; Mobile phase: A: H$_2$O+0.1% formic acid; B: CH$_3$CN+0.1% formic acid; Gradient: 25% (B) for 1 min, from 25% to 55% (B) in 9 min, 55% to 100% (B) in 4.6 min, 100% (B) for 0.4 min; Flow rate: 20 ml/min; UV range: 210-4000 nm; Ionization: ES+/ES−; Mass range: 150-900 amu].

MS (ES) (m/z): 570.16 [M+H]$^+$.

$^1$H NMR (400 MHz, CHLOROFORM-d) δ ppm 8.60 (1H, br. s.) 7.89 (1H, s) 7.54 (2H, d) 7.23 (2H, d) 4.71 (2H, s) 3.90-4.00 (4H, m) 3.42 (1H, d) 3.19 (1H, d) 2.80 (2H, t) 2.54-2.67 (3H, m) 2.51 (1H, dd) 1.89-1.99 (2H, m) 1.79-1.85 (1H, m) 1.37 (1H, t) 0.87 (1H, dd).

Example 25

5-[3-(trifluoromethyl)-4,7-dihydropyrano[3,4-c]pyrazol-1(5H)-yl]-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E25)

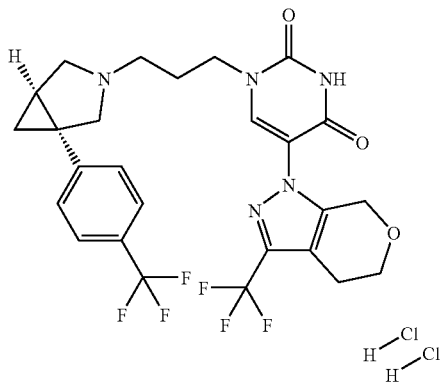

5-[3-(trifluoromethyl)-4,7-dihydropyrano[3,4-c]pyrazol-1(5H)-yl]-1-(3-{(1S,5R)-1-[4-(trifluoromethyl)phenyl]-3-azabicyclo[3.1.0]hex-3-yl}propyl)-2,4(1H,3H)-pyrimidinedione (E24, 8.8 mg, 0.015 mmol) was dissolved and sonicated in Diethyl ether (2 ml) to give a colorless solution. 1.25 M solution of HCl in MeOH (0.030 ml, 0.037 mmol) was added at room temperature. The obtained mixture was sonicated for 3 min and the solvent evaporated in vacuo. Obtained 9.9 mg of the title compound as a white solid.

MS (ES) (m/z): 570.14.

$^1$H NMR (400 MHz, DMSO-d$_6$) δ ppm 11.81-12.05 (1H, m) 10.18 (1H, br. s.) 8.30 (1H, br. s.) 7.55-7.78 (2H, m) 7.48 (1H, br. s.) 7.32 (1H, br. s.) 4.54-4.66 (2H, m) 4.08 (1 H, br. s.) 3.74-3.91 (4H, m) 3.45-3.71 (1H, m) 3.35-3.44 (1H, m) 3.07 (1H, br. s.) 2.64-2.74 (2H, m) 2.27-2.48 (1H, m) 2.09 (1H, br. s.) 1.91 (1H, br. s.) 1.82 (1H, br. s.) 1.38 (1H, br. s.) 1.23 (1H, br. s.) 0.83 (1H, br. s.).

Example 26

1-(3-{(1S,5R)-1-[4-(trifluoromethyl)phenyl]-3-azabicyclo[3.1.0]hex-3-yl}propyl)-5-[3-(trifluoromethyl)-4,5,6,7-tetrahydro-1H-indazol-1-yl]-2,4(1H,3H)-pyrimidinedione (E26)

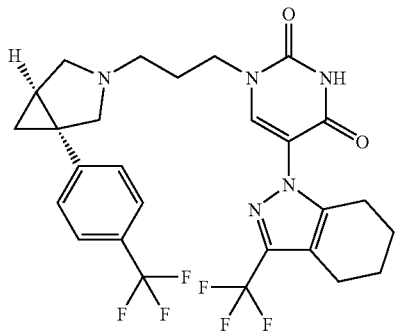

5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 150 mg, 0.282 mmol), copper (1+) iodide (59.1 mg, 0.310 mmol), N,N-dimethylglycine (32.0 mg, 0.310 mmol) and K$_2$CO$_3$ (86 mg, 0.620 mmol) were dissolved in Dimethyl Sulfoxide (DMSO) (2 ml) to give a light blue solution with a white precipitate. To this mixture, 3-(trifluoromethyl)-4,5,6,7-tetrahydro-1H-indazole (commercially available from ABCR, 177 mg, 0.931 mmol) was added. After 18 h shaking at 150° C., the reaction mixture was diluted with EtOAc (5 ml) and the organic phase was washed with water (4×10 ml), then brine (5 ml), dried over Na$_2$SO$_4$, then filtered and the solvent evaporated. The obtained crude was passed through an SCX cartridge and eluted with 2M solution of ammonia in MeOH. The obtained mixture was iteratively purified (two times) by preparative LC-MS. The obtained fraction was passed through an SCX cartridge and eluted with 2M solution of ammonia in MeOH. 9.4 mg (4.99% yield) of the title compound were obtained.

[Preparative LC-MS conditions (first purification): Column: Gemini C18 AXIA, 50×21 mm, 5 μm; Mobile phase: A: NH4HCO3 sol. 10 mM, pH 10; B: CH3CN; Gradient: 40% to 45% (B) in 1 min, 45% to 80% (B) in 7 min, 80% to 100% (B) in 1 min, 100% (B) for 2 min; Flow rate: 17 ml/min; UV range: 210-350 nm; Ionization: ES+; Mass range: 100-900 amu. Preparative LC-MS conditions (second purification): Column: Supelco ABZ+plus, 10 cm×21.2 mm, 5 μm; Mobile phase: A: H$_2$O+0.1% formic acid; B: CH$_3$CN+0.1% formic acid; Gradient: 40% (B) for 1 min, from 40% to 70% (B) in 9 min, 70% to 100% (B) in 4.6 min, 100% (B) for 0.4 min; Flow rate: 20 ml/min; UV range: 210-4000 nm; Ionization: ES+/ES−; Mass range: 150-900 amu].

MS (ES) (m/z): 568.20 [M+H]$^+$.

$^1$H NMR (400 MHz, CHLOROFORM-d) δ ppm 8.67 (1H, br. s.) 7.76 (1H, s) 7.55 (2H, d) 7.22 (2H, d) 3.92 (2H, t) 3.40 (2H, t) 3.18 (1H, d) 2.86 (2H, s) 2.55-2.69 (7H, m) 2.52 (1H, dd) 2.40 (1H, t) 1.99-2.10 (1H, m) 1.90-2.00 (2H, m) 1.37 (1H, t) 0.86 (1H, dd).

Example 27

1-(3-{(1S,5R)-1-[4-(trifluoromethyl)phenyl]-3-azabicyclo[3.1.0]hex-3-yl}propyl)-5-[3-(trifluoromethyl)-4,5,6,7-tetrahydro-1H-indazol-1-yl]-2,4(1H,3H)-pyrimidinedione dihydrochloride (E27)

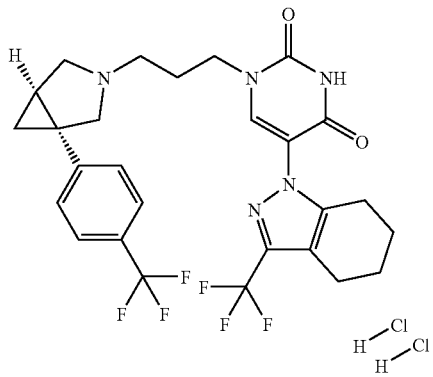

1-(3-{(1S,5R)-1-[4-(trifluoromethyl)phenyl]-3-azabicyclo[3.1.0]hex-3-yl}propyl)-5-[3-(trifluoromethyl)-4,5,6,7-tetrahydro-1H-indazol-1-yl]-2,4(1H,3H)-pyrimidinedione (E26, 9.4 mg, 0.014 mmol) was dissolved and sonicated in Diethyl ether (1 ml) to give a colorless solution. 1.0 M solution of HCl in Diethyl ether (0.035 ml, 0.035 mmol) was added at room temperature. After 3 min and the solvent evaporated in vacuo. Obtained 9.7 mg of the title compound as a white powder.

MS (ES) (m/z): 568.20.

$^1$H NMR (400 MHz, DMSO-d$_6$) δ ppm 11.94 (1H, s) 10.26 (1H, br. s.) 8.32 (1H, s) 7.71 (2H, d) 7.50 (2H, d) 4.06 (1H, dd) 3.83 (2H, t) 3.74 (1H, dd) 3.63 (1H, t) 3.47-3.55 (1H, m) 3.22-3.29 (2H, m) 2.66-2.71 (1H, m) 2.57 (2H, br. s.) 2.27-2.36 (1H, m) 2.19 (1H, t) 2.05-2.15 (2H, m) 1.85-1.95 (1H, m) 1.68-1.78 (3H, m) 1.63 (1H, t) 1.17-1.27 (1H, m).

Example 28

5-(3-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione (E28)

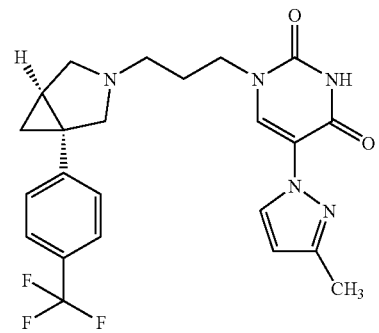

Copper iodide (56.5 mg, 0.297 mmol), (1R,2R)—N,N'-dimethyl-1,2-cyclohexanediamine methyl[(1R,2R)-2-(methylamino)cyclohexyl]amine (169 mg, 1.187 mmol), 5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 150 mg, 0.297 mmol) and K$_2$CO$_3$ (86 mg, 0.623 mmol) were dissolved in Toluene (1.5 ml) to give a blue suspension with a white precipitate. 3-methyl-1H-pyrazole (commercially available from ABCR, 0.029 ml, 0.356 mmol) was added thereto. After shaking at 110° C. for 18 h, the reaction mixture was filtered and the solvent evaporated. The obtained crude was dissolved in 20 mL of DCM and 500 mg of PS-thiol resin and 2.0 g of MP-isocyanate resin were added to blue solution. The obtained suspension was shaken for 2 h at 35° C., then filtered and the solvent evaporated. The resulting mixture was iteratively purified (two times) by preparative LC-MS. Obtained 51.8 mg of the title compound.

[Preparative LC-MS conditions (first purification): Column: WATERS XTerra prep MS C18 OBD, 30×150 mm, 10 μm; Mobile phase: A: H$_2$O+0.1% formic acid; B: CH$_3$CN+0.1% formic acid; Gradient: 20% to 45% (B) in 10 min, 45% to 99% (B) in 4 min, 95% to 100% (B) in 1 min. Flow rate: 40 ml/min; UV range: 210-400 nm; Ionization: ES+/ES−; Mass range: 150-900 amu.

Preparative LC-MS conditions (second purification): Column: WATERS XTerra prep MS C18 OBD, 30×150 mm, 10 μm; Mobile phase: A: NH$_4$HCO$_3$ sol. 10 mM, pH 10; B: CH$_3$CN; Gradient: 10% (B) for 0.5 min, 10% to 95% (B) in 12.5 min, 95% to 100% (B) in 3 min. Flow rate: 40 ml/min; UV range: 210-400 nm; Ionization: ES+/ES−; Mass range: 130-900 amu].

MS (ES) (m/z): 460.18 [M+H]$^+$.

$^1$H NMR (400 MHz, CHLOROFORM-d) δ ppm 8.76 (1H, s) 8.29 (1H, d) 8.14 (1H, s) 7.55 (2H, d) 7.23 (2H, d) 6.21 (1H, d) 3.86-4.00 (2H, m) 3.44 (1H, d) 3.18 (1H, d) 2.53-2.67 (3H, m) 2.50 (1H, dd) 2.31 (3H, s) 1.89-2.00 (2H, m) 1.79-1.85 (1H, m) 1.56 (1H, t) 0.89 (1H, dd).

Example 29

5-(3-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E29)

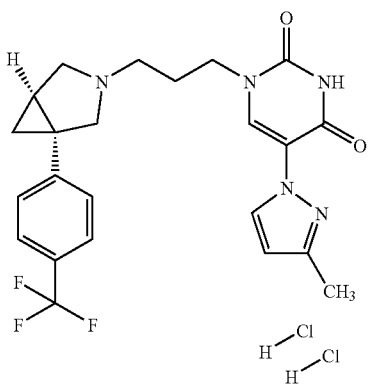

5-(3-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione (E28, 51.8 mg, 0.113 mmol) was dissolved and sonicated in Diethyl ether (1 ml) to give a colorless solution. 1.25 M solution of HCl in MeOH (0.225 ml, 0.282 mmol) was added at room temperature. After 3 min and the solvent in vacuo. Obtained 50.8 mg of the title compound as a white powder.

MS (ES) (m/z): 460.20.

Example 30

1-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-1H-pyrazole-3-carbonitrile (E30)

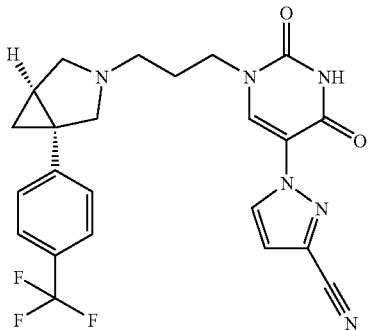

Copper(1+) iodide (50.1 mg, 0.263 mmol), (1R,2R)—N,N'-dimethyl-1,2-cyclohexanediamine methyl[(1R,2R)-2-(methylamino)cyclohexyl]amine (0.166 ml, 1.053 mmol), 5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 133 mg, 0.263 mmol) and $K_2CO_3$ (76 mg, 0.553 mmol) were dissolved in Toluene (1 ml) to give a blue suspension with a white precipitate. 1H-pyrazole-3-carbonitrile (commercially available from Tyger, 29.4 mg, 0.316 mmol) was added thereto. After shaking at 110° C. for 18 h, the reaction mixture was filtered and the solvent evaporated. The obtained residue was purified by flash chromatography (eluent: pure EtOAc for 4CV, then from pure EtOAc to EtOAc/MeOH 9:1 in 10 CV, then EtOAc/MeOH 9:1 for 10 CV; 12M column) to obtain 14.5 mg of our target compound that was further purified on a SCX cartridge and eluted with a 2M solution of ammonia in MeOH. The resulting solution was evaporated in vacuo to obtained 10.9 mg of title compound as a white solid.

MS (ES) (m/z): 471.15 [M+H]$^+$.

$^1$H NMR (400 MHz, CHLOROFORM-d) δ ppm 8.54 (1H, d) 8.35 (1H, s) 7.55 (2H, d) 7.26 (2H, d) 6.82 (1H, d) 3.98 (2H, t) 3.41 (1H, d) 3.17 (1H, d) 2.56-2.64 (3H, m) 2.53 (1H, dd) 1.91-2.01 (2H, m) 1.80-1.87 (1H, m) 1.50 (1H, t) 0.94 (1H, dd).

Example 31

5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione (E31)

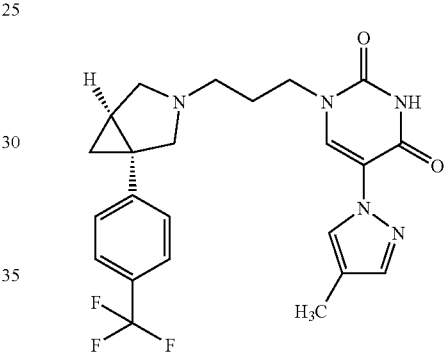

Copper(1+) iodide (56.5 mg, 0.297 mmol), (1R,2R)—N,N'-dimethyl-1,2-cyclohexanediamine methyl[(1R,2R)-2-(methylamino)cyclohexyl]amine (169 mg, 1.187 mmol), 5-iodo-1-(3-{(1S,5R)-1-[4-(trifluoromethyl)phenyl]-3-azabicyclo[3.1.0]hex-3-yl}propyl)-2,4(1H,3H)-pyrimidinedione (Prep10, 150 mg, 0.297 mmol) and $K_2CO_3$ (86 mg, 0.623 mmol) were dissolved in Toluene (1.5 ml) to give a blue suspension with a white precipitate. 4-methyl-1H-pyrazole (commercially available from Fluka 0.029 ml, 0.356 mmol) was added thereto. After shaking for 18 h at 110° C. the reaction mixture was filtered and the solvent evaporated. The resulting mixture was dissolved in 20 mL of DCM to obtain a blue solution in which 500 mg of PS-thiol and 2.0 g of MP-isocyanate were added. The suspension was shaken at 35° C. for 2 h, then filtered and the solvent evaporated. The resulting mixture was iteratively purified (two times) by preparative LC-MS. Obtained 4.8 mg of the title compound.

[Preparative LC-MS conditions (first purification): Column: WATERS XTerra prep MS C18 OBD, 30×150 mm, 10 μm; Mobile phase: A: $H_2O$+0.1% formic acid; B: $CH_3CN$+ 0.1% formic acid; Gradient: 20% to 45% (B) in 10 min, 45% to 99% (B) in 4 min, 95% to 100% (B) in 1 min. Flow rate: 40 ml/min; UV range: 210-400 nm; Ionization: ES+/ES−; Mass range: 150-900 amu.

Preparative LC-MS conditions (second purification): Column: Gemini C18 AXIA, 50×21 mm, 5 μm; Mobile phase: A: $NH_4HCO_3$ sol. 10 mM, pH10; B: $CH_3CN$; Gradient: form 30% (B) to 35% (B) in 1 min, from 35% (B) to 65% (B) in 7 min, from 65% (B) to 100% (B) in 1 min, 100% (B) for 1.5 min; Flow rate: 17 ml/min; UV range: 210-350 nm; Ionization: ES+; Mass range: 100-900 amu].

MS (ES) (m/z): 460.16 [M+H]+.

1H NMR (400 MHz, CHLOROFORM-d) δ ppm 8.40 (1H, s) 8.12 (1H, t) 8.06 (1H, s) 7.55 (2H, d) 7.45 (1H, s) 7.23 (2H, d) 3.88-3.96 (2H, m) 3.40 (1H, d) 3.14 (1H, d) 2.53-2.65 (3H, m) 2.49 (1H, dd) 2.15 (3H, s) 1.90-1.99 (2H, m) 1.78-1.83 (1H, m) 1.49 (1H, t) 0.87 (1H, dd).

Example 32

5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)pyrimidinedionedihydrochloride (E32)

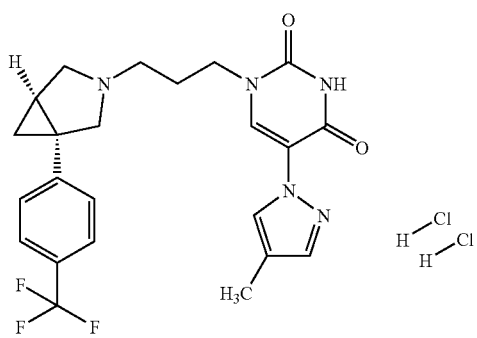

5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione (E31, 4.8 mg, 9.92 μmol) was dissolved and sonicated in Diethyl ether (1 ml) to give a colorless solution. 1.0 M solution of HCl in Diethyl ether (0.025 ml, 0.025 mmol) was added at room temperature. After 3 min the solvent was evaporated to obtain 5.3 mg of the title compound as a white powder.

MS (ES) (m/z): 460.16.

Example 33

5-(3-methyl-1,2,4-oxadiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E33)

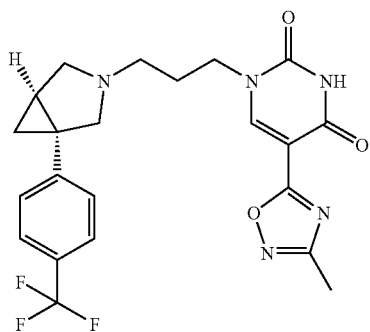

In a 0.5/2 mL sealed MW vial (1S,5R)-3-(3-chloropropyl)-1-[4-(trifluoromethyl)phenyl]-3-azabicyclo[3.1.0]hexane (Prep5, 62.6 mg, 0.206 mmol) was dissolved in Dimethyl Sulfoxide (DMSO) (0.8 ml), and, 6-hydroxy-5-(3-methyl-1,2,4-oxadiazol-5-yl)-2(1H)-pyrimidinone (Prep33, 40 mg, 0.206 mmol), Sodium iodide (46.3 mg, 0.309 mmol) and Dipea (0.126 mL, 0.721 mmol) were then added. The red mixture so obtained was heated at 120° C. for 4 h, then left at 80° C. overnight. The day after DIPEA (0.054 mL, 0.310 mmol) was added and the mixture and the heated at 120° C. for further 4 h. The mixture was treated with EtOAc and washed with NH4Cl sat. sol. The organic phase was dried over Na2SO4 anhydrous, filtered and evaporated under reduced pressure providing a brown residue. The crude was purified first by SCX cartridge and then by Biotage Si 12+M cartridge with a gradient of DCM/DCM/MeOH (9:1). 19 mg of the title compound were obtained as a yellow oil.

MS (ES) (m/z): 462.16 [M+H]+.

1H NMR (400 MHz, CHLOROFORM-d) δ ppm 8.45 (1H, s) 8.21 (1H, s), 7.48 (2H, d), 7.2 (2H, d) 3.88-4.03 (2H, t) 3.41 (1H, d) 3.14 (1H, d) 2.59-2.64 (1H, d) 2.49 (2H, q) 2.53 (1H, dd) 2.41 (3H, s), 1.96 (2H, m) 1.78-1.81 (1H, m) 1.48 (1H, t) 0.91 (1H, q).

Example 34

5-(3-methyl-1,2,4-oxadiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E34)

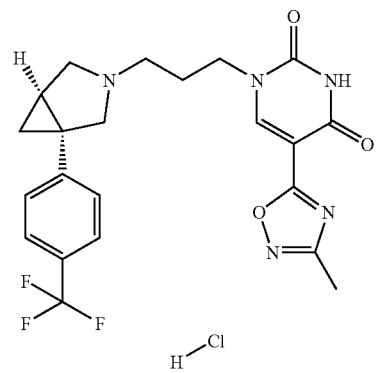

5-(3-methyl-1,2,4-oxadiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E33, 19 mg, 0.014 mmoles) was dissolved in DCM (1 mL) and 45 μL of HCl (as a 1.0M solution in diethylether) were added. The solution was evaporated under nitrogen stream and the residue was triturated with 0.5 mL of diethylether. Then diethylether was eliminated and the title compound (17 mg, 0.034 mmol) was obtained as a beige solid.

1H NMR (400 MHz, CHLOROFORM-d) δ ppm 11.8 (1H, s), 10.48 (1H, s), 8.91 (1H, s), 7.63 (2H, d), 7.79 (2H, d), 4.01 (1H, m), 3.88 (2H, m), 3.67 (1H, m), 3.56 (1H, m), 3.44 (1H, d), 3.30 (1H, t), 3.14 (1H, d) 2.59-2.64 (1H, d) 2.49 (2H, q) 2.53 (1H, dd) 2.41 (3H, s), 1.96 (2H, m) 1.78-1.81 (1H, m) 1.48 (1H, t) 0.91 (1H, q).

Example 35

5-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione (E35)

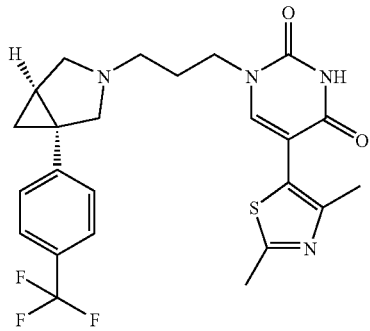

(1S,5R)-1-[4-(trifluoromethyl)phenyl]-3-azabicyclo[3.1.0]hexane (94 mg, 0.413 mmol), 1-(4-chlorobutyl)-5-(2,4-dimethyl-1,3-thiazol-5-yl)-2,4(1H,3H)-pyrimidinedione (Prep37, 108 mg, 0.344 mmol), potassium carbonate (71.3 mg, 0.516 mmol) and sodium iodide (77 mg, 0.516 mmol) were suspended in N,N-Dimethylformamide (DMF) (2 mL) and the reaction mixture was stirred at 65° C. overnight. The day after still presence of starting material was detected, thus reaction was stirred at 100° C. for further 4 hours.

Afterwards the reaction mixture was quenched with water and extracted with AcOEt. Organic phase was washed with brine, dried and concentrated under reduced pressure. Crude was purified by SCX cartridge and further purified by flash chromatography (eluent: DCM to DCM/MeOH/NH3 9:1:0.1) affording the title compound (51.7 mg, 0.102 mmol) as a clear oil.

$^1$H NMR (400 MHz, CHLOROFORM-d) δ: ppm 8.69 (br. s., 1H), 7.54 (d, 2H), 7.31 (s, 1H), 7.23 (d, 2H), 3.85 (t, 2H), 3.37 (d, 1H), 3.13 (d, 1H), 2.68 (s, 3H), 2.65-2.53 (m, 3H), 2.53-2.46 (m, 1H), 2.42 (s, 3H), 1.89-1.75 (m, 3H), 1.63-1.54 (m, 2H), 1.53-1.44 (m, 1H), 0.90-0.82 (m, 1H).

Example 36

5-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione dihydrochloride (E36)

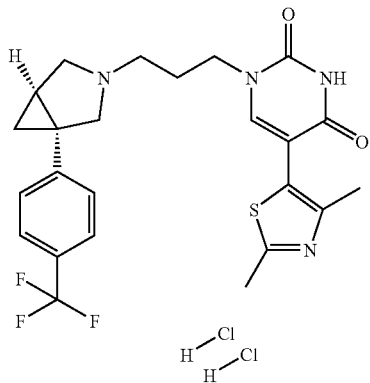

5-(2,4-dimethyl-1,3-thiazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione (E35) was dissolved in DCM and treated with HCl 1N solution in Et2O (2.2 eq) to form the title compound (31 mg, 0.054 mmol) as a white powder.

MS (ES) (m/z): 505.21 [M+H]$^+$.

Example 37

5-(2,4-dimethyl-1,3-thiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E37)

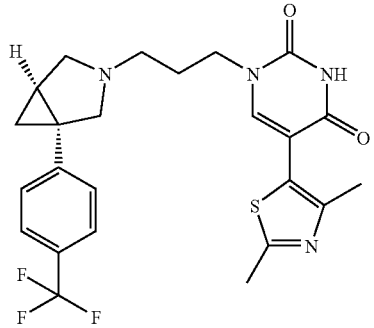

To a solution of (1S,5R)-1-[4-(trifluoromethyl)phenyl]-3-azabicyclo[3.1.0]hexane (269 mg, 1.186 mmol) in acetonitrile (4 mL), Titanuim (IV) isopropoxide (0.434 mL, 1.482 mmol) and a solution of 3-[5-(2,4-dimethyl-1,3-thiazol-5-yl)-2,4-dioxo-3,4-dihydro-1(2H)-pyrimidinyl]propanal (Prep36, 276 mg, 0.988 mmol) in acetonitrile (6 mL) were added and the mixture was stirred at rt for 20 minutes. Afterwards, it was cooled to 0° C. and Sodiumtriacetoxyborohydride (314 mg, 1.482 mmol) was added. The mixture was stirred at rt for 1.5 h, then quenched with water. Acetonitrile was eliminated under reduced pressure and the aqueous residue was extracted with DCM. Organic phase was washed with NaHCO3 saturated solution, dried and concentrated under vacuum. Crude product was purified by flash chromatography (eluent: DCM/MeOH/NH3 97:3:0.1) affording the title compound (E37, 200 mg, 0.408 mmol) as a white solid.

$^1$H NMR (400 MHz, CHLOROFORM-d) δ: ppm 8.27 (br. s., 1H), 7.54 (d, 2H), 7.38 (s, 1H), 7.22 (d, 2H), 3.97-3.86 (m, 2H), 3.32 (d, 1H), 3.08 (d, 1H), 2.69 (s, 3H), 2.65-2.55 (m, 3H), 2.55-2.48 (m, 1H), 2.42 (s, 3H), 1.98-1.90 (m, 2H), 1.85-1.75 (m, 1H), 1.41-1.38 (m, 1H), 0.90-0.87 (m, 1H).

Example 38

5-(2,4-dimethyl-1,3-thiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E38)

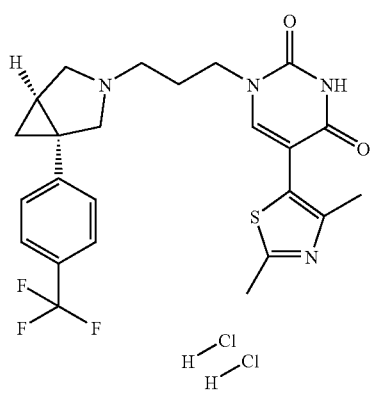

5-(2,4-dimethyl-1,3-thiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione (E37) was dissolved in DCM and treated with HCl 1N in Et2O (2.2 eq) to form the corresponding dihydrochloride salt that was triturated with Et2O to give the title compound (E38, 226 mg, 0.40 mmol) as a white solid.

$^1$H NMR (500 MHz, DMSO-d$_6$) δ: ppm 11.71 (s, 1H), 10.74 (br. s., 1H), 7.95 (s, 1H), 7.70 (d, 2H), 7.48 (d, 2H), 4.05 (q, 1H), 3.89-3.84 (m, 2H), 3.70 (q, 1H), 3.60 (t, 1H), 3.60 (t, 1H), 3.44-3.51 (m, 1H), 3.20-3.30 (m, 2H), 2.61 (s, 3H), 2.35 (s, 3H), 2.26-2.31 (m, 1H), 2.07-2.16 (m, 2H), 1.77 (t, 1H), 1.15-1.21 (m, 1H).

Example 39

5-(4-methyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (E39)

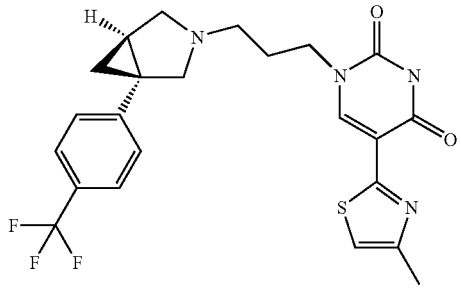

3-[5-(4-methyl-1,3-thiazol-2-yl)-2,4-dioxo-3,4-dihydro-1(2H)-pyrimidinyl]propanal (Prep.45, 0.109 mmol) was suspended in 1,2-Dichloroethane (DCE) (1 ml) and Acetonitrile (1 ml). Acetic acid (9.36 μl, 0.164 mmol) followed by (1S, 5R)-1-[4-(trifluoromethyl)phenyl]-3-azabicyclo[3.1.0]hexane (P4 24.77 mg, 0.109 mmol) were added and the mixture was stirred at rt for 20 minutes. Then the resulting solution was cooled to 0° C. and SODIUM TRIACETOXYBOROHYDRIDE (25.4 mg, 0.120 mmol) was added. The mixture was allowed to reach r.t. under stirring and left at rt overnight. The mixture was treated with NaHCO3 aqueous saturated solution (5 mL) and extracted with EtOAc (3×5 mL). The organic was dried (Na2SO4 and rotary) to afford a yellow solid that was submitted to LC preparative purification. Fractions were collected, dried under vacuum to afford the title compound as a white solid (6.8 mg, 12%).

MS (ES) (m/z): 477 [M+H]$^+$.
$^1$H-NMR (600 MHz, CHLOROFORM-d) d ppm 0.92 (q, 1H) 1.62 (t, 1H) 1.79-1.84 (m, 1H) 1.92-1.99 (m, 2H) 2.43 (s, 3H) 2.47-2.63 (m, 4H) 3.16 (d, 1H) 3.41 (d, 1H) 3.93-4.04 (m, 2H) 6.92 (s, 1H) 7.22 (d, 2H) 7.53 (d, 2H) 8.30 (br. s., 1H) 8.59 (s, 1H).

Example 40

5-(4-methyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E40)

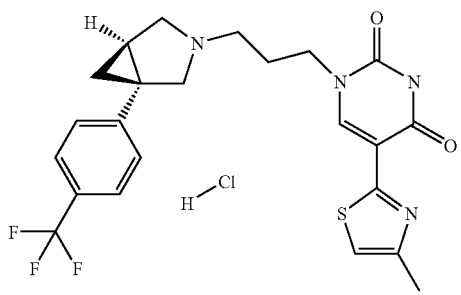

5-(4-methyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione (E39, 5.8 mg, 0.012 mmol) was suspended in Diethyl ether (1 ml) and treated with 1 M HYDROCHLORIC ACID (0.015 ml, 0.015 mmol) in Et2O. The precipitate formed was triturated with Et2O (3×04 mL) and dried to afford the title compound as a grayish solid (6 mg, 88% yield).

MS (ES) (m/z): 477 [M+H]$^+$.
$^1$H-NMR (400 MHz, DMSO-d$_6$) δ: ppm 1.13-1.27 (m, 1H) 1.51-1.61 (m, 1H) 2.04-2.20 (m, 2H) 2.24-2.36 (m, 1H) 2.40 (s, 3H) 2.65-2.72 (m, 1H) 3.22-3.35 (m, 2H) 3.60-3.69 (m, 1H) 3.69-3.81 (m, 1H) 3.91-4.02 (m, 2H) 4.02-4.12 (m, 1H) 7.19-7.44 (m, 1H) 7.45-7.54 (m, 2H) 7.67-7.75 (m, 2H) 8.65 (s, 1H) 9.95-10.16 (brm, 1H) 11.85-12.02 (brs, 1H)

Example 41

5-(3-methyl-4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione (E41)

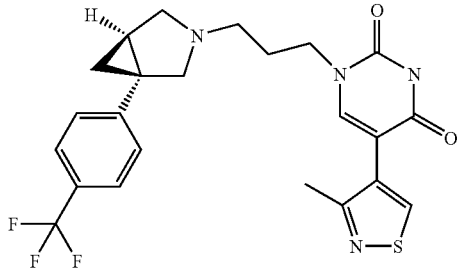

3-[5-(3-methyl-4-isothiazolyl)-2,4-dioxo-3,4-dihydro-1(2H)-pyrimidinyl]propanal (Prep 0.126 mmol) was dissolved in 1,2-Dichloroethane (DCE) (1 ml). (1S,5R)-1-[4-(trifluoromethyl)phenyl]-3-azabicyclo[3.1.0]hexane (P4, 28.6 mg, 0.126 mmol) and ACETIC ACID (0.022 ml, 0.378 mmol) were added and the mixture was stirred at rt for 15 minutes. Then it was cooled at 0° C. and SODIUM TRIACETOXYBOROHYDRIDE (29.4 mg, 0.139 mmol) was added. The mixture was stirred at 0° C. for 3 hours. The mixture was treated with NaHCO3 aqueous saturated solution (5 mL) and extracted with DCM (3×5 mL). The organic were filtered on a separatory cartridge, combined and dried to afford a crude that was submitted to LC preparative purification. Fraction collected was dried (rotary) to afford the title compound as a white solid (8.7 mg, 14% yield).

MS (ES) (m/z): 477 [M+H]$^+$.
1H NMR (400 MHz, CHLOROFORM-d) δ: ppm 0.80-1.00 (m, 1H) 1.34-1.47 (m, 1H) 1.75-1.87 (m, 1H) 1.89-2.05 (m, 2H) 2.46-2.55 (m, 4H) 2.56-2.69 (m, 3H) 3.01-3.14 (m, 1H) 3.26-3.39 (m, 1H) 3.81-4.04 (m, 2H) 7.17-7.26 (m, 2H) 7.35 (s, 1H) 7.51-7.61 (m, 2H) 8.11-8.42 (brm, 1H) 8.51-8.74 (m, 1H)

Example 42

5-(3-methyl-4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E 42)

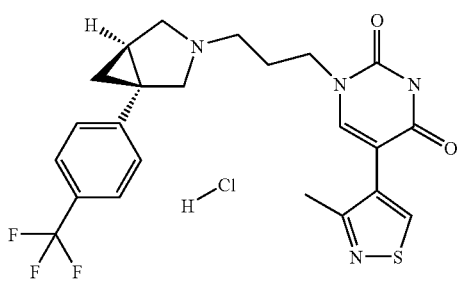

5-(3-methyl-4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione (E41, 8.7 mg, 0.018 mmol) in Et2O (0.5 mL) was treated with HCl (0.022 ml, 0.022 mmol) 1M in Et2O. The white solid formed was triturated with Et2O (2×0.3 mL) and dried to afford the title compound as a white solid (8.3 mg, 84% yield)
MS (ES) (m/z): 477 [M+H]+.
1H NMR (500 MHz, DMSO-d6) δ ppm 1.20 (t, 1H) 1.61 (t, 1H) 2.05-2.14 (m, 2H) 2.27-2.33 (m, 1H) 2.38 (s, 3H) 3.20-3.30 (m, 2H) 3.47-3.54 (m, 1H) 3.62 (t, 1H) 3.70-3.76 (m, 1H) 3.78-3.87 (m, 2H) 4.03-4.09 (m, 1H) 7.48 (d, 2H) 7.71 (d, 2H) 7.88 (s, 1H) 8.86 (s, 1H) 10.21 (br. s., 1H) 11.63 (s, 1H)

Example 43

5-(5-methyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione (E 43)

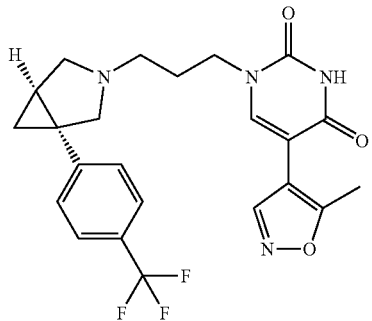

(1S,5R)-1-[4-(trifluoromethyl)phenyl]-3-azabicyclo[3.1.0]hexane (P4, 0.013 g, 0.057 mmol), 3-[5-(5-methyl-4-isoxazolyl)-2,4-dioxo-3,4-dihydro-1(2H)-pyrimidinyl]propanal (0.013 g, 0.052 mmol), SODIUM TRIACETOXYBOROHYDRIDE (0.014 g, 0.068 mmol) and acetic acid (8.96 µl, 0.156 mmol) were stirred in 1,2-Dichloroethane (DCE) (2 ml) at 0° C. for 3 h. Reaction complete at UPLC.
Water (2 mL) and DCM (2 mL) were added, water was extracted with DCM (2×10 mL). Combined organic layers were dried upon sodium sulphate and concentrated to give N4735-9-1.
Crude purified by prep HPLC, obtaining 5 mg of the title compound as free base.
1H NMR (400 MHz, CHLOROFORM-d) ppm 0.90 (dd, 1H) 1.36-1.41 (m, 1H) 1.77-1.84 (m, 1H) 1.89-2.00 (m, 2H) 2.50 (s, 3H) 2.51-2.64 (m, 4H) 3.06 (d, 1H) 3.31 (d, 1H) 3.82-3.97 (m, 2H) 7.21 (d, 2H) 7.30 (s, 1H) 7.53 (d, 2H) 8.34 (br. s., 1H) 8.37 (s, 1H)

Example 44

5-(5-methyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E 44)

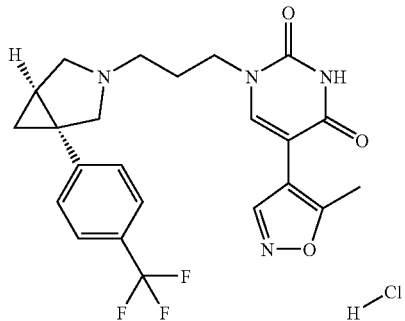

5-(5-methyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione (E43, 5 mg) was converted in chloridrate salt: it was diluted in Diethyl ether (2.000 ml) and HCl 1M in Et2O (20 µmol, 20 µL) was added dropwise under a nitrogen atmosphere. The white solid obtained was triturated in Et2O (2×1 mL), obtaining the tile compound as hydrochloride salt. (5.8 mg).
1H NMR (400 MHz, MeOD) d ppm 1.09-1.58 (m, 4H), 2.12-2.26 (m, 2H), 2.26-2.39 (m, 1H), 2.50 (s, 3H), 3.52-3.73 (m, 2H), 3.76-3.89 (m, 1H), 3.97 (t, 2H), 4.03-4.21 (m, 1H), 7.50 (d, 2H), 7.67 (d, 2H), 7.80 (s, 1H), 8.46 (s, 1H).

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (IA), or a salt thereof

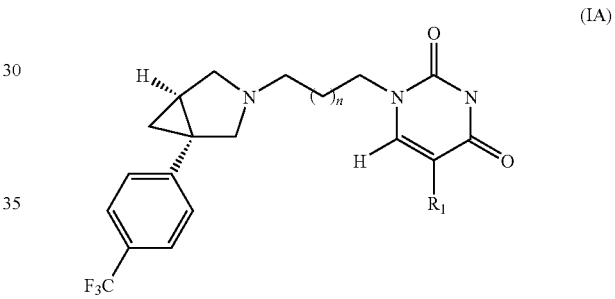

wherein
R1 is a 5-membered heteroaryl group, optionally fused with a 6-membered hetero or carbocycle wherein the 5-membered heteroaryl group or the fused ring system may be optionally substituted by 1, 2, 3 or 4 substituents selected from the group consisting of halogen, cyano, haloC1-4alkyl, C1-4alkoxy, C1-4alkanoyl, haloC1-4alkoxy and SF5;

and n is 1 or 2;

which compound is selected from the group consisting of
5-[1-methyl-3-(trifluoromethyl)-1H-pyrazol-4-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-[1-methyl-3-(trifluoromethyl)-1H-pyrazol-5-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-(1,3-dimethyl-1H-pyrazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(5-methyl-1,3,4-thiadiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4,5-dimethyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-imidazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-pyrrol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-(1,3,5-trimethyl-1H-pyrazol-4-yl)-2,4(1H,3H)-pyrimidinedione;

5-(1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-1,3-thiazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-methyl-1H-pyrazol-4-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-[3-(trifluoromethyl)-1H-pyrazol-1-yl]-2,4(1H,3H)-pyrimidinedione;

5-[3-(trifluoromethyl)-6,7-dihydropyrano[4,3-c]pyrazol-1(4H)-yl]-1-(3-{(1S,5R)-1-[4-(trifluoromethyl)phenyl]-3-azabicyclo[3.1.0]hex-3-yl}propyl)-2,4(1H,3H)-pyrimidinedione;

5-[3-(trifluoromethyl)-4,7-dihydropyrano[3,4-c]pyrazol-1(5H)-yl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[4-(trifluoromethyl)phenyl]-3-azabicyclo[3.1.0]hex-3-yl}propyl)-5-[3-(trifluoromethyl)-4,5,6,7-tetrahydro-1H-indazol-1-yl]-2,4(1H,3H)-pyrimidinedione;

5-(3-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

1-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-1H-pyrazole-3-carbonitrile;

5-(4-methyl-1H-pyrazol-1-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-1,2,4-oxadiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-thiazol-5-yl)-1-[4-{(1S,5R)-1-[4-(trifluoromethyl)phenyl]-3-azabicyclo[3.1.0]hex-3-yl}butyl)-2,4(1H,3H)-pyrimidinedione;

5-(2,4-dimethyl-1,3-thiazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-methyl-1,3-thiazol-2-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-4-isothiazolyl)-1-(3-{(1S,5R)-1-[4-(trifluoromethyl)phenyl]-3-azabicyclo[3.1.0]hex-3-yl}propyl)-2,4(1H,3H)-pyrimidinedione; or 5-(5-methyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

or a salt thereof.

2. A pharmaceutical composition comprising a compound as claimed 1 or a pharmaceutically acceptable salt thereof, in association with a pharmaceutically acceptable carrier.

* * * * *